United States Patent
Klink et al.

(10) Patent No.: US 8,067,536 B2
(45) Date of Patent: Nov. 29, 2011

(54) KINASE AND PHOSPHATASE ASSAYS

(75) Inventors: Tony Klink, Madison, WI (US); Jane Beebe, Elkhorn, WI (US); David Lasky, Madison, WI (US); Karen Kleman-Leyer, Madison, WI (US); Richard Somberg, Madison, WI (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 12/728,926

(22) Filed: Mar. 22, 2010

(65) Prior Publication Data

US 2010/0240080 A1    Sep. 23, 2010

Related U.S. Application Data

(63) Continuation of application No. 11/485,957, filed on Jul. 14, 2006, now Pat. No. 7,727,752, and a continuation-in-part of application No. 10/937,042, filed on Sep. 9, 2004, now Pat. No. 7,619,059, which is a continuation-in-part of application No. 10/903,529, filed on Jul. 29, 2004, now Pat. No. 7,582,461.

(60) Provisional application No. 60/699,174, filed on Jul. 14, 2005, provisional application No. 60/490,771, filed on Jul. 29, 2003.

(51) Int. Cl.
*C07K 4/00* (2006.01)
*C12Q 1/42* (2006.01)

(52) U.S. Cl. ............ 530/328; 530/327; 435/15; 435/21; 435/194; 435/197; 435/212

(58) Field of Classification Search ........................ None
See application file for complete search history.

(56) References Cited

U.S. PATENT DOCUMENTS

| | | |
|---|---|---|
| 3,251,881 A | 5/1966 | Susi et al. |
| 4,000,976 A | 1/1977 | Kramer et al. |
| 4,216,245 A | 8/1980 | Johnson |
| 4,314,936 A | 2/1982 | Yaron et al. |
| 4,372,745 A | 2/1983 | Mandle |
| 4,444,879 A | 4/1984 | Foster et al. |
| 4,444,887 A | 4/1984 | Hoffmann |
| 4,520,110 A | 5/1985 | Stryer et al. |
| 4,542,104 A | 9/1985 | Stryer et al. |
| 4,603,209 A | 7/1986 | Tsien et al. |
| 4,629,783 A | 12/1986 | Cosand |
| 4,670,572 A | 6/1987 | Hinshaw |
| 4,683,195 A | 7/1987 | Mullis et al. |
| 4,711,955 A | 12/1987 | Ward et al. |
| 4,716,111 A | 12/1987 | Osband et al. |
| 4,745,076 A | 5/1988 | Muller |
| 4,774,339 A | 9/1988 | Haugland et al. |
| 4,810,636 A | 3/1989 | Corey et al. |
| 4,812,409 A | 3/1989 | Babb et al. |
| 4,816,397 A | 3/1989 | Boss et al. |
| 4,822,733 A | 4/1989 | Morrison |
| 4,849,362 A | 7/1989 | Demarinis et al. |
| 4,859,582 A | 8/1989 | Stryer et al. |
| 4,883,867 A | 11/1989 | Lee et al. |
| 4,923,802 A | 5/1990 | Gallis |
| 4,927,923 A | 5/1990 | Mathis et al. |
| 4,945,171 A | 7/1990 | Haugland et al. |
| 4,946,778 A | 8/1990 | Ladner et al. |
| 4,957,870 A | 9/1990 | Lee et al. |
| 5,047,519 A | 9/1991 | Hobbs et al. |
| 5,055,556 A | 10/1991 | Stryer et al. |
| 5,104,621 A | 4/1992 | Pfost et al. |
| 5,120,644 A | 6/1992 | Ikenaka |
| 5,125,748 A | 6/1992 | Bjornson et al. |
| 5,132,432 A | 7/1992 | Haugland et al. |
| 5,139,744 A | 8/1992 | Kowalski |
| 5,141,852 A | 8/1992 | Egan et al. |
| 5,162,508 A | 11/1992 | Lehn et al. |
| 5,187,288 A | 2/1993 | Kang et al. |
| 5,196,313 A | 3/1993 | Culbreth |
| 5,206,568 A | 4/1993 | Bjornson et al. |
| 5,220,012 A | 6/1993 | Mathis et al. |
| 5,221,623 A | 6/1993 | Legocki |
| 5,223,409 A | 6/1993 | Ladner et al. |
| 5,225,539 A | 7/1993 | Winter |
| 5,227,487 A | 7/1993 | Haugland et al. |
| 5,242,681 A | 9/1993 | Elgavish et al. |
| 5,242,805 A | 9/1993 | Naleway et al. |
| 5,248,782 A | 9/1993 | Haugland et al. |
| 5,252,492 A | 10/1993 | Yoshikami |
| 5,258,498 A | 11/1993 | Huston et al. |
| 5,262,176 A | 11/1993 | Palmacci |
| 5,264,563 A | 11/1993 | Huse et al. |

(Continued)

FOREIGN PATENT DOCUMENTS

EP    0428000    5/1991

(Continued)

OTHER PUBLICATIONS

U.S. Appl. No. 10/105,735, Requirement for Restriction/Election mailed Apr. 14, 2006.
U.S. Appl. No. 10/105,735, Requirement for Restriction/Election mailed Sep. 27, 2004.
U.S. Appl. No. 10/105,735, Response to Apr. 14, 2006 Office Action, filed May 12, 2006.
U.S. Appl. No. 10/105,735, Response to Sep. 27, 2004 Office Action, filed Oct. 21, 2004.
U.S. Appl. No. 10/936,343, Final OA mailed Apr. 4, 2008.
U.S. Appl. No. 10/936,343, Non Final OA mailed Nov. 28, 2006.
U.S. Appl. No. 10/936,343, Response to Jun. 28, 2005 Restriction Election, filed Dec. 28, 2005.
U.S. Appl. No. 10/936,343, Response to Nov. 28, 2006 Non Final OA, filed Apr. 27, 2007.

(Continued)

*Primary Examiner* — Christina Bradley

(57) ABSTRACT

Compositions, methods, and kits for detecting and monitoring kinase, phosphatase and protein post-translational modification activity are described. The compositions typically include a peptide, a detectable moiety, and a protease cleavage site. Modification of a peptide by a kinase, phosphatase or other protein post-translational modification alters the proteolytic sensitivity of the peptide, resulting in a change of a detectable property of the composition. Panel assays for determining substrates or modulators of kinase, phosphatase or other protein post-translational modification activity are also described.

20 Claims, 9 Drawing Sheets

U.S. PATENT DOCUMENTS

| | | |
|---|---|---|
| 5,268,486 A | 12/1993 | Waggoner et al. |
| 5,274,113 A | 12/1993 | Kang et al. |
| 5,288,514 A | 2/1994 | Ellman |
| 5,314,936 A | 5/1994 | Schwartz et al. |
| 5,316,908 A | 5/1994 | Carlson et al. |
| 5,338,671 A | 8/1994 | Scalice et al. |
| 5,350,564 A | 9/1994 | Mazza et al. |
| 5,352,803 A | 10/1994 | Mattingly |
| 5,355,215 A | 10/1994 | Schroeder |
| 5,362,628 A | 11/1994 | Haugland et al. |
| 5,403,484 A | 4/1995 | Ladner et al. |
| 5,413,923 A | 5/1995 | Kucherlapati et al. |
| 5,427,908 A | 6/1995 | Dower et al. |
| 5,433,896 A | 7/1995 | Kang et al. |
| 5,436,134 A | 7/1995 | Haugland et al. |
| 5,442,045 A | 8/1995 | Haugland et al. |
| 5,445,829 A | 8/1995 | Paradissis et al. |
| 5,445,935 A | 8/1995 | Royer |
| 5,451,343 A | 9/1995 | Neckers et al. |
| 5,459,276 A | 10/1995 | Kuhn et al. |
| 5,486,616 A | 1/1996 | Waggoner et al. |
| 5,491,084 A | 2/1996 | Chalfie et al. |
| 5,501,980 A | 3/1996 | Katerinopoulos et al. |
| 5,516,637 A | 5/1996 | Huang et al. |
| 5,527,670 A | 6/1996 | Stanley |
| 5,527,684 A | 6/1996 | Mabile |
| 5,527,688 A | 6/1996 | Malla et al. |
| 5,532,167 A | 7/1996 | Cantley et al. |
| 5,534,416 A | 7/1996 | Millard et al. |
| 5,534,622 A | 7/1996 | Lehn |
| 5,545,806 A | 8/1996 | Lonberg et al. |
| 5,565,332 A | 10/1996 | Hoogenboom et al. |
| 5,567,952 A | 10/1996 | Kirchner |
| 5,569,587 A | 10/1996 | Waggoner |
| 5,569,766 A | 10/1996 | Waggoner et al. |
| 5,569,825 A | 10/1996 | Lonberg et al. |
| 5,571,698 A | 11/1996 | Ladner et al. |
| 5,571,897 A | 11/1996 | Takalo |
| 5,573,904 A | 11/1996 | Mattingly |
| 5,576,012 A | 11/1996 | Bauer |
| 5,580,717 A | 12/1996 | Dower et al. |
| 5,580,747 A | 12/1996 | Shultz et al. |
| 5,585,089 A | 12/1996 | Queen et al. |
| 5,585,232 A | 12/1996 | Farr |
| 5,589,337 A | 12/1996 | Farr |
| 5,589,351 A | 12/1996 | Harootunian |
| 5,597,910 A | 1/1997 | Gudibande |
| 5,599,906 A | 2/1997 | Dasmahapatra |
| 5,601,845 A | 2/1997 | Buxton |
| 5,601,980 A | 2/1997 | Gordon |
| 5,601,985 A | 2/1997 | Trojanowski et al. |
| 5,602,021 A | 2/1997 | Davis et al. |
| 5,605,809 A | 2/1997 | Komoriya |
| 5,614,191 A | 3/1997 | Puri |
| 5,622,821 A | 4/1997 | Selvin et al. |
| 5,625,048 A | 4/1997 | Tsien |
| 5,625,126 A | 4/1997 | Lonberg et al. |
| 5,627,027 A | 5/1997 | Waggoner |
| 5,628,982 A | 5/1997 | Lauffer et al. |
| 5,631,169 A | 5/1997 | Lakowicz |
| 5,633,425 A | 5/1997 | Lonberg et al. |
| 5,639,615 A | 6/1997 | Selvin |
| 5,641,515 A | 6/1997 | Ramtoola |
| 5,650,289 A | 7/1997 | Wood |
| 5,653,987 A | 8/1997 | Modi |
| 5,654,286 A | 8/1997 | Hostetler |
| 5,656,207 A | 8/1997 | Woodhead |
| 5,656,433 A | 8/1997 | Selvin et al. |
| 5,656,554 A | 8/1997 | Desai et al. |
| 5,658,751 A | 8/1997 | Yue et al. |
| 5,661,016 A | 8/1997 | Lonberg et al. |
| 5,667,809 A | 9/1997 | Trevino |
| 5,674,713 A | 10/1997 | McElroy et al. |
| 5,683,676 A | 11/1997 | Akehurst |
| 5,683,888 A | 11/1997 | Campbell |
| 5,688,529 A | 11/1997 | Lidgate |
| 5,691,145 A | 11/1997 | Pitner et al. |
| 5,696,157 A | 12/1997 | Wang et al. |
| 5,698,426 A | 12/1997 | Huse |
| 5,707,615 A | 1/1998 | Cardin et al. |
| 5,707,641 A | 1/1998 | Gertner |
| 5,714,327 A | 2/1998 | Houthoff et al. |
| 5,721,133 A | 2/1998 | Dasmahapatra |
| 5,721,435 A | 2/1998 | Troll |
| 5,726,181 A | 3/1998 | Hausheer |
| 5,733,734 A | 3/1998 | Trojanowski et al. |
| 5,733,743 A | 3/1998 | Johnson et al. |
| 5,733,888 A | 3/1998 | Carver |
| 5,741,657 A | 4/1998 | Tsien et al. |
| 5,750,753 A | 5/1998 | Kimae et al. |
| 5,756,292 A | 5/1998 | Royer |
| 5,759,787 A | 6/1998 | Strulovici |
| 5,760,188 A | 6/1998 | Beaudet et al. |
| 5,763,198 A | 6/1998 | Hirth et al. |
| 5,766,863 A | 6/1998 | Godowski et al. |
| 5,770,456 A | 6/1998 | Holmes et al. |
| 5,772,926 A | 6/1998 | Akhavan-Tafti |
| 5,773,237 A | 6/1998 | Wong et al. |
| 5,773,273 A | 6/1998 | Nishino |
| 5,777,079 A | 7/1998 | Tsien et al. |
| 5,780,225 A | 7/1998 | Wigler et al. |
| 5,798,276 A | 8/1998 | Haugland et al. |
| 5,800,690 A | 9/1998 | Chow et al. |
| 5,800,996 A | 9/1998 | Lee et al. |
| 5,800,999 A | 9/1998 | Bronstein et al. |
| 5,804,387 A | 9/1998 | Cormack et al. |
| 5,804,395 A | 9/1998 | Schade et al. |
| 5,807,715 A | 9/1998 | Morrison et al. |
| 5,807,746 A | 9/1998 | Lin et al. |
| 5,810,007 A | 9/1998 | Holupka et al. |
| 5,814,318 A | 9/1998 | Lonberg et al. |
| 5,821,047 A | 10/1998 | Garrard et al. |
| 5,830,912 A | 11/1998 | Gee et al. |
| 5,842,974 A | 12/1998 | Stubbs |
| 5,843,746 A | 12/1998 | Tatsumi et al. |
| 5,843,779 A | 12/1998 | Vandermeeren et al. |
| 5,846,737 A | 12/1998 | Kang |
| 5,847,162 A | 12/1998 | Lee et al. |
| 5,863,727 A | 1/1999 | Lee et al. |
| 5,863,753 A | 1/1999 | Haugland et al. |
| 5,882,977 A | 3/1999 | Dunn et al. |
| 5,885,793 A | 3/1999 | Griffiths et al. |
| 5,910,287 A | 6/1999 | Cassin et al. |
| 5,912,137 A | 6/1999 | Tsien et al. |
| 5,916,771 A | 6/1999 | Hori et al. |
| 5,917,012 A | 6/1999 | Nishikata |
| 5,925,517 A | 7/1999 | Tyagi et al. |
| 5,932,474 A | 8/1999 | Tsien et al. |
| 5,939,598 A | 8/1999 | Kucherlapati et al. |
| 5,945,526 A | 8/1999 | Lee et al. |
| 5,969,108 A | 10/1999 | McCafferty et al. |
| 5,989,819 A | 11/1999 | Odawara |
| 5,998,146 A | 12/1999 | Latva |
| 6,001,580 A | 12/1999 | Tani et al. |
| 6,008,373 A | 12/1999 | Waggoner et al. |
| 6,008,378 A | 12/1999 | Tsien et al. |
| 6,008,379 A | 12/1999 | Benson et al. |
| 6,017,712 A | 1/2000 | Lee et al. |
| 6,025,505 A | 2/2000 | Lee et al. |
| 6,027,709 A | 2/2000 | Little et al. |
| 6,040,194 A | 3/2000 | Chick et al. |
| 6,048,982 A | 4/2000 | Waggoner et al. |
| 6,054,271 A | 4/2000 | Tsien et al. |
| 6,066,462 A | 5/2000 | Goueli |
| 6,080,852 A | 6/2000 | Lee et al. |
| 6,103,476 A | 8/2000 | Tyagi et al. |
| 6,114,350 A | 9/2000 | Randall et al. |
| 6,130,101 A | 10/2000 | Mao et al. |
| 6,140,494 A | 10/2000 | Hamilton et al. |
| 6,162,931 A | 12/2000 | Gee et al. |
| 6,180,632 B1 | 1/2001 | Myers et al. |
| 6,184,379 B1 | 2/2001 | Josel et al. |
| 6,197,956 B1 | 3/2001 | Randall et al. |
| 6,200,762 B1 | 3/2001 | Zlokarnik |
| 6,203,994 B1 | 3/2001 | Epps et al. |
| 6,204,389 B1 | 3/2001 | Randall et al. |
| 6,207,397 B1 | 3/2001 | Lynch |

| | | | |
|---|---|---|---|
| 6,221,606 B1 | 4/2001 | Benson et al. | |
| 6,224,644 B1 | 5/2001 | Randall et al. | |
| 6,225,050 B1 | 5/2001 | Waggoner | |
| 6,229,055 B1 | 5/2001 | Klaubert et al. | |
| 6,284,462 B1 | 9/2001 | Sato et al. | |
| 6,323,337 B1 | 11/2001 | Singer et al. | |
| 6,339,392 B1 | 1/2002 | Ashihara | |
| 6,348,596 B1 | 2/2002 | Lee et al. | |
| 6,348,599 B1 | 2/2002 | Cummins et al. | |
| 6,352,672 B1 | 3/2002 | Mabile | |
| 6,358,684 B1 | 3/2002 | Lee | |
| 6,372,445 B1 | 4/2002 | Davis et al. | |
| 6,399,392 B1 | 6/2002 | Haugland et al. | |
| 6,403,807 B1 | 6/2002 | Singh et al. | |
| 6,410,255 B1 | 6/2002 | Pollok et al. | |
| 6,495,350 B1 | 12/2002 | Lee et al. | |
| 6,509,161 B1 | 1/2003 | Barker et al. | |
| 6,511,811 B1 | 1/2003 | Olefsky et al. | |
| 6,562,632 B1 | 5/2003 | Szalecki et al. | |
| 6,589,768 B1 | 7/2003 | Kotewicz et al. | |
| 6,599,711 B2 | 7/2003 | Crouch et al. | |
| 6,610,522 B1 | 8/2003 | Kotewicz et al. | |
| 6,630,311 B2 | 10/2003 | Epps et al. | |
| 6,664,047 B1 | 12/2003 | Haugland et al. | |
| 6,680,173 B2 | 1/2004 | Vanmechelen et al. | |
| 6,716,979 B2 | 4/2004 | Diwu et al. | |
| 6,787,305 B1 | 9/2004 | Li et al. | |
| 6,818,413 B2 | 11/2004 | Epps et al. | |
| 6,835,561 B1 | 12/2004 | Gerard et al. | |
| 6,882,689 B2 | 4/2005 | Maggio et al. | |
| 6,906,104 B2 | 6/2005 | Schostarez | |
| 6,906,194 B2 | 6/2005 | Imperiali et al. | |
| 6,972,198 B2 | 12/2005 | Craig et al. | |
| 6,974,873 B2 | 12/2005 | Leung et al. | |
| 6,977,305 B2 | 12/2005 | Leung et al. | |
| 6,989,259 B2 | 1/2006 | Gerard et al. | |
| 6,991,916 B2 | 1/2006 | Benson et al. | |
| 7,066,889 B2 | 6/2006 | Taylor et al. | |
| 7,262,282 B2 | 8/2007 | Imperiali et al. | |
| 7,582,461 B2 | 9/2009 | Werner et al. | |
| 7,727,752 B2 | 6/2010 | Klink et al. | |
| 2002/0058273 A1 | 5/2002 | Shipwash | |
| 2002/0172991 A1 | 11/2002 | Crouch et al. | |
| 2003/0059811 A1 | 3/2003 | Djaballah et al. | |
| 2003/0162230 A1 | 8/2003 | Reagan et al. | |
| 2003/0162330 A1 | 8/2003 | Aono | |
| 2004/0214227 A1 | 10/2004 | Joly | |
| 2005/0054573 A1 | 3/2005 | Werner et al. | |
| 2005/0064485 A1 | 3/2005 | Vogel | |
| 2007/0054343 A1 | 3/2007 | Sem | |
| 2007/0196860 A1 | 8/2007 | Gee et al. | |
| 2007/0264678 A1 | 11/2007 | Vogel et al. | |
| 2008/0009026 A1 | 1/2008 | Gee | |
| 2008/0050761 A1 | 2/2008 | Imperiali et al. | |
| 2008/0138836 A1 | 6/2008 | Michaud et al. | |
| 2008/0146460 A1 | 6/2008 | Pollok et al. | |

FOREIGN PATENT DOCUMENTS

| | | | |
|---|---|---|---|
| EP | 0639641 | | 2/1995 |
| EP | 0707077 | | 4/1996 |
| EP | 0745690 | | 12/1996 |
| EP | 0680517 | | 11/1997 |
| EP | 0810438 | | 12/1997 |
| EP | 0651825 | | 1/1998 |
| EP | 1201764 | | 1/2004 |
| EP | 1498133 | | 1/2005 |
| WO | WO-90/02809 | | 3/1990 |
| WO | WO-98/24893 | | 6/1990 |
| WO | WO-91/01134 | | 2/1991 |
| WO | WO91/01305 | | 2/1991 |
| WO | WO-91/10741 | | 7/1991 |
| WO | WO91/19735 | | 12/1991 |
| WO | 92/01047 | | 1/1992 |
| WO | WO92/00091 | | 1/1992 |
| WO | WO-92/18619 | | 10/1992 |
| WO | WO-92/22324 | | 12/1992 |
| WO | WO-9303377 | | 2/1993 |
| WO | WO-93/11236 | | 6/1993 |
| WO | WO-93/13423 | | 7/1993 |
| WO | WO93/20242 | | 10/1993 |
| WO | WO-93/20612 | | 10/1993 |
| WO | WO94/17208 | | 8/1994 |
| WO | WO94/28166 | | 12/1994 |
| WO | WO94/28173 | | 12/1994 |
| WO | WO-95/15982 | | 12/1994 |
| WO | WO95/14930 | | 6/1995 |
| WO | WO-95/20401 | | 8/1995 |
| WO | WO95/21191 | | 8/1995 |
| WO | WO-96/23526 | | 1/1996 |
| WO | WO-96/05488 | | 2/1996 |
| WO | WO-9604309 A1 | | 2/1996 |
| WO | WO96/13607 | | 5/1996 |
| WO | WO96/23810 | | 8/1996 |
| WO | WO96/23898 | | 8/1996 |
| WO | WO96/27027 | | 9/1996 |
| WO | WO96/27675 | | 9/1996 |
| WO | WO-96/33735 | | 10/1996 |
| WO | WO-96/34096 | | 10/1996 |
| WO | WO96/38724 | | 12/1996 |
| WO | WO97/28261 | | 8/1997 |
| WO | WO-97/39064 | | 10/1997 |
| WO | WO-97/39326 | | 10/1997 |
| WO | WO98/00231 | | 1/1998 |
| WO | WO98/02571 | | 1/1998 |
| WO | WO98/06701 | | 2/1998 |
| WO | WO-98/09526 | | 3/1998 |
| WO | WO-98/11061 | | 3/1998 |
| WO | WO98/11251 | | 3/1998 |
| WO | WO98/13353 | | 4/1998 |
| WO | WO-98/16654 | | 4/1998 |
| WO | WO-98/50433 | | 5/1998 |
| WO | WO98/32879 | | 7/1998 |
| WO | WO98/36099 | | 8/1998 |
| WO | WO-98/46645 | | 10/1998 |
| WO | WO98/52047 | | 11/1998 |
| WO | WO98/55231 | | 12/1998 |
| WO | WO99/11251 | | 3/1999 |
| WO | WO-9924473 A1 | | 5/1999 |
| WO | WO-9929894 A1 | | 6/1999 |
| WO | WO-9942833 A1 | | 8/1999 |
| WO | WO00/75667 | | 1/2000 |
| WO | WO-0071565 A2 | | 11/2000 |
| WO | WO00/75167 | | 12/2000 |
| WO | WO-01/08712 | | 2/2001 |
| WO | WO-01/09188 | | 2/2001 |
| WO | WO-0111367 A1 | | 2/2001 |
| WO | WO01/36617 | | 5/2001 |
| WO | WO-01/08712 | | 8/2001 |
| WO | WO01/57242 | | 8/2001 |
| WO | WO01/62919 | | 8/2001 |
| WO | WO01/75142 | | 10/2001 |
| WO | WO-0186001 A1 | | 11/2001 |
| WO | WO 01/96594 | | 12/2001 |
| WO | WO-03/011115 | | 2/2003 |
| WO | WO-0196594 | | 9/2003 |
| WO | WO2005/012329 | | 2/2005 |
| WO | WO2005/026730 | | 3/2005 |
| WO | WO-2005/037859 | | 4/2005 |
| WO | WO2006/023810 | | 3/2006 |
| WO | WO2007/051207 | | 5/2007 |
| WO | WO-2007084968 A1 | | 7/2007 |
| WO | WO2008/011601 | | 1/2008 |
| WO | WO-2008016762 A1 | | 2/2008 |

OTHER PUBLICATIONS

U.S. Appl. No. 10/936,343, Restriction Election mailed Jun. 28, 2005.

U.S. Appl. No. 10/937,042, Final Office Action mailed on Apr. 7, 2008, 1-7.

U.S. Appl. No. 10/937,042, Non-Final Office Action mailed on Jan. 22, 2007, 1-13.

U.S. Appl. No. 10/937,042, Office Action Mailed Jun. 17, 2009, 45 pgs.

U.S. Appl. No. 10/937,042, Office Communication: Supplemental Response Request mailed Sep. 17, 2007, Sep. 12, 2007, 1-3.

U.S. Appl. No. 10/937,042, Requirement for Restriction/Election mailed Oct. 11, 2006, 1-16.

U.S. Appl. No. 10/937,042, Response to Jan. 22, 2007 Non-Final Office Action mailed on Jul. 23, 2007, 1-14.
U.S. Appl. No. 10/937,042, Response to Oct. 11, 2006 Restriction Requirement, filed Nov. 9, 2006.
U.S. Appl. No. 10/937,042, Response to Sep. 12, 2007 Office Action, filed Feb. 12, 2008, 1-15.
U.S. Appl. No. 11/554,553, Requirement for Restriction/Election mailed Nov. 5, 2008.
U.S. Appl. No. 11/554,553, Response to Nov. 5, 2008 Office Action, filed Nov. 26, 2008.
U.S. Appl. No. 11/554.553, Office Action mailed Feb. 23, 2009, Feb. 23, 2009, 09 pgs.
U.S. Appl. No. 11/780,059, Requirement for Restriction/Election mailed Mar. 3, 2009.
Bangalore, et al., "Antiserum Raised against a synthetic Phosphotyrosine-Containing Peptide Selectively Recognizes p185neu/erbB-2 and the Epidermal Growth Factor Receptor", *Proceedings of the National Academy of Sciences (PNAS)* vol. 89 1992, 11637-11641.
Beekman, B. et al., "Convenient fluorometric assay for matrix metalloproteinase activity and its application in biological media", *FEBS Letters* 390(2) 1996, 221-225.
Bhatnagar, Deepak et al., "Interaction of Guanosine Cyclic 3'5'-Phosphate Dependent Protein Kinase with lin-Benzoadenine Nucleotides", *Biochemistry* vol. 24, No. 5 1985, 1122-1129.
Cousins-Wasti, R. C. et al., "Determination of Affinities of Ick SH2 Binding Peptides Using a Sensitive Fluorescence Assay: Comparison between the pYEEIP and pYQPQP Consensus Sequences Reveals Context-Dependent Binding Specificity", *Biochemistry* vol. 35, No. 51 1996, 16746-16752.
Cox, D. E. et al., "Mechanism of Calmodulin Inhibition of cAMP-Dependent Protein Kinase Activation of Phosphorylation Kinase.", *Archives of Biochemistry and Biophysics* vol. 259, No. 2 1987, 350-62.
Creasey, et al., "Table of Contents", *Drug Disposition in Humans: The Basis of Clinical Pharmacology* Oxford University Press 1979.
Dandliker, et al., "Equilibrium and Kinetic Inhibition Assays Based upon Fluorescence Polarization", *Methods in Enzymology* vol. 74 1981, 3-28.
Dunn, Ben M. et al., "Fluorescent protein sensors of post-translational modifications", *Methods in Enzymology* vol. 241 1994, 254-279.
Ehrig, Torsten et al., "Green fluorescent protein mutants with altered fluorescence excitation spectra", *FEBS Letters* 367 (2) Jun. 26, 1995, 163-166.
EP04779423, Office Action, mailed on Feb. 10, 2009.
EP04809691, Office Action mailed Apr. 29, 2008.
EP04809691, Office Action mailed May 31, 2007.
EP04809691, Office Action mailed Oct. 17, 2006.
EP04809691, Response to Apr. 29, 2008 Office Action, Filed Jan. 7, 2009.
EP04809691, Response to May 31, 2007 Office Action, Filed Dec. 10, 2007.
EP04809691, Response to Oct. 17, 2006 Office Action, Filed Apr. 27, 2007.
Gil, H. et al., "Effect of non-enzymic glucation on reactivity in proteolysis", *Acta Cientifica Venezolana* vol. 42 1991, 16-23.
Invitrogen Corporation, 11803-012, *Invitrogen Catalog* 2005.
Invitrogen Corporation, 12536-017, *Invitrogen Catalog* 2003.
Invitrogen Corporation, 12588-018, *Invitrogen Catalog* 2005.
Invitrogen Corporation, C6020-03, *Invitrogen Catalog* 2005.
Invitrogen Corporation, P2839, *Invitrogen Catalog* 2005.
Jolley, M., "Fluorescence polarization immunoassay for the determination of therapeutic drug levels in human plasma", *Jour. Anal. Tox.* vol. 5 1981, 236-240.
Kolb, A. J. et al., "Tyrosine kinase assays adapted to homogeneous time-resolved fluorescence", *DDT* vol. 3, No. 7 1998, 333-342.
Kuningas, K., "Homogeneous Assay Technology Based on Upconverting Phosphors", *Anal. Chem.* vol. 77, No. 22 2005, 7348-7355.
Lowery, R. G. et al., "Fluorescence Methods for Dissecting Steroid Hormone Signal Transduction", URL: http://www.invitrogen.com/downloads/LO745.pdf Retrieved Jul. 29, 2005 Feb. 2002 p. 1.

Malencik, Dean A. et al., "Functional Interactions between Smooth Muscle Myosin Light Chain Kinase and Calmodulin", *Biochemistry* vol. 21, No. 17 1982, 4031-4039.
Mathis, G., "Probing molecular interactions with homogeneous techniques based on rare earth cryptates and fluorescence energy transfer", *Clinical Chemistry* vol. 41(9) 1995, 1391-1397.
Parker, Gregory J. et al., "Development of High Throughput Screening Assays Using Fluorescence Polarization: Nuclear Receptor-Ligand-Binding and Kinase/Phosphatase Assays", *Journal of Biomolecular Screening* vol. 5, No. 2 Apr. 2000, 77-88.
PCT/US00/012290, International Search Report mailed Oct. 9, 2000.
PCT/US04/024359, International Preliminary Report on Patentability, Date of Issuance Jan. 30, 2006.
PCT/US04/024359, International Search Report mailed Jul. 20, 2005.
PCT/US04/024359, Written Opinion mailed Jul. 20, 2005.
PCT/US04/029099, International Preliminary Report on Patentability, Date of Issuance Mar. 13, 2006.
PCT/US04/029099, International Search Report mailed on Aug. 18, 2005.
PCT/US04/029099, Written Opinion mailed Aug. 18, 2005.
Tesmer, et al., "Structure of RGS4 Bound to AIF4—Activated Gialpha1: Stabilization of the Transition State for GTP Hydrolysis", *Cell* vol. 89 1997, 251-261.
Weber, Wolfgang et al., "Immunoaffinity purification of the epidermal growth factor receptor. Stoichiometry of binding and kinetics of self-phosphorylation", *The Journal of Biological Chemistry* vol .259, No. 23 Dec. 10, 1984, 14631-14636.
Wei, A. P. et al., "Use of Synthetic Peptides as Tracer Antigens in Fluorescence Polarization Immunoassays of High Molecular Weight Analytes", *Anal. Chem.* vol. 65, No. 23 1993, 3372-3377.
Wu, Pengguang et al., "Resonance Energy Transfer: Methods and Applications", *Analytical Biochemistry* vol. 218, No. 1 1994, 1-13.
Xu, Y. et al., "A bioluminescence resonance energy transfer(BRET)system: application to interacting circadian proteins", *Proceedings of the National Academy of Sciences (PNAS)* vol. 96 1999, 151-156.
Xu, Y. et al., "Bioluminescence resonance energy transfer(BRET) : a new technique for monitoring protein-protein interactions in living cells", *Methods in Enzymol* vol. 360 2003, 289-301.
Yang, et al., "Identification of -R-X-(X)-S/T-Xs-S/T- as Consensus Sequence Motif for Autophosphorylation-Dependent Protein Kinase", *The Journal of Biological Chemistry* 269:47: 1994, 29855-59.
Yao, et al., "Cyclization of Polyubiquitin by the E2-25K Ubiquitin Conjugating Enzyme", *The Journal of Biological Chemistry* vol. 275, No. 47 2000, 36862-36868.
Yaron, et al., "Intramolecularly Quenched Fluorogenic Substrates for Hydrolytic Enzymes", *Analytical Biochemistry* vol. 95 1979, 228-235.
Yokoe, et al., "Spatial dynamics of GFP-tagged proteins investigated by local fluorescence enhancement.", *Nature Biotechnology* vol. 14 1996, 1252-1256.
Zemlan, Frank P. et al., "Monoclonal Antibody PHF-9 Recognizes Phosphorylated Serine 404 of Tau Protein and Labels Paired Helical Filaments", *Journal of Neuroscience Research* vol. 46 1996, 90-97.
U.S. Appl. No. 09/076,115, et al., Gruber, Christian E. filed May 12, 1998, Unpublished Application.
Ausubel, Frederick M. et al., "Current Protocols in Molecular Biology", *John Wiley & Sons, Inc.*, Boston, MA 1994, 4.6.1-4.6.13.
Baldwin, T. O. et al., "Cloning and expression of the luxY gene from *Vibrio fischeri* strain Y-1 in *Escherichia coli* and complete amino acid sequence of the yellow fluorescent protein.", *Biochemistry* 29 1990, 5509-9915.
Berlman, I. B. et al., "Energy Transfer Parameters of Aromatic Compounds", *Academic Press* 1973.
Brautigan, D L. et al., "Methods to distinguish various types of protein phosphatase activity.", *Methods. Enzymol.* 159 1988, 339-346.
Bruchez, Marcel et al., "Semiconductor Nanocrystals as Fluorescent Biological Labels", *American Association for the Advancement of Science*, US, Sep. 25, 1998, 2013-2015.

Caravan, et al., "Gadolinium (III) Chelates as MRI Contrast Agents: Structure, Dynamics, and Applications", *Chem. Rev.* 99(9) 1999, 2293-2352.

Cole, S. P. et al., "The EBV-Hybridoma Technique and its Application to Human Lung Cancer", *Monoclonal Antibodies and Cancer Therapy* Alan R. Liss, Inc 1983, 77-96.

Cote, et al., "Generation of Human Monoclonal Antibodies Reactive with Cellular Antigens", *Proceedings of the National Academy of Science USA* 80 1983, 2026-2030.

Dieffenbach, et al., "PCR Primer: A Laboratory Manual", *Cold Spring Harbor Laboratory Press* 1995.

Erlich, et al., "PRC Technology", *Stocton Press* 1989.

Flohe et al., "Kinetics of Purified Catechol O-Methyltransferase", *Biochim. Biophys. Acta.* 220 1970, 469-476.

Guatelli, et al., "Isothermal, In Vitro Amplification of Nucleic Acids by a Multienzyme Reaction Modeled After Retroviral Replication", *Proceedings of the National Academy of Science USA* 87 1990, 1874-1878.

Herman, B. et al., "Resonance Energy Transfer Microscopy, in Fluorescence Microscopy of Living Cells in Culture, Part B, Methods in Cell Biology", *Academic Press* vol. 30, ed. 1989, 219-243.

Huse, W D. et al., "Generation of a large combinatorial library of the immunoglobulin repertoire in phage lambda", *Science* 246 1989, 1275-1281.

Ito, et al., "A Comprehensive Two-Hybrid Analysis to Explore the Yeast Protein Interactome", *Proc Natl Acad Sci USA* 98 2001, 4569-74.

Kohler, et al., "Continuous cultures of fused cells secreting antibody of predefined specificity", *Nature*, 256 1975, 495-497.

Kozbor, et al., "The Production of Monoclonal Antibodies from Human Lymphocytes", *Immunology Today* 4th ed. 1983, 72-79.

Lakowicz, J R. et al., "Emerging applications of fluorescence spectroscopy to cellular imaging: lifetime imaging, metal-ligand probes, multi-photon excitation and light quenching", *Scanning Microsc. Suppl.* vol. 10 vol. 10 1996, 213-24.

Lakowicz, J. R. et al., "Topics in Fluorescence Spectroscopy", *Plenum Press* vols. 1-3 1991.

Lauffer, et al., "Paramagnetic Metal Complexes as Water Proton Relaxation Agents for NMR Imaging: Theory and Design", *Chem. Rev.* 87(5) 1987, 901-927.

Lewis, et al., "PCR's Competitors Are Alive and Well and Moving Rapidly Towards Commercialization", *Genetic Engineering News* 12(9) 1992, 1.

Mullis, et al., "Cold Spring Harbor Symp.", *Quant. Biol* 51 1987, 263.

Myers, T. W. et al., "Reverse Transcription and DNA Amplification by a Thermus thermophilus DNA Polymerase", *Biochemistry* 30, American Chemical Society 1991, 7661-7666.

Norris, B. J. et al., "Nucleotide Sequence of a cDNA Clone Encoding the Precursor of the Peridinin-Chlorophyll a-Binding Protein from the *Dinoflagellate symbiodinium* sp.", *Plant Molecular Biology* 24 1994, 673-677.

Prasher, D. C. et al., "Primary structure of the *Aequorea victoria* green fluorescent protein", *Gene* 111 1992, 229-233.

Sambrook, et al., "Cells: A Laboratory Manual", *Cold Spring Harbor Laborator Press Cold Spring Harbor*, NY 1st edition 1998.

Sambrook, J. et al., "Molecular Cloning, A Laboratory Manual", *Cold Spring Harbor Laborator Press* 2nd Ed 1989, 16.30-16.60.

Spatola, A F. et al., "Peptide Backbone Modifications: A Structure - Activity Analysis of Peptides Containing Amide Bond Surrogates . . . ", *Chemistry and Biochemistry of Amino Acids, Peptides and Proteins* Chap 5 1983, 267-357.

Stemmer, P. M. et al., "Dual Calcium Ion Regulation of Calcineurin by Calmodulin and Calcineurin B", *Biochemistry*; 33 Lab. of Biochemistry, National Inst. of Health, Maryland 1994, 6859-66.

Szent-Gyorgyi, et al., "Cloning and characterization of new bioluminescent proteins", *Progress in Biomedical Optics* 3600 1999, 4-11.

Tilgmann, et al., "Purification and partial characterization of rat liver soluble catechol-O-methyltransferase", *FEBS* 264(1): 1990, 95-99.

Tsien, et al., "Handbook of Biological Confocal Microscopy", Measurement of intracellular Nae concentration 1990, 169-178.

Turro, N. J. et al., "Modern Molecular Photochemistry", *Menlo Park: Benjamin/Cummings Publishing Col, Inc* 1978, 296-361.

Valeur, B et al., "Molecular Fluorescence: Princip", Wiley VCH 2002.

Weber, et al., "Polarization of the Fluorescence of Solutions, in Fluorescence and Phosphorescence Analysis", *Interscience Publishers* Chapter 8 1966, 217-240.

Weiss, et al., "PCR amplification of specific alleles", *Science* 254 1991, 1292.

Wilbanks, S. M. et al., "Rod structure of a phycoerythrin II-containing phycobilisome. I. Organization and sequence of the gene cluster encoding the major phycobiliprotein rod components in the genome of marine *Synechococcus* sp. WH8020.", J. Biol. Chem 268 1993, 1226-1235.

Yolken, et al., "Solid phase capture method for the specific amplification of microbial nucleic acids—avoidance of false-positive and false-negative reactions", *Molecular and Cellular Probes*, 5, 1991, 151-156.

Amerik, "Analysis of the Deubiquitinating Enzymes of the yeast *Saccharomyces cerevisiae*", *The Journal of Biological Chemistry* vol. 381, Issues 9-10, Sep.-Oct. 2000, 981-992.

Angelov, "Characterization of a proline-directed casein kinase from bovine brain", *Archives of Biochemistry and Biophysics* vol. 310, Issue 1, Apr. 1994, 97-107.

Auger, "Quantitative Assays of Mdm2 Ubiquitin Ligase Activity and Other Ubiquitin-Utilizing Enzymes for Inhibitor Discovery", *Methods in Enzymology* vol. 399, 2005, 701-717.

Ausubel, "Introduction to Expression by Fusion Protein Vectors", *Current Protocols in Molecular Biology*, John Wiley and Sons, Inc., 1994, 16.4.1-16.4.4.

Baker, "Ubiquitin-specific proteases of *Saccharomyces cerevisiae*. Cloning of UBP2 and UBP3, and functional analysis of the UBP gene family", *The Journal of Biological Chemistry* vol. 267, No. 32, Nov. 15, 1992, 23364-23375.

Barford, "Protein tyrosine phosphatases take off", *Nature Structural & Molecular Biology* vol. 2, 1995, 1043-1053.

Beasley, "Miniaturization of ultra-high-throughput screening assays into 1536-well format", *Proceedings of SPIE* vol. 4626, Jun. 21, 2002, 556-559.

Beaudette, "Substrate specificity characterization of a cdc2-like protein kinase purified from bovine brain", *Journal of Biochemistry*, vol. 268, No. 28, Oct. 5, 1993, 20825-20830.

Beebe, "A continuous fluorimetric assay for tail-specific protease", *Analytical Biochemistry* vol. 263, Issue 1, Oct. 1, 1998, 51-56.

Beekman, "Highly increased levels of active stromelysin in rheumatoid synovial fluid determined by a selective fluorogenic assay", *FEBS Letters* vol. 418, Issue 3 Dec. 1, 1997, 305-309.

Berkessel, "Fluorescence Reporters for Phosphodiesterase Activity", *Angewandte Chemie International Edition in English* vol. 36, Issue 13-14, Aug. 4, 1997, 1481-1483.

Bolger, "New Applications Using Pan Vera's Fluorescence-based HTS Assays", *Society for Biomolecular Screening, Eighth Annual Conference, Den Haag*, The Netherlands Powerpoint Presentation, Sep. 26, 2002, 30.

Bouvier, "Leishmanolysin: Surface Metalloproteinase of Leishmania", *Methods in Enzymology* vol. 248, 1995, 614-633.

Branchini, "A Computational Analysis of the Unique Protein-Induced Tight Turn That Results in Posttranslational Chromophore Formation in Green Fluorescent Protein", *Journal of the American Chemical Society*, vol. 120, No. 1, Jan. 14, 1998, 1-6.

Brinkley, "A Brief Survey of Methods for Preparing Protein Conjugates with Dyes, Haptens, and Cross-Linking Reagents", *Bioconjugate Chemistry* vol. 3, Issue 1, Jan.-Feb. 1992, 2-13.

Brown, "Fluorine-18-Fluoro-L-DOPA Dosimetry with Carbidopa Pretreatment", *The Journal of Nuclear Medicine* vol. 39, No. 11, Nov. 1998, 1884-1891.

Browning, "Studies on the Differing Effects of the Tumor Necrosis Factor and Lymphotoxin on the Growth of Several Human Tumor Lines", *Journal of Immunology* vol. 143, Issue 6 1989, 1859-1867.

Bundgaard, "Bioreversible derivatives for various functional groups and chemical entities", *Design of Prodrugs, Chapter 1* Amsterdam, Elsevier Science Publishers 1985, 1-92.

Burbaum, "New technologies for high-throughput screening", *Current Opinion Chemistry Biology* vol. 1, Issue 1, 1997, 72-78.

Burrell, *Toxicology of the Immune System: A Human Approach* Van Nostrand Reinhold, division of International Thomson Publishing, Inc. 1992, 7.

Campbell, "Phosphonate Ester Synthesis Using a Modified Mitsunobu Condensation", *Journal of Organic Chemistry* vol. 59, No. 3, 1994, 658-660.

Cartwright, "Use of Beta-Lactamase as a Secreted Reporter of Promoter Function in Yeast", *Yeast*, vol. 10, Issue 4, Apr. 1994, 497-508.

Casey, "Tryptic Hydrolysis at Asparagine Residues in Globin Chains", *Biochimica et Biophysica Acta (BBA)—Protein Structure* vol. 434, Issue 1 May 20, 1976, 184-188.

Catalog No. 539742, "Protein Tyrosine Phosphatase Assay Kit, Fluorometric", *Protocol Calbiochem—Product LIterature*, 3.

Chalfie, "Green Fluorescent Protein as a Marker for Gene Expression", *Science*, vol. 263, Issue 5148 Feb. 11, 1994, 802-805.

Checovich, "Fluorescence polarization-a new tool for cell and molecular biology", *Nature*, vol. 375, May 18, 1995, 254-256.

Chen, "Analogous Organic Synthesis of Small-Compound Libraries: Validation of Combinatorial Chemistry in Small-Molecule Synthesis", *Journal of the American Chemical Society, Chemi* vol. 116, 1994, 2661-2662.

Chen, "In Situ Phosphorylation of Platelet Actin-binding Protein by cAMP-dependent Protein Kinase Stabilizes It against Proteolysis by Calpain", *Journal of Biological Chemistry*, vol. 264, No. 24, Aug. 25, 1989, 14282-14289.

Cheng, "Use of green fluorescent protein variants to monitor gene transfer and expression in mammalian cells", *Nature Biotechnology* vol. 14, Issue 5, May 1996, 606-609.

Cheung, "A Combinatorial Approach to Identifying Protein Tyrosine Phosphatase Substrates from a Phosphotyrosine Peptide Library", *Journal of the American Chemical Society*, vol. 119, No. 40, Oct. 8, 1997, 9568-9569.

Cho, "An Unnatural Biopolymer", *Science* vol. 261, issue 5126, Sep. 3, 1993, 1303-1305.

Chung, "Deubiquitinating Enzymes: Their Diversity and Emerging Roles", *Biochemical and Biophysical Research Communications* vol. 266, Issue 3, Dec. 29, 1999, 633-640.

Ciechanover, "Degradation of MyoD by the Ubiquitin Pathway: Regulation by Specific DNA-binding and Identification of a Novel Site for Ubiquitination", *Molecular Biology Reports* vol. 26, Issue 1-2, Apr. 1999, 59-64.

Ciechanover, "The ubiquitin-proteasome pathway: the complexity and myriad functions of proteins death.", *Proceedings of the National Academy of Sciences (PNAS)* vol. 95, Issue 6, Mar. 17, 1998, 2727-2730.

Clarke, "Protein Isoprenylation and Methylation at Carboxyl-Terminal Cysteine Residues", *Annual Review of Biochemistry* vol. 61, 1992, 355-386.

Clarke, "Signal Transduction: Switching Off MAP Kinases", *Current Biology*, vol. 4 No. 7, Jul. 1, 1994, 647-650.

Cody, "Chemical Structure of the Hexapeptide Chromophore of the Aequorea Green-Fluorescent Protein", *Biochemistry*, vol. 32, No. 5, Feb. 9, 1993, 1212-1218.

Colbran, "A Phenylalanine in Peptide Substrates Provides for Selectivity between cGMP- and cAMP-dependent Protein Kinases", *The Journal of Biological Chemistry*, vol. 267, No. 14, May 15, 1992, 9589-9594.

Creamer, "Interactions between hydrophobic side chains within (alpha)- helics", *Protein Science*, vol. 4, Issue 7, Jul. 1995, 1305-1314.

Cubitt, "Understanding Structure-Function Relationships in the *Aequorea victoria* Green Fluorescent Protein", *Methods in Cell Biology*, vol. 58, Chapter 2, 1999, 19-30.

Cubitt, "Understanding, Improving and Using Green Fluorescent Proteins", *Trends in Biochemical Sciences* vol. 20, Issue 11, Nov. 1995, 448-455.

Dale, "Similar substrate recognition motifs for mammalian AMP-activated protein kinase, higher plant HMG-CoA reductase kinase-A, yeast SNF1, and mammalian calmodulin-dependent protein kinase I", *FEBS Letters*, vol. 361, Issues 2-3, Mar. 20, 1995, 191-195.

Daluge, "1592U89, a Novel Carbocyclic Nucleoside Analog with Potent, Selective Anti-Human Immunodeficiency Virus Activity,", *Antimicrobial Agents and Chemotherapy* vol. 41, No. 5, May 1997, 1082-1093.

Dayhoff, "Detecting Distant Relationships: Computer Methods and Results and Protein Data Information", *Atlas of Protein Sequence and Structure*, vol. 5, Chapter 10, 1972, 101-110.

Deibler, "Limited Digestion of Guinea Pig Myelin Basic Protein and Its Carboxy-Terminal Fragment (Residues 89-169) with *Staphylococcus aureus* V8 Protease", *Journal of Neurochemistry*, vol. 39, No. 4, 1982, 1090-1100.

Dekker, "Protein kinase C—a question of specificity", *TIBS*, vol. 19, Feb. 1994, 73-77.

Delagrave, "Red-Shifted Excitation Mutants of the Green Fluorescent Protein", *Bio Technology*, vol. 13, No. 2, 1995, 151-154.

Demissie, "Insulin resistance, oxidative stress, hypertension, and leukocyte telomere length in men from the Framingham Heart Study", *Aging Cell*, vol. 5, 2006, 325-330.

Denis, "Substrate Specificities for Yeast and Mammalian cAMP-dependent Protein Kinases Are Similar but Not Identical", *The Journal of Biological Chemistry*, vol. 266, No. 27, Sep. 25, 1991, 17932-17935.

Deschamps, "Rapid Purification of Recombinant Green Fluorescent Protein Using the Hydrophobic Properties of an HPLC Size-Exclusion Column", *Protein Expression and Purification*, vol. 6, Feb. 21, 1995, 555-558.

dos Remedios, Cristobal G. "Fluorescence Resonance Energy Transfer Spectroscopy is a Reliable "Ruler" for Measuring Structural Changes in Proteins", *Journal of Structural Biology*, vol. 115 1995, 175-185.

Eldar-Finkelman, "Phosphorylation of insulin receptor substrate 1 by glycogen synthase kinase 3 impairs insulin action", *Proc. Natl. Acad. Sci.*, vol. 94, No. 18, Sep. 2, 1997, 9660-9664.

EP 00932098.7, "Examination Report mailed on Dec. 14, 2004".

EP 00932098.7, "Office Action mailed on Dec. 13, 2005".

EP 00932098.7, "Response to Dec. 13, 2005 Office Action filed on Mar. 23, 2006".

EP 00932098.7, "Response to Dec. 14, 2004 Office Action filed on Oct. 4, 2005".

EP 09180701.6, "Extended European Search Report Recd mailed on May 4, 2010".

EP04779423, "Office Action mailed Jun. 16, 2008".

EP04779423, "Response to Jun. 16, 2008 Office Action, Filed Dec. 23, 2008".

EP04779423, "Supplementary European Search Report mailed Apr. 15, 2008".

Erickson, "Identification by Mass Spectrometry of Threonine 97 in Bovine Myelin Basic Protein as a Specific Phosphorylation Site for Mitogen-activated Protein Kinase,", *The Journal of Biological Chemistry*, vol. 265, No. 32 Nov. 15, 1990, 19728-19735.

Ettehadieh, Elham "Tyrosyl phosphorylation and activation of MAP kinases by p56Ick", *Science*, vol. 255 Feb. 14, 1992, 853-5.

Feil, "Expression of cGMP-dependent protein kinase in *Escherichia coli*", *Molecular and Cellular Biochemistry*, vol. 127, No. 328 1993, 71-80.

Fellmann, "Simplified Protocol of Solid-Phase cDNA Libraries for Multiple PCR Amplification", *Biotechniques* vol. 21, No. 5, 1996, 766,768 & 770.

Fields, "Principles and Practice of Solid-Phase Peptide Synthesis", *Synthetic Peptides: A Users Guide*, Chapter 3, 1992, 77-183.

Fingl, "Basis of Therapeutics", *The Pharmacological Basis of Therapeutics, Fifth Edition, Table of Contents* 1975, xi-xvi.

Forood, "Stabilization of alpha-Helical Structures in Short Peptides via End Capping", *Proceedings of the National Academy of Sciences (PNAS)* vol. 90, Feb. 1993, 838-842.

Fowler, "A Multi-Modality Assay Platform for Ultra-High Throughput Screening", *Current Pharmaceutical Biotechnology*, vol. 1, 2000, 265-281.

Fronczak, J. A. "Rapid Conversion of FP to TR-FRET Assays Using Terbium-based LanthaScreemTM Technology", Url:http://www.invitrogen.com/downloads/76_2-038072.pdf Retrieved Jul. 29, 2005. XP002338477 Sep. 16, 2003, p. 1.

Fuchs, "c-Jun NH2-terminal Kinases Target the Ubiquitination of Their Associated Transcription Factors", *The Journal of Biological Chemistry* vol. 272, No. 51 1997, 32163-8.

Fujimuro, "Production of antipolyubiquitin monoclonal antibodies and their use for characterization and isolation of polyubiquitinated proteins.", *Methods in Enzymology* vol. 399 2005, 75-86.

Fujise, "Specificity of the High Affinity Interaction of Protein Kinase C with a Physiological Substrate, Myristoylated Alanine-rich Protein Kinase C Substrate", *The Journal of Biological Chemistry*, vol. 269, No. 50, Dec. 16, 1994, 31642-31648.

Furniss, Brian S. "Resolution of Racemates", *Vogel's Textbook of Practical Organic Chemistry* Fifth Ed, Longman Group UK Ltd., Essex 1989, 809-823.

Gakamsky, Dmitry M. "Selective steady-state and time-resolved fluorescence spectroscopy of an HLA-A2-peptide complex", *Immunology Letters* vol. 44 1995, 195-201.

Galye, "Identification of regions in interleukin-1 alpha important for activity.", *J Biol Chem*, 268(29):22105-11 Oct. 15, 1993.

Genaro, "Remington's Pharmaceutical Sciences", Mack Publ. Co. 1985, xv-xvi.

Georgi, Ann "Detection of Individual Fluorescently Labeled Reovirions in Living Cells", *Proceedings of the National Academy of Sciences (PNAS)* vol. 87 1990, 6579-6583.

Gonzalez, "Identification of Substrate Recognition Determinants for Human ERK1 and ERK2 Protein Kinases", *The Journal of Biological Chemistry*, vol. 266, No. 33, Nov. 25, 1991, 22159-22163.

Gooley, Andrew A. "Glysocosylation Sites Identified by Detection of Glysocsylated Amino Acids Released from Edman Degration: The Identification of Xaa-Pro-Xaa as a Motif for Thr-O-Glycoslation", *Biochemical and Biophysical Research Communications* vol. 178, No. 3 1991, 1194-1201.

Gordon, "Applications of combinatorial technologies to drug discovery. 2. Combinatorial organic synthesis, library screening strategies, and future directions", *Journal of Medicinal Chemistry* vol. 37, No. 10 1994, 1385-1390.

Graff, "Protein Kinase C Substrate and Inhibitor Characteristics of Peptides Derived from the Myristoylated Alanine-rich C Kinase Substrate (MARCKS) Protein Phosphorylation Site Domain", *The Journal of Biological Chemistry*, vol. 266, No. 22, Aug. 5, 1991, 14390-14398.

Gray, A. "Nonradioactive methods for the assay of phosphoinositide 3-kinases and phosphoinositide phosphatases and selective detection of signaling lipids in cell and tissue extracts", *Anal Biochem*, vol. 313,No. 2, Feb. 15, 2003, 234-245.

Grynkiewicz, Grzegorz "A new generation of Ca++ indicators with greatly improved fluorescent properties", *The Journal of Biological Chemistry* vol. 260, No. 6 1985, 3440-3450.

Hagihara, "Vinylogous Polypeptides: An Alternative Peptide Backbone", *J. Am. Chem. Soc.* vol. 114, No. 16 1992, 6568-6570.

Hamman, Brian D."Dimer/Monomer Equilibrium and Domain Separations of *Escherichia coli* Ribosomal Protein L7/L12", *Biochemistry* vol. 35, No. 51 1996, 16680-16686.

Hanke, J. H. "Discovery of a novel, potent, and Src family-selective tyrosine kinase inhibitor. Study of Lck- and FynT-dependent T cell activation", *The Journal of Biological Chemistry* vol. 271, No. 2 1996, 695-701.

Hanson, "Neuronal Ca2+/Calmodulin-Dependent Protein Kinases", *Annu. Rev. Biochem.*, vol. 61 1992, 586-587.

Harder, Kenneth W. "Characterization and kinetic analysis of the intracellular domain of human protein tyrosine phosphatase beta (HPTP beta) using synthetic phosphopeptides", *Biochemical Journal*, vol. 298 1994, 395-401.

Hardy, "Genetic Variability and Alzheimer's Disease", *Amyloid Protein Precursor in Development, Aging and Alzheimer's Disease*, 1994, 190-198.

Haugland, Rosario P. "Coupling of monoclonal antibodies with fluorophores", *Methods in Molecular Biology*, vol. 45 Monoclonal Antibody Protocols 1995, 205-221.

Haugland, Richard P. "Handbook of Fluorescent Probes and Research Products", *Ch 1-3.3* Molecular Probes, Inc/Invitrogen, 2002 2002, 11-118.

Heim, "Engineering green fluorescent protein for improved brightness, longer wavelengths and fluorescence resonance energy transfer", *Current Biology*, vol. 6, No. 2, 1996, 178-182.

Heim, "Improved green fluorescence", *Nature*, vol. 373, Feb. 23, 1995, 663-664.

Heim, "Wavelength mutations and posttranslational autoxidation of green fluorescent protein", *Proceedings of the National Academy of Sciences (PNAS)* vol. 91, 1994, 12501-12504.

Heller, A. "Electrical Wiring of Redox Enzymes", *Acc. Chem. Res.* vol. 23, No. 5 1990, 128-134.

Hemmila, I. "Time-Resolved Fluorometry: An Overview of the Labels and Core Technologies from Drug Screening Applications", *Drug Discovery Today* vol. 2, No. 9 1997, 373-381.

Hennebicq, "Influence of the Amino Acid Sequence on the MUC5AC Motif Peptide O-Glycosylation by Human Gastric UDP-GaINAc: Polypeptide N-Acetylactoseaminyltransferase(s)", *Glycoconjugate Journal* 15 1998, 275-282.

Hershko, "The ubiquitin system", *Annu. Rev. Biochem.* 67 1998, 425-79.

Hirschmann, "Nonpetidal petidomimetics with a BetaD-Glucose scaffolding. A partial somatostatin agonist bearing a close structural relationship to a potent, selective substance P antagonist", *J. Am. Chem. Soc.* 114 1992, 9217-9218.

Hobbs Dewitt, ""Diversomers": An Approach to Nonpeptide, Nonoligomeric Chemical Diversity", *Proceedings of the National Academy of Sciences (PNAS)* vol. 90 1993, 6909-6913.

Hodgins, "The Tail of a Ubiquitin-conjugating Enzyme Redirects Multi-ubiquitin Chain Synthesis from the Lysine 48-linked Configuration to a Novel Nonlysine-linked Form.", *The Journal of Biological Chemistry* vol. 271, No. 46 1996, 28766-28771.

Hohman, "Anti-AMP Antibody Precipitation of Multiply Adenylylated Forms of Glutamine Synthetase from *Escherichia coli*: A Model Relating Both Concentration and Density of Antigenic Sites with the Antibody-Antigen Interaction", *Proceedings of the National Academy of Sciences (PNAS)* vol. 77, No. 12 1980, 7410-7414.

Holskin, B. P. "A continuous fluorescence-based assay of human cytomegalovirus protease using a peptide substrate", *Analytical Biochemistry* vol. 226 1995, 148-55.

Hong, C. A. "Development of a High Throughout Time-Resolved Fluorescence Resonance Energy Transfer Assay for TRAF6 Ubiquitin Polymerization", *ASSAY and Drug Development Technologies*, vol. 1. No. 1-2 2003, 175-180 pgs.

Horton, Robert A. "A substrate for deubiquitinating enzymes based on time-resolved fluorescence resonance energy transfer between terbium and yellow fluorescent protein", *Analytical Biochemistry* vol. 360 2007, 138-143.

Houghten, "General method for the rapid solid-phase synthesis of large numbers of peptides: Specificity of antigen-antibody interaction at the level of individual amino acids", *Proceedings of the National Academy of Sciences (PNAS)* 82 1985, 5131-5135.

Hurley, "Regulation of an Enzyme by Phosphorylation at the Active Site", *Science*, vol. 249, Aug. 31, 1990, 1012-1016.

Inouye, "Evidence for redox forms of the Aequorea green fluorescent protein", *FEBS Letters*, vol. 351, 1994, 211-214.

Jones, J. H. "A Short Guide to Abbreviations and their Use in Peptide Science", *Journal of Peptide Science* 5 1999, 465-471.

Joshi, Saroj "ATP Synthase Complex from Bovine Heart Mitochondria", *J. Biol. Chem.*, vol. 265, No. 24 1990, 14518-14525.

Jung, Stephanie M. "Crossliking of platelet glycoprotien Ib by N-succinimidyl(4-azidophenyldithio)propionate and 3,3'-dithiobis-(sulfosuccinimidyl propionate)", *Biochimica et Biophysica Acta*, vol. 761, Iss. 2, 1983, 152-162.

Kakinuma, "An N-Linked Glycosylation Motif from the Noncleaving Luteinizing Hormone Receptor Substituted for the Homologous Region (Gly367 to Glu369) of the Thyrotropin Receptor Prevents Cleavage at Its Second, Downstream Site", *The Journal of Biological Chemistry*, vol. 272, No. 45, Nov. 7, 1997, 28296-28300.

Kawakami, "NEDD8 recruits E2-ubiquitin to SCF E3 ligase", *The EMBO Journal* vol. 20, No. 15 2001, 4003-4012.

Kawata, "Post-translationally processed structure of the human platelet protein smg p21 B: Evidence for geranylgenanylation and carboxylmethylation of the C-terminal cysteine", *Proceedings of the National Academy of Sciences (PNAS)* vol. 87 1990, 8960-8964.

Keil, Dietmar "Synthesis and Characterization of 1,3 Bis-(2-dialkylamino 5 thienyl) substituted Squaraines—A Novel Class of Intensively Coloured Panchromatic Dyes", *Dyes and Pigments* vol. 17 1991, 19-27.

Kelly, Susan J. "Hydrolysis of. phosphonate. esters catalyzed by 5'-nucleotide phosphodiesterase.", *Biochemistry* vol. 14, No. 22 1975, 4983-4988.

Kemp, "Design and Use of Peptide Substrates for Protein Kinases", *Methods in Enzymology*, vol. 200, 1991, 121-155.

Kemp, "Method for designing protein kinase inhibitors,", *Trends Biochem. Science*, vol. 15 Sep. 1990, 342-346.

King, "How proteolysis drives the cell cycle", *Science* 274 1996, 1652-59.

Kito, "NUB1, a NEDD8-interacting protein, is induced by interferon and down-regulates the NEDD8 expression.", *The Journal of Biological Chemistry* vol. 276, No. 23 2001, 20603-20609.

Kleman-Leyer, Karen "Speed to Screen: Addressing the Kinase and Phosphatase Assay Development bottleneck with Z'Lyte Technology", *Discovery HTS* vol. 1, Issue 1, 7-10.

Knight, "Fluorimetric Assays of Proteolytic Enzymes", *Methods in Enzymology*, vol. 248, 1995, 18-34.

Krafft, "Synthetic Approaches to Continuous Assays of Retroviral Proteases", *Methods Enzymology*, vol. 241, 1994, 70-86.

Kupcho, K. "A Homogeneous Nonradioactive High Throughput Fluorogenic Protein Kinase Assay", *Analytical Biochemistry* vol. 317(2) 2003, 210-217.

Kwon, "The Active Site Substrate Specificity of Protein Kinase C", *The Journal of Biological Chemistry*, vol. 269, No. 7, Feb. 18, 1994, 4839-4844.

Lee, "A Requirement of Hydrophobic and Basic Amino Acid for Residues for Substrate Recognition by Ca2+/Calmodulin-Dependent Protein Kinase Ia", *Proceedings of the National Academy of Sciences (PNAS)* vol. 91, Jul. 1994, 6413-6417.

Levine, "Isolation and Characterization of a Photoprotein, "Phialidin", and a Spectrally Unique Green-Fluorescent Protein from the Bioluminescent Jellyfish Phialidium Gregarium", *Comp. Biochem. Phyol.* vol. 72B, 1982, 77-85.

Levine, Leanna M. "Measurement of Specific Protease Activity Utilizing Fluorescence Polarization", *Analytical Biochemistry* 247 1997, 83-88.

Li, "Creation of Phosphorylation Sites in Proteins: Construction of a Phosphorylatable Human Interferon Alpha", *Proceedings of the National Academy of Sciences (PNAS)* vol. 86, Jan. 1989, 558-562.

Lim, "Thermosensitivity of Green Fluorescent Protein Fluorescence Utilized to Reveal Novel Nuclear-Like Compartments in Mutant Nucleoporin NSP1", *Journal of Biochemistry*, vol. 118, No. 1 1995, 13-17.

Lindberg, "Dual-specificity protein kinases: will any hydroxyl do?", *TIBS*, 1992, 114-119.

Liu, "Probing the herapin-binding domain of human antithrombin III with V8 Protease", *Eur. J. Biochem.* 167 1987, 247-242.

Loh, Y P. "Evidence that glycosylation of pro-opiocortin and ACTH influences their proteolysis by trypsin and blood proteases", *Molecular and Cellular Endocrinology* vol. 20 1980, 35-44.

London, Erwon "Investigation of membrane structure using fluorescence quenching by spin-labels", *Molecular and Cellular Biochemistry* vol. 45 1982, 181-188.

Lu, "Identification of Substrate Specificity Determinants for the Cell Cycle-regulated NIMA Protein Kinase", *The Journal of Biological Chemistry*, vol. 269, No. 9, Mar. 4, 1994, 6603-6607.

Lu, Frank C. "Table of Contents", *Basic Toxicology: Fundamentals Target Organs and Risk Assessment* Washington 1985, 1-12.

Lynch, B. A. "A Fluorescent Polarization Based Src-SH2 Binding Assay", *Analytical Biochemistry* 247 1997, 77-82.

Ma, Yu-Ting "Substrate specificity of the isoprenylated protein endoprotease", *Biochemistry* vol. 31 1992, 11772-11777.

Malencik, "Characterization of a Fluorescent Substrate for the Adenosine 3',5'-Cyclic Monophosphate-Dependent Protein Kinase", *Analytical Biochemistry*, vol. 132, 1983, 34-40.

Marvel, "Polytetramethylene Sebacate: Pyrophoric Lead as an Ester Interchange Catalyst", *J. Am. Chem. Soc.* 72(1) 1950, 624-625.

Matayoshi, "Novel Fluoregenic Substrates for Assaying Retroviral Proteases by Resonance Energy Transfer", *Science*, vol. 247, Feb. 23, 1990, 954-958.

McDonough, Andrew L. "Effects of Corticosteroids on Articular Cartilage: A Review of the Literature", *Physical Therapy* vol. 62, No. 6 Jun. 1982, 835-839.

Mitchell, "Heat-Stable Inhibitor Protein Derived Peptide Substrate Analogs: Phosphorylation by cAMP-Dependent and cGMP-Dependent Protein Kinases", *Biochemistry*, vol. 34, No. 2, 1995, 528-534.

Mitra, "Fluorescence resonance energy transfer between blue-emitting and red-shifted excitation derivatives of the green fluorescent protein", *Gene*, vol. 173, 1996, 13-17.

Morrison, Larry E. "Detection of Energy Transfer and Fluorescence Quenching", *Nonisotopic DNA Probe Techniques* L. Kricka, ed. 1992, 311-352.

Muhlrad, Denise "A Rapid Method for Localized Mutagenesis of Yeast Genes", *Yeast* vol. 8, John Wiley & Sons Ltd. 1992, 79-82.

Munoz, "Elucidating the folding problem of helical peptides II", *Journal of Molecular Biology*, vol. 245, 1995, 275-296.

Munoz, "Helix Design, Prediction and Stability", *Current Opinion in Biotechnology* vol. 6, 1995, 382-386.

Murray, Pedro F. "Peptide Degradation: Effect of Substrate Phosphorylation on Aminopeptidasic Hydrolysis", *The International Journal of Biochemistry & Cell Biology* vol. 28, No. 4 1996, 451-456.

Nagata, Kyoto "Subsite Mapping of an Acidic Amino Acid-Specific Endopeptidase from *Streptomyces griseus*, GluSGP, and Protease V8", *J. Biochem.* 110 1991, 859-862.

Nakai, "Prediction of In-Vivo Modification Sites of Proteins from Their Primary Structures", *Journal of Biochemistry* vol. 104, 1988, 693-699.

Nishikata, M. "A Phosphotyrosine-containing Quenched Fluorogenic Peptide as a Novel Substrate for Protein Tyrosine Phosphatases", *Biochem. J.* 343 1999, 385-391.

Nishikawa, "Determination of the Specific Substrate Sequence Motifs of Protein Kinase C Isozymes", *The Journal of Biological Chemistry*, vol. 272, No. 2, Jan. 10, 1997, 952-960.

Norris, D J. "Measurement and Assignment of the Size-Dependent Optical Spectrum in CdSe Quantum Dots", *Physical Review B*. vol. 53, No. 24 1996, 16338-16346.

Onorato, "Role of Acidic Amino Acids in Peptide Substrates of the Beta-Adrenergic Receptor Kinase Rhodopsin Kinase", *Biochemistry*, vol. 30, No. 21, 1991, 5118-5125.

Osaka, "A new NEDD8-ligating system for cullin-4A", *Genes Dev.* 12(15) 1998, 2263-2268.

Park, Linda S. "Characterization of the Cell Surface Receptor for a Multi-Lineage Colony-Stimulating Factor (CSF-2alpha)*", *J. Biol. Chem.*, vol. 261, No. 1 1986, 205-210.

Patrick, "Protein kinase inhibitors for the treatment of cancer", *DDT* vol. 1, No. 8 1996, 325-330.

PCT/US06/060373, "International Search Report mailed Apr. 20, 2007".

PCT/US07/074031, "International Search Report Mailed Feb. 29, 2008".

Pearson, "Protein Kinase Phosphorylation Site Sequences and Consensus Specificity Motifs: Tabulations", *Methods in Enzymology*, vol. 200, 1991, 62-81.

Pearson, "Substrate Specificity of a Multifunctional Calmodulin-Dependent Protein Kinase", *The Journal of Biological Chemistry* vol. 260, No. 27, Nov. 25, 1985, 14471-14476.

Pennington, M. W. "Synthesis of fluorogenic interleukin-1 beta converting enzyme substrate based on resonance energy transfer", *Pep. Res* vol. 7, No. 2 1994, 72-76.

Perroy, Julie "Real-time monitoring of ubiquitination in living cells by BRET", *Nature Methods* vol. 1, No. 3 Dec. 1, 2004, 203-208.

Piccione, "Phosphatidylinositol 3-Kinase p85 SH2 Domain Specificity Defined by Direct Phosphopeptide/SH2 Domain Binding", *Biochemistry*, vol. 32, No. 13, Apr. 6, 1993, 3197-3202.

Pray, "Cell cycle regulatory E3 ubiquitin ligases as anticancer targets", *Drug Resistance Updates* 5 2002, 249-58.

Premont, "Protein kinases that phosphorylate activated G protein-coupled receptors", *The FASEB Journal* vol. 9, 1995, 175-182.

Prendergast, "Chemical and Physical Properties of Aequorin and the Green Fluorescent Protein Isolated from Aequorea forskalea", *Biochemistry* vol. 17, No. 17 1978, 3448-3453.

Przhiyalgovskaya, N. M. "Carbocyanine Dyes with an O-hydroxyaryl Substituent in the Meso Position of the Polymethine Chain", *Translated from Khimiya Geterotsiklicheskikh Soedinenii* No. 1, pp. 100-103 1988, 83-86.

Pullen, "Phosphorylation of serine-46 in HPr, a key regulatory protein in bacteria, results in stabilization of its solution structure", *Protein Science*, vol. 4, 1995, 2478-2486.

Qi, "Reconstitution of Neuronal Cdc2-like Kinase from Bacteria-expressed CdkS and an Active Fragment of the Brain-specific Activator", *The Journal of Biological Chemistry*, vol. 270, No. 18, May 5, 1995, 10847-10854.

Riddle, Steven M. "Time-resolved fluorescence resonance energy transfer kinase assays using physiological protein substrates: Applications of terbium-fluorescein and terbium-green fluorescent protein fluorescence resonance energy transfer pairs", *Analytical Biochemistry* vol. 356, No. 1 2006, 108-116.

Rodems, Steven M. "A FRET-Based Assay Platform for Ultra-high density drug Screening of protein kinases and phosphatases", *Assay and Drug Developement Technologies*, vol. 1, No. 1-1 2002, 9-19.

Ruzzene, Maria "Sequence specificity of C-0terminal Src kinase (CSK)", *Eur. J. Biochem*. vol. 246 1997, 433-439.

Sala-Newby, "Engineering a bioluminescent indicator for cyclic AMP-dependent protein kinase", *Biochem. J.*, vol. 279, 1991, 727-732.

Sandler, Stanley R. "Organic Functional Group Preparations", vol. 3, *New York: Academic Press* 1972, 5-7.

Schmid, Johannes A. "Dynamics of NF-kB and IkB studied with Green Fluorescent Protein(GFP) Fusion Proteins", *Journal of Biological Chemistry* vol. 275, No. 22 2000, 17035-17042

Schobel, Uwe "New Donor-Acceptor Pair for Fluorescent Immunoassays by Energy Transfer", *Bioconjugate Chem*. vol. 10 Oct. 9, 1999, 1107-1114.

Seethala, "A Fluorescence Polarization Competition Immunoassay for Tyrosine Kinases", *Analytical Biochemistry* 255 1998, 257-262.

Seethala, Ramakrishna "A Homogeneous Fluorescence Polarization Assay for Src-Family Tyrosine Kinases", *Analytical Biochemistry* vol. 253 1997, 210-218.

Seidah, "Pro-Protein Convertases of Subtilisin/Kexin Family", *Methods Enzymology* vol. 244, 1994, 175-189.

Selvin, Paul R. "Fluorescence Resonance Energy Transfer", *Methods in Enzymology*, vol. 246 1995, 300-334.

Selvin, Paul R. "Principles and Biophysical Application of Lanthanide-Based Probes", *Annual Review of Biophysics and Biomolecular Structure* vol. 31 2002, 275-302.

Shaw, N. E. "The Influence of Corticosteroids on Normal and Papain-Treated Articular Cartilage in the Rabbit.", *Bone Joint Surgery* vol. 55B, No. 1 1973, 197-205.

Shymko, "Logical Analysis of Timing-Dependent Receptor Signalling Specificity: Application to the Insulin Receptor Metabolic and Mitogenic Signalling Pathways", *Biochem J.* vol. 326, 1997, 463-469.

Sills, "Comparison of Assay Technologies for a Tyrosine Kinase Assay Generates Different Results in High Throughput Screening", *Journal Biomolecular Screening*, vol. 7, No. 3, 2002, 171-214.

Smith, "Purification and Kinetic Characterization of Human Cytomegalovirus Assemblin", *Methods in Enzymology*, vol. 244, 1994, 412-423.

Songyang, "A Structural Basis for Substrate Specificities of Protein Ser/Thr Kinases: Primary Sequence Preference of Casein Kinases I an II, NIMA, Phosphorylase Kinase, Calmodulin-Dependent Kinase II, CDK5, and Erk1", *Molecular and Cellular Biology*, vol. 16, No. 11, Nov. 1996, 6486-6493.

Songyang, Zhou "Catalytic specificity of protein-tyrosine kinases is critical for selective signalling", *Nature* 373 1995, 536-539.

Songyang, "Use of an oriented peptide library to determine the optimal substrates of protein kinases", *Current Biology* vol. 4, No. 11 1994, 973-982.

Sorensen, Steen B. "Fragmentation of proteins by *S. aureus* strain V8 protease", *Fed. of European Biochemical Societies* vol. 294, No. 3 1991, 195-197.

Sterk, "New Fluorescent Probes for Polarity Estimations at Different Distances from the Membrane Interface", *Journal of Fluorescence* vol. 7, No. 1, 1997, 115-118.

Stokoe, "The substrate specificity and structure of mitogen-activated protein (MAP) kinase-activated protein kinase-2", *Biochem. J.* vol. 296, 1993, 843-849.

Stryer, "Fluorescence Energy Transfer as a Spectroscopic Ruler", *Ann. Rev. Biochem.*, vol. 47, 1978, 819-846.

Suthanthiran, Manikkam "Immunosuppressants: Cellular and molecular mechanisms of action", *American Journal of Kidney Diseases* vol. 28, No. 2 1996, 159-172.

Swaminathan, "Photobleaching recovery and anisotropy decay of green fluorescent protein GFP-S65T in solution and cells: cytoplasmic viscosity probed by green fluorescent protein translational and rotational diffusion", *Biophysical Journal*, vol. 72, Apr. 1997, 1900-1907.

Szilak, "Design of a Leucine Zipper Coiled Coil Stabilized 1.4 Kcal Mol-1 by Phosphorylation of a Serine in the E Position", *The Protein Science*, vol. 6, 1997, 1273-1283.

Takakusa, "Design and Synthesis of an Enzyme-Cleavable Sensor Molecule for Phosphodiesterase Activity Based on Fluorescence Resonance Energy Transfer", *J. Am. Chem. Soc.* vol. 24, No. 8 2002, 1653-1657.

Tam, Amy "Dual roles for Ste24p in yeast a-Factor Maturation: NH2 terminal Proteolysis and COOH-terminal CAAX Processing", *The Journal of Cell Biology* vol. 142, No. 3 1998, 635-649.

Thornberry, "Interleukin-1beta Converting Enzyme", *Methods in Enzymology*, vol. 244, 1994, 615-631.

Tsien, R. Y. "FRET for studying intracellular signalling", *Trends in Cell Biology* vol. 3 1993, 242-245.

Tyagi, "Molecular Beacons: Probes that Fluoresceupon Hybridization", *Nature Biotechnology* vol. 14, Mar. 1996, 303-308.

Tyagi, Sanjay "Multicolor molecular beacons for allele discrimination", *Nature Biotechnology*, vol. 16 1998, 49-53.

U.S. Appl. No. 10/105,735, "Office Action mailed on Dec. 2, 2004".

Ulrich, "Mutual interactions between the SUMO and ubiquitin systems: a plea of no contest.", *Trends in Cell Biology* vol. 15, No. 10 2005, 525-532.

Umezawa, Y. "Methods of analysis for chemicals that promote/disrupt cellular signaling", *Anal Sci*, vol. 18 No. 5 May 2002, 503-516.

Universal Kinase and Phosphatase, "PanVera Introduces Z-LYTE", *Web page* Jul. 22, 2003.

U.S. Appl. No. 10/105,735, "Office Action mailed on Jan. 22, 2007".
U.S. Appl. No. 10/105,735, "Office Action mailed on Jun. 15, 2006".
U.S. Appl. No. 10/105,735, "Office Action mailed on Sep. 15, 2005".
U.S. Appl. No. 10/105,735, "Response to Dec. 2, 2004 Office Action filed Jun. 2, 2005".
U.S. Appl. No. 10/105,735, "Response to Jun. 15, 2006 Office Action filed Oct. 13, 2006".
U.S. Appl. No. 10/105,735, "Response to Sep. 15, 2005 Office Action filed Mar. 15, 2006".
U.S. Appl. No. 10/903,529, "Notice of Allowance mailed on Apr. 22, 2009".
U.S. Appl. No. 10/903,529, "Notice of Allowance mailed on Dec. 30, 2008".
U.S. Appl. No. 10/903,529, "Office Action mailed on Apr. 14, 2008".
U.S. Appl. No. 10/903,529, "Office Action mailed on Feb. 1, 2007".
U.S. Appl. No. 10/903,529, "Office Action mailed on May 29, 2009".
U.S. Appl. No. 10/903,529, "Office Action mailed on Sep. 12, 2007".
U.S. Appl. No. 10/903,529, "Requirement for Restriction/Election mailed on Dec. 5, 2006".
U.S. Appl. No. 10/903,529, "Response to Apr. 14, 2008 Office Action filed Oct. 14, 2008".
U.S. Appl. No. 10/903,529, "Response to Dec. 5, 2006 Office Action filed Jan. 5, 2007".
U.S. Appl. No. 10/903,529, "Response to Feb. 1, 2007 Office Action filed Aug. 1, 2007".
U.S. Appl. No. 10/903,529, "Response to Setember 12, 2007 Office Action filed Mar. 11,2008".
U.S. Appl. No. 11/485,957, "Non-Final Office Action mailed on Sep. 18, 2008".
U.S. Appl. No. 11/485,957, "Notice of Allowance mailed on May 6, 2009".

U.S. Appl. No. 11/485,957, "Notice of Allowance mailed on Nov. 24, 2009".
U.S. Appl. No. 11/485,957, "Office Action mailed on Jun. 26, 2007".
U.S. Appl. No. 11/485,957, "Requirement for Restriction/Election mailed on Feb. 7, 2007".
U.S. Appl. No. 11/485,957, "Requirement for Restriction/Election mailed on Mar. 5, 2008".
U.S. Appl. No. 11/485,957, "Response to Feb. 7, 2007 Office Action filed Apr. 9, 2007".
U.S. Appl. No. 11/485,957, "Response to Jun. 26, 2007 Office Action filed Dec. 26, 2007".
U.S. Appl. No. 11/485,957, "Response to Mar. 5, 2008 Office Action filed Jul. 7, 2008".
U.S. Appl. No. 11/485,957, "Response to Sep. 18, 2008 Office Action filed Mar. 18, 2009".
U.S. Appl. No. 11/780,059, "Office Action mailed on Dec. 22, 2010".
U.S. Appl. No. 11/780,059, "Office Action mailed on Jul. 1, 2009".
U.S. Appl. No. 11/780,059, "Office Action mailed on May 19, 2010".
U.S. Appl. No. 11/780,059, "Restriction Requirement mailed on Nov. 20, 2009".
U.S. Appl. No. 11/780,059, "Response to Jul. 1, 2009 Office Action, filed Aug. 3, 2009".
U.S. Appl. No. 11/780,059, "Response to Nov. 20, 2009 Office Action, filed Feb. 22, 2010".
U.S. Appl. No. 11/780,059, "Response to Dec. 22, 2010 Office Action, filed Jan. 24, 2011".
U.S. Appl. No. 11/780,059, "Response to May 19, 2010 Office Action, filed Nov. 19, 2010".
Van Rooijen, J. J. et al., "Glycosylation sites and site-specific glycosylation in human Tamm-Horsfall glycoprotein", *Glycobiology* vol. 9, No. 1, 1999, 21-30.
Varki, "Biological roles of oligosaccharides: All of the theories are correct", *Glycobiology* vol. 3, No. 2 1993, 97-130.
Vedvik, K. L. et al., "Increasing Information Content Using Multimode Fluorescent Assays", Url:http://www.invitrogen.com/downloads/76_2-038071.pdf Sep. 16, 2003, p. 1.
Voges, et al., "The 26S proteasome: a molecular machine designed for controlled proteolysis.", *Annul. Rev. Biochem.* 68 1999, 1015-1068.
Wang, Q. M. "Development of a conscious fluorescence assay for rhinovirus 14 3C protease using synthetic peptides", *Antiviral Chemistry & Chemotherapy* vol. 8, No. 4 1997, 303-310.
Wang, Huan-You "SRPK2: A Differentially Expressed SR Protein-specific Kinase Involved in Mediating the interaction and Localization of Pre-mRNA Splicing factors in Mammalian Cells", *The Journal of Cell Biology* vol. 140, No. 4 1998, 737-750.
Wang, "Use of a synthetic peptide as a selective substrate for glycogen synthase kinase 3", *Anal Biochem.220*(2) Aug. 1, 1994, 397-402.
Ward, "In Vitro Energy Transfer in Renilla Bioluminescence", *The Journal of Physical Chemistry*, vol. 80, No. 20, 1976, 2289-2291.
Ward, "Properties of the Coelenterate Green-Fluorescent Proteins", *Bioluminescence and Chemiluminescence* Academic Press 1981, 235-242.
Ward, "Reversible Denaturation of Aequorea Green-Fluorescent Protein: Physical Separation and Characterization of the Renatured Protein", *Biochemistry*, vol. 21, No. 19, 1982, 4535-4540.
Ward, "Spectral Perturbations of the Aequorea Green-Fluorescent Protein", *Photochem. Photobiol.*, vol. 35, 1982, 803-808.
Welchman, "Ubiquitin and ubiquitin-like proteins as multifunctional signals", *Nature Reviews Molecular Cell Biology* vol. 6 2005, 599-609.
Whisstock, "Prediction of protein function from protein sequence and structure", *Q Rev Biophys* vol. 36(3) Aug. 2003, 307-40.
Whitby, "Crystal structure of the human ubiquitin-like protein NEDD8 and interactions with ubiquitin pathway enzymes.", *J. Biol. Chem.* vol. 273, No. 52 1998, 34983-34991.
White, P. "Preparation of Phosphoerine Theonine and Tyrosine containing Peptides by the FMOC Methodology using Pre-formed Phosphoamino Acid building Blocks", *Innovations and Perspectives in Solid Phase Synthesis and Combinatorial Libraries* 4th Intl. Symp 1996, 557-560.
Wilkinson, "Protein kinase C: is its pivotal role in cellular activation over-stated?", *TiPS*, vol. 15, Feb. 1994, 53-57.
Wilkinson, "Regulation of ubiquitin-dependent processes by deubiquitinating enzymes.", *The FASEB Journal* vol. 11 1997, 1245-1256.
Wilkinson, "Synthesis and Characterization of Ubiquitin Carboxyl-Terminal Hydrolase", *Biochemistry* vol. 25, No. 21 1986, 6644-6649.
Woodgett, "Use of synthetic peptides mimicking phosphorylation sites for affinity purifications of protein-serene kinases.", *Methods in Enzymology*, vol. 200, 1991, 169-178.
Wright, "Fluorometric assay for adenosine 3',5'-cyclic monophosphate-dependent protein kinase and phosphoprotein phosphatase activities", *Proceedings of the National Academy of Sciences of the United States of America* vol. 78, No. 10, Oct. 1981, 6048-6050.
Yoshida, Aruto "Discovery of the Shortest Sequence Motif for High Level Mucin-type-P Glycosylation", *Journal of Biological Chemistry* vol. 272, No. 27 1997, 16884-16888.
Yoshimura, Akihiko "Uncoating of Influenza Virus in Endosomes", *Journal of Virology* vol. 51, No. 2 1984, 497-504.
Zaman, G. J. "Fluorescent Assays for High-Throughput Screening of Protein Kinases", *Combinatorial Chemistry & High Throughput Screening* vol. 6, No. 4 2003, 313-320.
Zarling, David A. "Mapping of Lymphocyte Surface Polypeptide Antigens by Chemical Cross-Linking with BSOCOES", *Journal of Immunology*, vol. 124, No. 2 1980, 913-920.
Zhang, Ji-Hu "A Simple Statistical Parameter for Use in Evaluation and Validation of High Throughout Screening Assays", *Journal of Biomolecular Screening* vol. 4, No. 2 1999, 67-73.
Zhang, "Atomic structure of the MAP kinase ERK2 at 2.3 A resolution", *Nature*, vol. 367, No. 24, Feb. 1994, 704-711.
Zhang, Yan "Optimization of Measurement Parameters and Performance Comparison for the Analyst(TM) GT and Analyst HT or Acquest", *Journal of the Association for Laboratory Automation* vol. 8, No. 2 2003, 71-73.
Zhang, "Protein Tyrosine Phosphatase Substrate Specificity: Size and Phosphotyrosine Positioning Requirements in Peptide Substrates", *Biochemistry*, vol. 33, No. 8, 1994, 2285-2290.
Zhang, "Substrate Specificity of CDC2 Kinase from Human HeLa Cells as Determined with Synthetic Peptides and Molecular Modeling", *Archives of Biochemistry and Biophysics*, vol. 315, No. 2, Dec. 1994, 415-424.
Zhao, "Characterization of a new substrate for protein kinase c: Assay by continuous fluorometric monitoring and high performance liquid chromatorgaphy", *Biochemical and Biophysical Research Communications* vol. 176, No. 3 1991, 1454-1461.
Zhou, "Structure of a C-Terminal alpha-Helix Cap in a Synthetic Peptide", *Journal of the American Chemical Society*, vol. 116, No. 3, 1994, 1139-1140.
U.S. Appl. No. 11/780,059, "Office Action mailed Apr. 14, 2011", 19 pgs.

| STEP 1 | TEST COMPOUND COMPOSITION/ KINASE MIXTURE ATP SOLUTION |
|---|---|

↓ INCUBATE 10μL KINASE REACTIONS AT ROOM TEMPERATURE FOR 1HR

| STEP 2 | ADD: DEVELOPMENT (PROTEASE) SOLUTION |
|---|---|

↓ INCUBATE 20μL DEVELOPMENT REACTIONS AT ROOM TEMPERATURE FOR 1HR

MEASURE FLUORESCENCE SIGNALS OF 20μL ASSAY

*FIG. 2A*

| STEP 1 | TEST COMPOUND COMPOSITION/ KINASE MIXTURE ATP SOLUTION |
|---|---|

↓ INCUBATE 10μL KINASE REACTIONS AT ROOM TEMPERATURE FOR 1HR

| STEP 2 | ADD: DEVELOPMENT (PROTEASE) SOLUTION |
|---|---|

↓ INCUBATE 15μL DEVELOPMENT REACTIONS AT ROOM TEMPERATURE FOR 1HR

| STEP 3 | ADD: STOP SOLUTION |
|---|---|

MEASURE FLUORESCENCE SIGNALS OF 20μL ASSAY

KINASE AND PHOSPHATASE ASSAYS

CROSS-REFERENCE TO RELATED APPLICATIONS

This application is a continuation of patent application Ser. No. 11/485,957, filed Jul. 14, 2006, which claims the benefit of Provisional Application No. 60/699,174 filed Jul. 14, 2005, and patent application Ser. No. 11/485,957 is also a Continuation-in-Part of patent application Ser. No. 10/903,529, filed Jul. 29, 2004, now U.S. Pat. No. 7,582,461, which claims the benefit of Provisional Application No. 60/490,771 filed Jul. 29, 2003, and patent application Ser. No. 11/485,957 is also a Continuation-in-Part of patent application Ser. No. 10/937,042, filed Sep. 9, 2004, now U.S. Pat. No. 7,619,059, which is a Continuation-in-Part of patent application Ser. No. 10/903,529, filed Jul. 29, 2004 which claims the benefit of Provisional Application No. 60/490,771 filed Jul. 29, 2003, all of which are incorporated by reference in their entirety.

BACKGROUND OF THE INVENTION

Field of the Invention

This invention relates to kinase, phosphatase and protein post-translational modification assays, and more particularly to compositions, methods, and kits useful for monitoring kinase and phosphatase activity.

One of the most important classes of intracellular activities is post-translational modification of proteins. Post-translational modification activities modify proteins within living cells to effect changes in their biological activity and/or function. Major types of protein post-translational modification include protein phosphorylation, dephosphorylation, methylation, prenylation, glycosylation, ubiquitination, sulfation, and proteolysis.

Protein modification by kinases and phosphatases is generally recognized as an important mechanism for regulating protein function. Protein kinases modify proteins by the addition of phosphate groups (phosphorylation), primarily on the amino acids tyrosine, serine, or threonine. Protein phosphatases, in contrast, act to remove these phosphate groups. Changes in the phosphorylation state of proteins can affect enzymatic activity, protein localization, and protein-protein interactions. Such changes can subsequently modulate cellular metabolism, regulation, growth, and differentiation.

Researchers have found more than 400 human diseases and disorders arising from genetic defects in protein kinases. Thus, the over 600 kinases and phosphatases encoded by the human genome represent potentially powerful targets for drugs. Current methods of measuring protein kinase activity, however, have many disadvantages, hampering the ability to rapidly screen kinases for drugs. For example, many current methods for measuring kinase activity rely on the incorporation and measurement of $^{32}P$ into the protein substrates of interest. In whole cells, this necessitates the use of high levels of radioactivity to efficiently label the cellular ATP pool and to ensure that the target protein is efficiently labeled with radioactivity. After incubation with one or more test drugs, the cells must be lysed and the protein of interest purified to determine its relative degree of phosphorylation. This method requires large numbers of cells, long preincubation times, and careful manipulation and washing steps to avoid artifactual phosphorylation or dephosphorylation. Alternative kinase assay methods, such as those based on phosphorylation-specific antibodies using ELISA-type approaches, involve the difficulty of producing antibodies that distinguish between phosphorylated and non-phosphorylated proteins.

There is thus a need for assays to monitor kinase and phosphatase enzymatic activities that are sensitive, simple to use, and adaptable to high-throughput screening methods.

BRIEF SUMMARY OF THE INVENTION

Some aspects of the invention are based on compositions of matter comprising a peptide having a motif, such as a recognition motif for a post-translational modification activity, and a detectable moiety. The compositions are surprisingly useful as sensors of post-translational modification activities, including kinase and phosphatase activities. The compositions can also be used to determine modulators of such activities. The methods described herein can also be used to determine modulators of post-translational modification activities. The invention also relates to methods of determining substrates and modulators of post-translational modification activities.

In one aspect, the invention provides compositions of matter. In some embodiments, a composition can include a peptide having a length from five to fifty amino acids. For example, the peptides can have a length from 8 to 50 amino acids, a length from 8 to 25 amino acids, or a length from 8 to 15 amino acids. Compositions can include a first detectable moiety, where the first detectable moiety is associated with the peptide, e.g., either covalently (optionally through a linker (L)) or non-covalently. Suitable linkers include GABA, diaminopentanyl, and aminohexanoyl groups.

In some embodiments, the compositions can include a second detectable moiety. Accordingly, in some compositions described herein, a first detectable moiety and a second detectable probe moiety can form a dark quenching RET pair. In other embodiments, a first detectable moiety and a second detectable moiety can form a FRET pair. In some embodiments, a first detectable moiety is 7-hydroxycoumarin-3-carboxa Blankenbeckler and a second detectable moiety is 5-FAM.

In one aspect, a peptide can contain a motif selected from AIYAA (SEQ ID NO: 1); QDYLS (SEQ ID NO: 4); EIYGV (SEQ ID NO: 7); TX$_1$YVA, where X$_1$ can be G, A, or E (SEQ ID NO: 110); EEYIQ (SEQ ID NO: 17); or DYSQV (SEQ ID NO: 20). A motif can be a recognition motif for a tyrosine kinase and can be selected from EAIYAAP (SEQ ID NO: 2); DQDYLSL (SEQ ID NO: 5); EEEYIQI (SEQ ID NO: 18); EEIYGVI (SEQ ID NO: 8); LTGYVAR (SEQ ID NO: 11); ITAYVAT (SEQ ID NO: 12); ITEYVAT (SEQ ID NO: 13); or GDYSQVL (SEQ ID NO: 21). Peptides having such recognition motifs include the following: EAEAIYAAPGDK (SEQ ID NO: 3); GDQDYLSLDK (SEQ ID NO: 6); EEEEYIQIVK (SEQ ID NO: 19); EEEIYGVIEK (SEQ ID NO: 9); GVLTGYVARRK (SEQ ID NO: 14); DDEITAYVATRK (SEQ ID NO: 15); TGIITEYVATRK (SEQ ID NO: 16); and EGDYSQVLEK (SEQ ID NO: 22).

In some embodiments, when a recognition motif for a tyrosine kinase is EAIYAAP (SEQ ID NO: 2), the tyrosine kinase can be selected from the group Abl1, Abl2, BMX, CSF1R, Csk, EPHB4, Fes/Fps, FGFR1, FGFR4, Fgr, FLT3, Fyn, Hck, IGF1R, IRKβ, ITK, Jak3, KDR, c-KIT, Lck, Lyn A, Lyn B, c-MET, Src, Src N1, Src N2, SYK, TIE2, TRKa, and YES. Alternatively, if the recognition motif for a tyrosine kinase is DQDYLSL (SEQ ID NO: 5), the tyrosine kinase can be selected from CaMKII, CDK7/CycH, CK1δ, IKKα, and IKKβ. In another embodiment, if a recognition motif for a tyrosine kinase is EEIYGVI (SEQ ID NO: 8), the tyrosine kinase can be Abl1, Abl2, BMX, CSF1R, Csk, EPHB4, Fes/

Fps, FGFR1, Fgr, FLT3, Fyn, Hck, IGF1R, IRKβ, IRTK, ITK, Jak3, KDR, c-KIT, Lck, Lyn A, Lyn B, c-MET, Src, Src N1, Src N2, SYK, TIE2, TRKa, or YES. In yet another embodiment, if a recognition motif for a tyrosine kinase is LTGYVAR (SEQ ID NO: 11), the tyrosine kinase can be CSF1R, FLT3, or c-KIT. In an additional embodiment, if a recognition motif for a tyrosine kinase is EEEYIQI (SEQ ID NO: 18), the tyrosine kinase can be EGFR, Zap-70, PDGFR, FGFR4, Abl 1, or Lyn B. In another embodiment, if a recognition motif for a tyrosine kinase is EEIYAAR (SEQ ID NO: 169), the tyrosine kinase can be selected from the group FER and TEK (TIE 2).

In another aspect, a peptide can have a motif selected from RR(S/T)L (SEQ ID NO: 145); L(S/T)TT (SEQ ID NO: 146); L(S/T)LD (SEQ ID NO: 147); $RX_1(S/T)X_2$, where $X_1$ can be V, A, or Q and $X_2$ can be V or L (SEQ ID NO: 148); TS(S/T)L (SEQ ID NO: 149); $X_1(S/T)PX_2$ where $X_1$ can be P or I and $X_2$ can be G, K, or D (SEQ ID NO: 150); $(S/T)X_1X_2VA$, where $X_1$ can be A, E, or Q and $X_2$ can be Y or H (SEQ ID NO: 151); I(S/T)IAN (SEQ ID NO: 152); SIA(S/T)I (SEQ ID NO: 153); (S/T)VPPS*P, where S* is a phosphorylated serine (SEQ ID NO: 154); $DX_1(S/T)X_2$, where $X_1$ can be A or E and $X_2$ can be I or Q (SEQ ID NO: 155); and D(S/T)QV (SEQ ID NO: 156).

In another aspect, a peptide can include a motif selected from $RRX_1(S/T)L$, where $X_1$ can be F, W, or Y (SEQ ID NO: 45); $LX_1(S/T)TT$, where $X_1$ can be F, W, or Y (SEQ ID NO: 48); $X_1L(S/T)LD$, where $X_1$ can be F, W, or Y (SEQ ID NO: 51); $RX_1X_2(S/T)X_3$, where $X_1$ can be V, A, or Q, $X_2$ can be F, W, or Y, and $X_3$ can be V or L (SEQ ID NO: 54); $TX_1S(S/T)L$, where $X_1$ can be F, W, or Y (SEQ ID NO: 61); $X_1X_2(S/T)PX_3$ where $X_1$ can be P or I, $X_2$ can be F, W, or Y, and $X_3$ can be G, K, or D (SEQ ID NO: 64); $X_1(S/T)X_2X_3VA$, where $X_1$ can be F, W, or Y, $X_2$ can be A, E, or Q, and $X_3$ can be Y or H (SEQ ID NO: 71); $IX_1(S/T)IAN$, where $X_1$ can be F, W, or Y (SEQ ID NO: 78); $SIAX_1(S/T)I$, where $X_1$ can be F, W, or Y (SEQ ID NO: 81); (S/T)VPPS*P, where S* is a phosphorylated serine (SEQ ID NO: 84); $DX_1X_2(S/T)X_3$, where $X_1$ can be A or E, $X_2$ can be F, W, or Y, and $X_3$ can be I or Q (SEQ ID NO: 87); and $DX_1(S/T)QV$, where $X_1$ can be F, W, or Y (SEQ ID NO: 92).

In certain embodiments, a motif can be selected from RRF(S/T)L (SEQ ID NO: 157); LF(S/T)TT (SEQ ID NO: 158); YL(S/T)LD (SEQ ID NO: 159); $RX_1F(S/T)X_2$, where $X_1$ can be V, A, or Q and $X_2$ can be V or L (SEQ ID NO: 160); TFS(S/T)L (SEQ ID NO: 161); $X_1F(S/T)PX_2$ where $X_1$ can be P or I and $X_2$ can be G, K, or D (SEQ ID NO: 162); $F(S/T)X_1X_2VA$, where $X_1$ can be A, E, or Q and $X_2$ can be Y or H (SEQ ID NO: 163); IF(S/T)IAN (SEQ ID NO: 164); SIAF(S/T)I (SEQ ID NO: 165); $DX_1F(S/T)X_2$, where $X_1$ can be A or E and $X_2$ can be I or Q (SEQ ID NO: 166); and DY(S/T)QV (SEQ ID NO: 167).

In another aspect, the invention provides peptides containing motifs that can be recognition motifs for serine/threonine kinases. Examples of recognition motifs for serine/threonine kinase include LRRFSLG (SEQ ID NO: 46); GLFSTTP (SEQ ID NO: 49); DYLSLDK (SEQ ID NO: 52); NRVFSVA (SEQ ID NO: 55); PRAFSVG (SEQ ID NO: 56); RRQFSLR (SEQ ID NO: 57); RTFSSLA (SEQ ID NO: 62); APFSPGG (SEQ ID NO: 65); HPFSPKK (SEQ ID NO: 66); KIFSPDV (SEQ ID NO: 67); EFTAYVA (SEQ ID NO: 72); IFTEYVA (SEQ ID NO: 73); VFTQHVA (SEQ ID NO: 74); RIFSIANS (SEQ ID NO: 79); DSIAFSIV (SEQ ID NO: 82); FSVPPS*PD, where S* is a phosphorylated serine (SEQ ID NO: 85); EDAFSII (SEQ ID NO: 88); EDEFSQN (SEQ ID NO: 89); or EGDYSQV (SEQ ID NO: 93). Peptides having such recognition motifs include the following: ALRRFS-LGEK (SEQ ID NO: 47); VAPFSPGGRAK (SEQ ID NO: 68); RGGLFSTTPGGTK (SEQ ID NO: 50); KLNRVFSVAC (SEQ ID NO: 58); GDQDYLSLDK (SEQ ID NO: 53); ARPRAFSVGK (SEQ ID NO: 59); RRRQFSLRRKAK (SEQ ID NO: 60); RPRTFSSLAEGK (SEQ ID NO: 63); AKHPFSPKKAK (SEQ ID NO: 69); DDEFTAYVATRK (SEQ ID NO: 75); TGIFTEYVATRK (SEQ ID NO: 76); TGVFTQHVATRK (SEQ ID NO: 77); QRIFSIANSIVK (SEQ ID NO: 80); RIDSIAFSIVGK (SEQ ID NO: 83); PRPFSVPPS*PDK, where S* is a phosphorylated Serine (SEQ ID NO: 86); EEDAFSIIGK (SEQ ID NO: 90); REDEFSQNEEK (SEQ ID NO: 91); IIKIFSPDVEK (SEQ ID NO: 70); and EGDYSQVLEK (SEQ ID NO: 22).

When a recognition motif for a serine/threonine kinase is LRRFSLG (SEQ ID NO: 46), the serine/threonine kinase can be selected from the group consisting of Akt1, Akt2, Akt3, Aurora A, CaMKII, CDK2/CycA, CDK3/CycE, CDK7/CycH, MAPKAP-K1α, MAPKAP-K1β, MAPKAP-K1γ, MSK1, PAK2, PKA, PKG, and ROCK. In other embodiments, when a recognition motif for a serine/threonine kinase is GLFSTTP (SEQ ID NO: 49), the serine/threonine kinase can be selected from p38γ, p38δ, and REDK. Alternatively, if a recognition motif for a serine/threonine kinase is NRVFSVA (SEQ ID NO: 55), the serine/threonine kinase can be Akt3, AMPK, CaMKII, CDK7/CycH, CHK2, IKKα, MAPKAP-K1α, MAPKAP-K2, MAPKAP-K3, MAPKAP-K5, PAK2, PKA, PKCβII, REDK, ROCK, ROCK2, or SGK1. In another embodiment, if a recognition motif for a serine/threonine kinase is PRAFSVG (SEQ ID NO: 56), the serine/threonine kinase can be selected from the group consisting of Akt1, Akt2, Akt3, CaMKII, CDK7/CycH, IKKβ, MAPKAP-K1α/RSK1, MAPKAP-K1β/RSK2, MAPKAP-K1γ/RSK3, MSK1, PAK2, PIM1, PKA, PKG, REDK, and SGK1. A recognition motif for a serine/threonine kinase can be RRQFSLR (SEQ ID NO: 57), where the serine/threonine kinase can be Akt1, Akt2, Akt3, CaMKII, CHK1, CHK2, MAPKAP-K1α, MAPKAP-K1β, MAPKAP-K1γ, MSK1, p70 S6 Kinase, PAK2, PIM1, PKA, PKCα, PKCβI, PKCβII, PKCγ, PKCδ, PKCε, PKCζ, PKCη, PKCθ, PKCι, PKG, ROCK, ROCK2, or SGK1. In another embodiment, a recognition motif for a serine/threonine kinase is RTFSSLA (SEQ ID NO: 62), and the serine/threonine kinase is selected from the group consisting of Akt1, CDK2/CycA, CDK6, IKKβ, MAPKAP-K1α, MAPKAP-K1β, MAPKAP-K1γ, p70 S6 Kinase, PAK2, and PKA. A recognition motif for a serine/threonine kinase can be APFSPGG (SEQ ID NO: 65), and the serine/threonine kinase can be selected from the group consisting of CDK2/CycA, CDK3/CycE, ERK1, ERK2, IKKα, p38β, p38γ, and p38δ.

A recognition motif for a serine/threonine kinase can be SRQFSVA (SEQ ID NO: 175), and the serine/threonine kinase can be selected from the group consisting of CAMK1D, CAMK2B, CAMK4, PRKCN(PKD3), PRKD1, and PRKD2. A recognition motif for a serine/threonine kinase can be ESFSSSE (SEQ ID NO: 178), and the serine/threonine kinase can be selected from the group consisting of CSNK1A1 (CK1), CSNK1D (CK1 delta), CSNK1E (CK1 epsilon), CSNK2A1 (CK2 alpha 1), and CSNK2A2 (CK2 alpha 2). A recognition motif for a serine/threonine kinase can be SFGSPNR (SEQ ID NO: 181), and the serine/threonine kinase can be selected from the group consisting of CDK1/cyclin B, CDK2/cyclin A, and CDK5/p35. A recognition motif for a serine/threonine kinase can be QRRYSNV (SEQ ID NO: 184), and the serine/threonine kinase can be selected from the group consisting of CDC42BPB, DAPK3, and MYLK2. A recognition motif for a serine/threonine kinase can be RRLSFAE (SEQ ID NO: 187), and the serine/threonine kinase can be selected from the group consisting of PAK1, PAK3, PAK-4, PAK6, PRKG2 (PKG2), and PRKX. A recognition motif for a serine/threonine kinase can be EPFTPSG (SEQ ID NO: 190), and the serine/threonine kinase can be MAPK11 (p38 beta). A recognition motif for a serine/threonine kinase can be IEASFAE (SEQ ID NO: 193), and the serine/threonine kinase can be selected from the group consisting of ADRBK1 (Grk2), ADRBK2 (Grk3), GRK4, GRK5, GRK6, GRK7, PLK1, PLK2 (SNK), and PLK3.

Any of the compositions described herein can include a protease cleavage site, such as a chymotrypsin protease cleavage site, a caspase 3 protease cleavage site, a cathepsin G protease cleavage site, a trypsin protease cleavage site, an elastase protease cleavage site, an endoproteinase Asp-N protease cleavage site, or an endoproteinase Glu-N protease cleavage site. In certain embodiments, the protease cleavage site can include a sequence FS, FT, or Y.

In some embodiments, a composition of the invention can exhibit a detectable property, such as an optical property, a magnetic property, or a radioactive property. For example, an optical property can be a molar extinction coefficient at an excitation wavelength, a quantum efficiency, an excitation spectrum, an emission spectrum, an excitation wavelength maximum, an emission wavelength maximum, a ratio of excitation amplitudes at two wavelengths, a ratio of emission amplitudes at two wavelengths, an excited state lifetime, an anisotropy, a polarization of emitted light, a resonance energy transfer, or a quenching of emission at a wavelength. The optical property can be a fluorescent property, e.g., a fluorescence excitation spectrum, a fluorescence emission spectrum, a fluorescence excitation wavelength maximum, a fluorescence emission wavelength maximum, a ratio of fluorescence excitation amplitudes at two wavelengths, a ratio of fluorescence emission amplitudes at two wavelengths, a fluorescence excited state lifetime, a fluorescence anisotropy, or a quenching of fluorescence emission at a wavelength. In certain embodiments, a composition can exhibit a fluorescence excitation maximum in the range from 250 to 750 nm and/or a fluorescence emission maximum in the range from 450 to 800 nm.

A detectable moiety can be, for example, a fluorescent molecule such as 5-FAM, 6-FAM, 7-hydroxycoumarin-3-carboxamide, 6-chloro-7-hydroxycoumarin-3-carboxamide, fluorescein-5-isothiocyanate, dichlorotriazinylaminofluorescein, tetramethylrhodamine-5-isothiocyanate, tetramethylrhodamine-6-isothiocyanate, succinimidyl ester of 5-carboxyfluorescein, succinimidyl ester of 6-carboxyfluorescein, 5-carboxytetramethylrhodamine, 6-carboxymethylrhodamine, and 7-amino-4-methylcoumarin-3-acetic acid. In other embodiments, a detectable moiety is a binding pair member, e.g., an epitope for an antibody or biotin. In some cases, a fluorescent molecule can be a fluorescent acceptor moiety, e.g., as described herein. In certain cases, a first or second detectable moiety can be a luminescent metal complex, e.g., as described below.

In certain cases, a first detectable moiety and a second detectable moiety can form a TR-RET pair. For example, in certain embodiments, a first detectable moiety is a fluorescent acceptor moiety, and a second detectable moiety is a luminescent metal complex. Thus, in certain embodiments, a first detectable moiety is 5-FAM, and a second detectable moiety is a luminescent terbium complex. In yet other cases, either separately or in addition to monitoring FRET or TR-RET, the polarization of fluorescent emission from first and/or second detectable moieties can be monitored.

A first detectable moiety or a second detectable moiety can be a fluorescent acceptor moiety. A fluorescent acceptor moiety can be selected from the group consisting of fluorescein, rhodamine, GFP, GFP derivatives, FITC, 5-FAM, 6-FAM, 7-hydroxycoumarin-3-carboxamide, 6-chloro-7-hydroxycoumarin-3-carboxamide, fluorescein-5-isothiocyanate, dichlorotriazinylaminofluorescein, tetramethylrhodamine-5-isothiocyanate, tetramethylrhodamine-6-isothiocyanate, succinimidyl ester of 5-carboxyfluorescein, succinimidyl ester of 6-carboxyfluorescein, 5-carboxytetramethylrhodamine, 6-carboxymethylrhodamine, and 7-amino-4-methylcoumarin-3-acetic acid.

A first or second detectable moiety can be a luminescent metal complex, which can be a lanthanide metal complex. A lanthanide metal complex can include an organic antenna moiety, a metal liganding moiety, a lanthanide metal ion, and an optional linker for conjugation to a composition or probe composition. A lanthanide metal ion can be selected from the group consisting of Sm(III), Ru(III), Eu (III), Gd(III), Tb(III), and Dy(III). An organic antenna moiety can be selected from the group consisting of: rhodamine 560, fluorescein 575, fluorescein 590, 2-quinolone, 4-quinolone, 4-trifluoromethylcoumarin (TFC), 7-diethyl-amino-coumarin-3-carbohydrazide, 7-amino-4-methyl-2-coumarin (carbostyril 124), 7-amino-4-methyl-2-coumarin (coumarin 120), 7-amino-4-trifluoromethyl-2-coumarin (coumarin 124), and aminomethyltrimethylpsoralen. A metal liganding moiety can be a metal chelating moiety selected from the group consisting of: EDTA, DTPA, TTHA, DOTA, NTA, HDTA, DTPP, EDTP, HDTP, NTP, DOTP, DO3A, DOTAGA, and NOTA.

In another aspect, the invention provides a method for characterizing a kinase. The method includes the steps of contacting a composition, e.g., as described herein, with a protein kinase under conditions effective for the protein kinase to phosphorylate the composition, and measuring the ability of the protein kinase to phosphorylate the composition.

In yet another aspect, the invention features a method for identifying a substrate of a kinase. The method includes contacting a composition described above with a protein kinase; contacting the composition and the protein kinase with a protease to form a protease mixture; and comparing a measurable property in the protease mixture with the measurable property in a control protease mixture lacking the protein kinase, the protease or both. Some methods include contacting a composition described above with a protein kinase; contacting the composition and the protein kinase with a protease to form a protease mixture; contacting the protease mixture with a probe composition as described above to form a detection mixture; and comparing a measurable property in the detection mixture with the measurable property in a control detection mixture lacking the protein kinase, the protease or both. The composition is identified as a substrate of the protein kinase if the measurable property in the protease mixture is different from the measurable property in the control protease mixture. ATP can be present during the contacting step with the kinase. In some embodiments, a measurable property in the protease mixture is compared with a measurable property in a control protease mixture lacking ATP, where the composition is identified as a substrate of the kinase if the measurable property in the protease mixture is different from the measurable property in the control protease mixture.

In some embodiments of the method, two or more different compositions are contacted independently with the protein kinase and ATP during the contacting step to form two or more kinase mixtures. Each of the kinase mixtures is contacted independently with a protease during the contacting step with the protease to form two or more protease mixtures. In some embodiments, each of the two or more protease mixtures is contacted independently with a probe composition to form two or more detection mixtures. A measurable property in each of the protease mixtures is compared with the measurable property in a corresponding control mixture. In other embodiments, two or more different protein kinases are contacted independently with the composition and the ATP during the contacting step to form two or more kinase mixtures. Each of the kinase mixtures is then contacted independently with a protease to form two or more protease mixtures, and a measurable property in each of the protease mixtures is compared with the measurable property in a corresponding control mixture.

The comparison of measurable properties can occur concurrently with the protease contacting step or after the protease contacting step. The contacting step can be completed by inhibiting a proteolytic activity of the protease, e.g., by adding a reagent to the protease mixtures or by heating the protease mixtures. The reagent can be aprotinin, PMSF, TPCK, AEBSF, chymotrypsin inhibitor 1, and chymotrypsin inhibitor 2.

The invention also provides a method for identifying a modulator of activity of a kinase. In the method, a mixture of a protein kinase, a substrate for the protein kinase, and a test compound are mixed; the mixture is contacted with a protease to form a protease mixture; and a measurable property in the protease mixture is compared to the measurable property in a control mixture of the substrate, the protein kinase, and the protease in the absence of the test compound. The test compound is identified as a modulator of activity of the kinase if the measurable property in the protease mixture is different from the measurable property in the control mixture. ATP can be present during the kinase contacting step. A substrate for a protein kinase can be a composition, e.g., as described herein.

In some embodiments, two or more different test compounds can be contacted independently with the protein kinase, ATP, and the substrate in the contacting step to form two or more kinase mixtures. Each of the kinase mixtures is contacted independently with a protease to form two or more protease mixtures, and a measurable property in each of the protease mixtures is compared with the measurable property in a corresponding control mixture. In some embodiments, each of the kinase mixtures is contacted independently with a protease to form two or more protease mixtures; the two or more protease mixtures are contacted independently with a probe composition to form two or more detection mixtures; and a measurable property in each of the detection mixtures is compared with the measurable property in a corresponding control mixture. In other embodiments, two or more different protein kinases are contacted independently with ATP, the test compound, and the substrate to form two or more kinase mixtures; each of the kinase mixtures is contacted independently with a protease to form two or more protease mixtures; and a measurable property in each of the protease mixtures is compared with the measurable property in a corresponding control mixture. The comparison step can occur during or after the protease contacting step. The protease contacting step may be completed as e.g., described herein.

In another aspect, the invention provides phosphorylated compositions of matter. Such compositions of matter can be useful as substrates for phosphatases. For example, a Y or an S/T in a motif described above may be phosphorylated, e.g., chemically or enzymatically. In other embodiments, a Y or an S/T in a recognition motif for a tyrosine kinase or a S/T kinase, respectively, may be phosphorylated to result in a recognition motif for a protein phosphatase. Examples of a protein phosphatase recognition motif include LRRFS*LG (SEQ ID NO: 96); GLFS*TTP (SEQ ID NO: 99); DYLS*LDK (SEQ ID NO: 102); NRVFS*VA (SEQ ID NO: 105); PRAFS*VG (SEQ ID NO: 106); RRQFS*LR (SEQ ID NO: 107); RTFSS*LA (SEQ ID NO: 112); APFS*PGG (SEQ ID NO: 115); HPFS*PKK (SEQ ID NO: 116); KIFS*PDV (SEQ ID NO: 117); EFT*AYVA (SEQ ID NO: 122); IFT*EYVA (SEQ ID NO: 123); VFT*QHVA (SEQ ID NO: 124); RIFS*IANS (SEQ ID NO: 129); DSIAFS*IV (SEQ ID NO: 132); FS*VPPS*PD (SEQ ID NO: 135); EDAFS*II (SEQ ID NO: 138); EDEFS*QN (SEQ ID NO: 139), and EGDYS*QV (SEQ ID NO: 143), where S* represents a phosphorylated serine and T* represents a phosphorylated threonine.

Examples of peptides comprising phosphatase recognition motifs include EAEAIY*AAPGDK (SEQ ID NO: 25); GDQDY*LSLDK (SEQ ID NO: 28); EEEEY*IQIVK (SEQ ID NO: 41); EEEIY*GVIEK (SEQ ID NO: 31); GVLTGY*VARRK (SEQ ID NO: 36); DDEITAY*VATRK (SEQ ID NO: 37); TGIITEY*VATRK (SEQ ID NO: 38), and EGDY*SQVLEK (SEQ ID NO: 44), where Y* represents a phosphorylated tyrosine. In other embodiments, a peptide comprising a phosphatase recognition motif has a sequence selected from ALRRFS*LGEK (SEQ ID NO: 97); VAPFS*PGGRAK (SEQ ID NO: 118); RGGLFS*TTPGGTK (SEQ ID NO: 100); KLNRVFS*VAC (SEQ ID NO: 108); GDQDYLS*LDK (SEQ ID NO: 103); ARPRAFS*VGK (SEQ ID NO: 109); RRRQFS*LRRKAK (SEQ ID NO: 110); RPRTFSS*LAEGK (SEQ ID NO: 113); AKHPFS*PKKAK (SEQ ID NO: 119); DDEFT*AYVATRK (SEQ ID NO: 125); TGIFT*EYVATRK (SEQ ID NO: 126); TGVFT*QHVATRK (SEQ ID NO: 127); QRIFS*IANSIVK (SEQ ID NO: 130); RIDSIAFS*IVGK (SEQ ID NO: 133); PRPFS*VPPS*PDK (SEQ ID NO: 136); EEDAFS*IIGK (SEQ ID NO: 140); REDEFS*QNEEK (SEQ ID NO: 141); IIKIFS*PDVEK (SEQ ID NO: 120), and EGDYS*QVLEK (SEQ ID NO: 144).

In certain embodiments, a phosphatase recognition motif is EAIY*AAP (SEQ ID NO:24), and the phosphatase is selected from the group consisting of PTP1B, LAR, and LCA. Alternatively, a phosphatase recognition motif can be DQDYLS*L (SEQ ID NO: 27), and the phosphatase can be PP1α, PP2A, PP2B, or PP2C. In other embodiments, a phosphatase recognition motif is LRRFS*LG (SEQ ID NO: 96), and the phosphatase is selected from the group consisting of PP1α, PP2A, and PP2C. In yet other embodiments, a phosphatase recognition motif is GLFS*TTP (SEQ ID NO: 99), and the phosphatase is selected from PP1α, PP2A, PP2B, or PP2C. Additionally, a phosphatase recognition motif can be NRVFS*VA (SEQ ID NO: 105), and the phosphatase can be PP1α, PP2A, PP2B, or PP2C; a phosphatase recognition motif can be PRAFS*VG (SEQ ID NO: 106), with the phosphatase selected from the group consisting of PP1α, PP2A, and PP2B; the phosphatase recognition motif can be RRQFS*LR, (SEQ ID NO: 107) and the phosphatase can be PP1α, PP2A, or PP2B; a phosphatase recognition motif can be RTFSS*LA (SEQ ID NO: 112), and the phosphatase can be PP1α, PP2A, or PP2B; a phosphatase recognition motif can be APFS*PGG (SEQ ID NO: 115), and the phosphatase can be PP1α or PP2A; a phosphatase recognition motif can be EEIY*GVI (SEQ ID NO: 30), and the phosphatase can be PTP1B, LAR, or LCA; or the phosphatase recognition motif can be LTGY*VAR (SEQ ID NO: 33), and the phosphatase can be PTP1B, LAR, or LCA.

In an additional aspect, the invention provides a method for characterizing a phosphatase. The method includes contacting a composition described above (e.g., a phosphorylated composition) with a protein phosphatase under conditions effective for the protein phosphatase to dephosphorylate the composition, and measuring the ability of the protein phosphatase to dephosphorylate the composition.

The invention also provides a method for identifying a substrate of a phosphatase, which includes contacting a composition described above with a protein phosphatase; contacting the composition and the protein phosphatase with a protease to form a protease mixture; and comparing a measurable property in the protease mixture with a measurable property in a control protease mixture lacking phosphatase, where the composition is identified as a substrate of the phosphatase if the measurable property in the protease mixture is different from the measurable property in the control protease mixture.

In certain embodiments, two or more different compositions are contacted independently with the phosphatase to form two or more phosphatase mixture; each of the phosphatase mixtures is contacted independently with a protease to form two or more protease mixtures; and a measurable property in each of the protease mixtures is compared with the measurable property in a corresponding control mixture. In other embodiments, two or more different phosphatases are contacted independently with the composition; each of the phosphatase mixtures is contacted independently with a protease to form two or more protease mixtures; and a measurable property in each of the protease mixtures is compared with the measurable property in a corresponding control mixture.

The invention also provides a method for identifying a modulator of activity of a phosphatase, including contacting a mixture of a protein phosphatase, a substrate for the protein phosphatase, and a test compound to form a phosphatase mixture; contacting the phosphatase mixture with a protease to form a protease mixture; and comparing a measurable property in the protease mixture to the measurable property in a control protease mixture lacking the test compound, where the test compound is identified as a modulator of activity of the phosphatase if the measurable property in the protease mixture is different from the measurable property in the control mixture. In certain embodiments, two or more different test compounds may be contacted independently with the phosphatase and the substrate to form two or more phosphatase mixtures; each of the phosphatase mixtures may be contacted independently with a protease to form two or more protease mixtures; and a measurable property in each of the protease mixtures may be compared with the measurable property in a corresponding control mixture. In other embodiments, two or more different phosphatases are contacted independently with the test compound and the substrate to form two or more phosphatase mixtures; each of the phosphatase mixtures is contacted independently with a protease to form two or more protease mixtures; and a measurable property in each of the protease mixtures is compared with the measurable property in a corresponding control mixture.

In an additional aspect, the invention provides articles of manufacture. An article of manufacture can include packaging matter and a composition of matter described herein associated with the packaging material. The article can further comprise a protein kinase or a protein phosphatase; a protease; ATP; and/or buffers.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS/FIGURES

FIG. 1 is a schematic indicating the effect on a fluorescence signal of differential sensitivity of a composition to a protease. In the Kinase Reaction, a substrate for a kinase (e.g., a composition of matter according to the present invention) is phosphorylated by the kinase. As is shown, the substrate in both the unphosphorylated and phosphorylated states exhibits FRET between the donor and acceptor fluorophores on the N- and C-termini of the substrate. In the Development (Protease) Reaction, the phosphorylated and unphosphorylated substrates are exposed to a protease, which differentially cleaves the unphosphorylated substrate relative to the phosphorylated substrate. As shown in the Detection panel, cleavage of the unphosphorylated substrate disrupts FRET between the donor and acceptor fluorophores, and results in a measurable change in the ratio of the donor fluorescence emission value relative to the acceptor fluorescence emission value.

FIG. 2 is a flow chart for identifying modulators of the activity of a Tyrosine (FIG. 2A) or Serine/Threonine (FIG. 2B) kinase.

Figure 4:
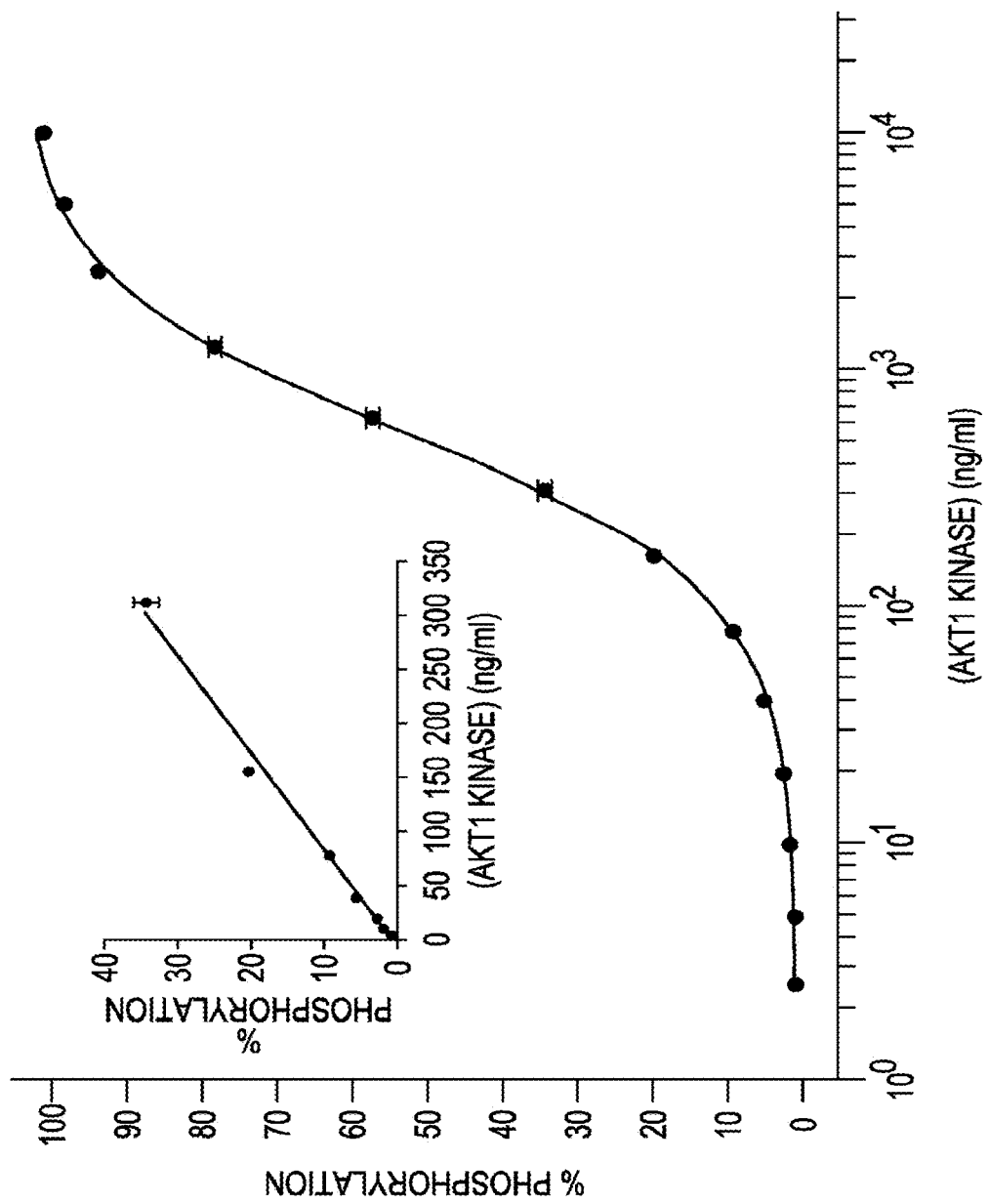

FIG. 4 demonstrates the dependence of % phosphorylation on Akt 1 kinase concentration.

Figure 5:
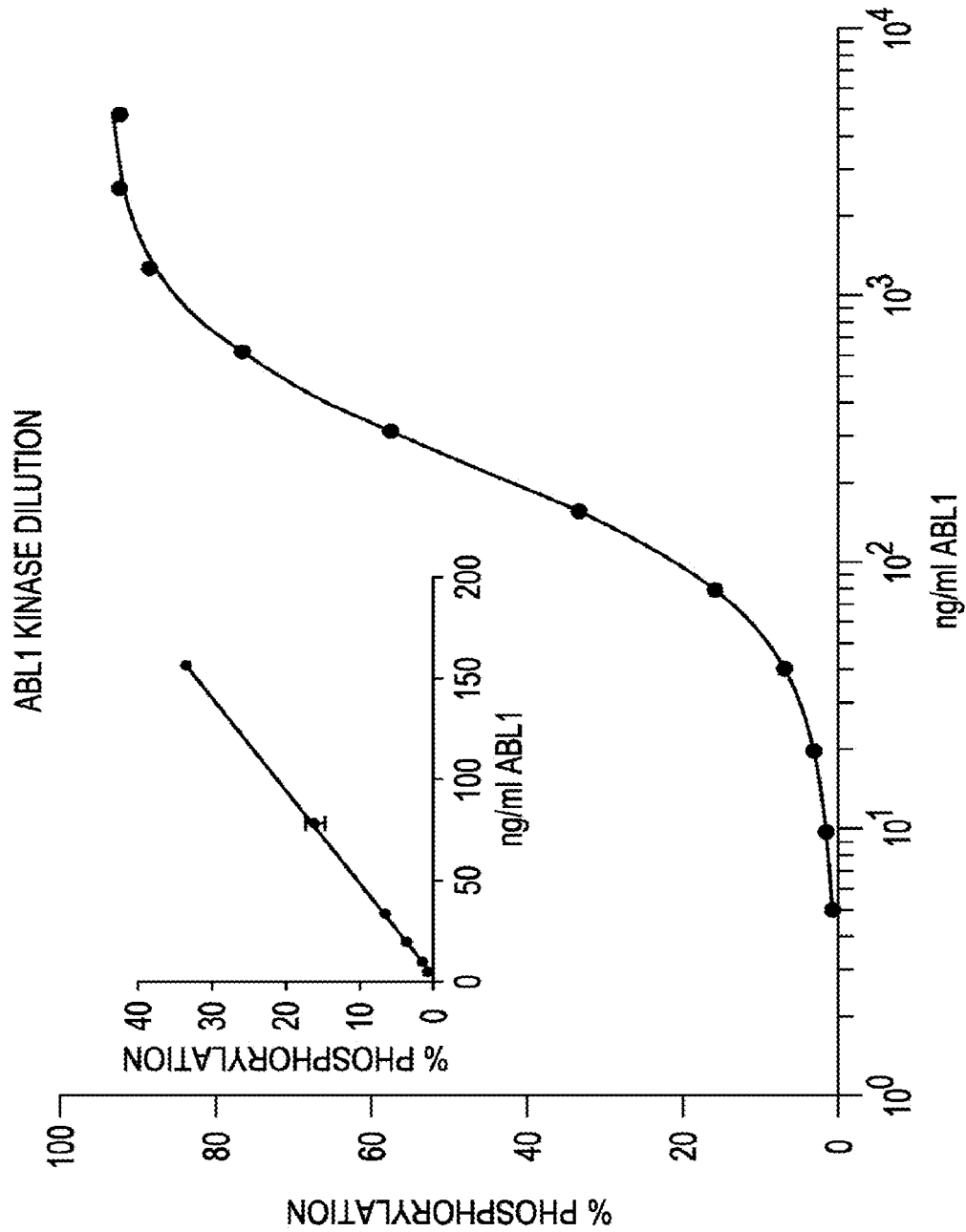

FIG. 5 demonstrates the dependence of % phosphorylation on Abl 1 kinase concentration.

Figure 6:
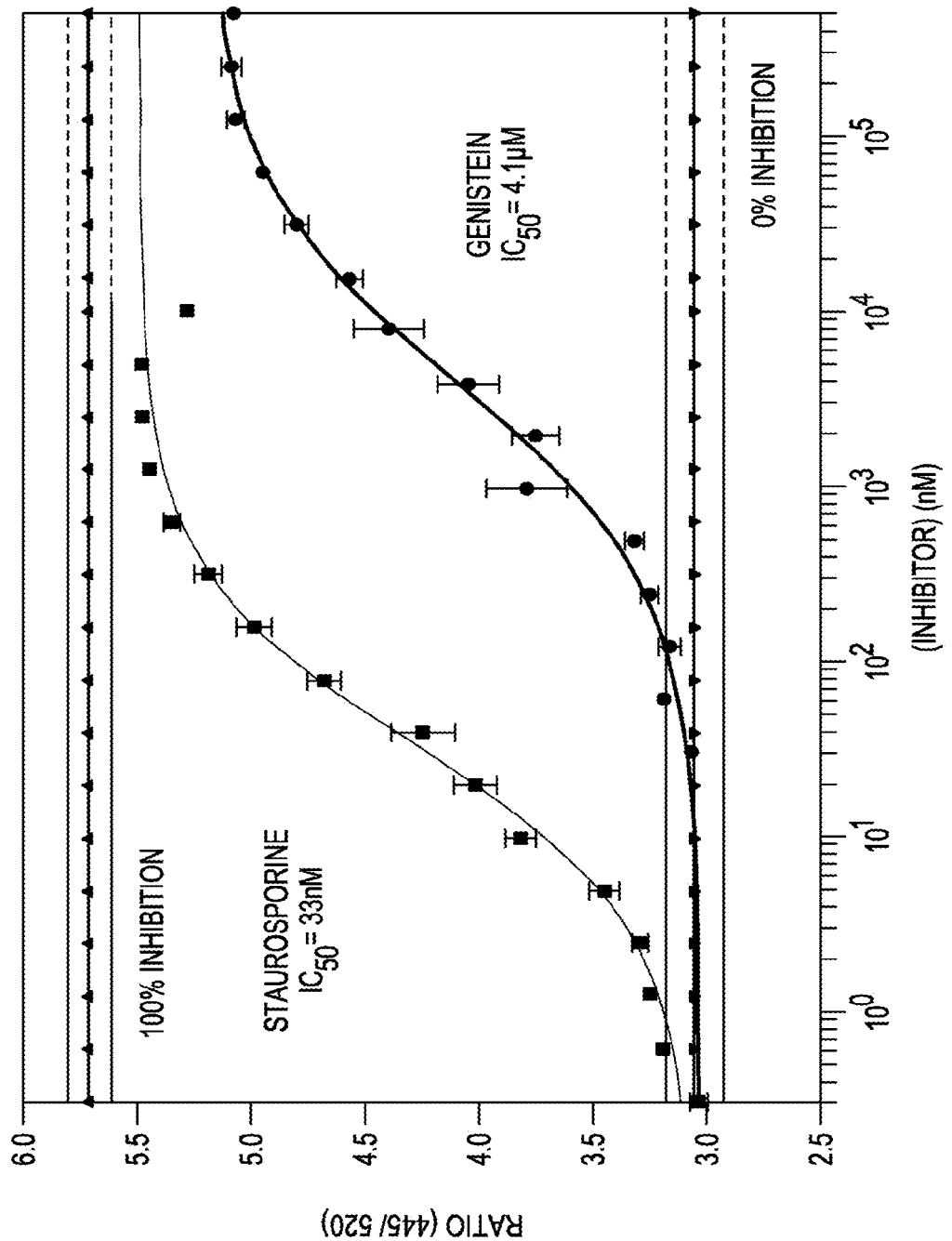

FIG. 6 demonstrates dose-dependent inhibition of Abl 1 kinase.

Figure 7:
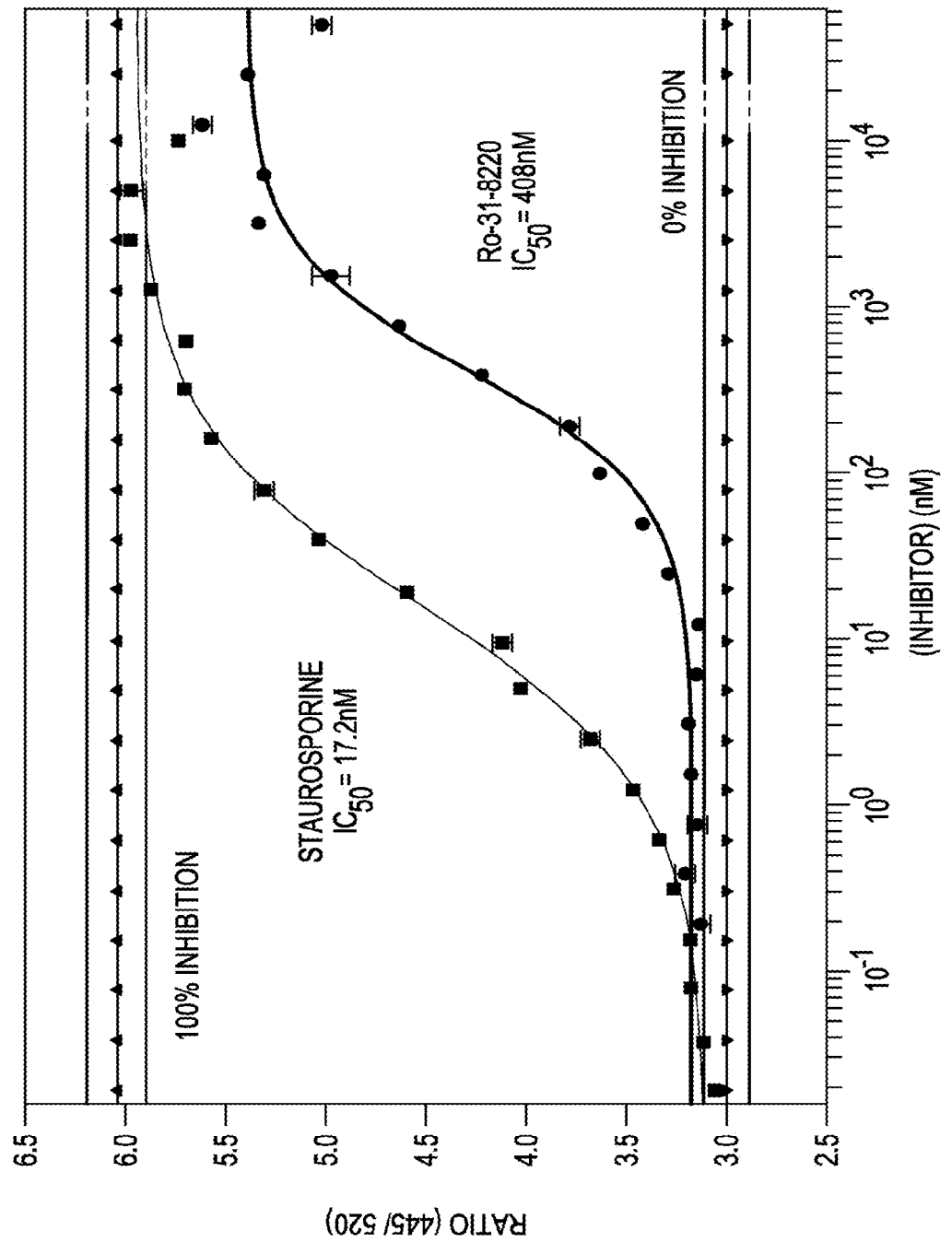

FIG. 7 demonstrates dose-dependent inhibition of Akt 1 kinase.

Figure 8:
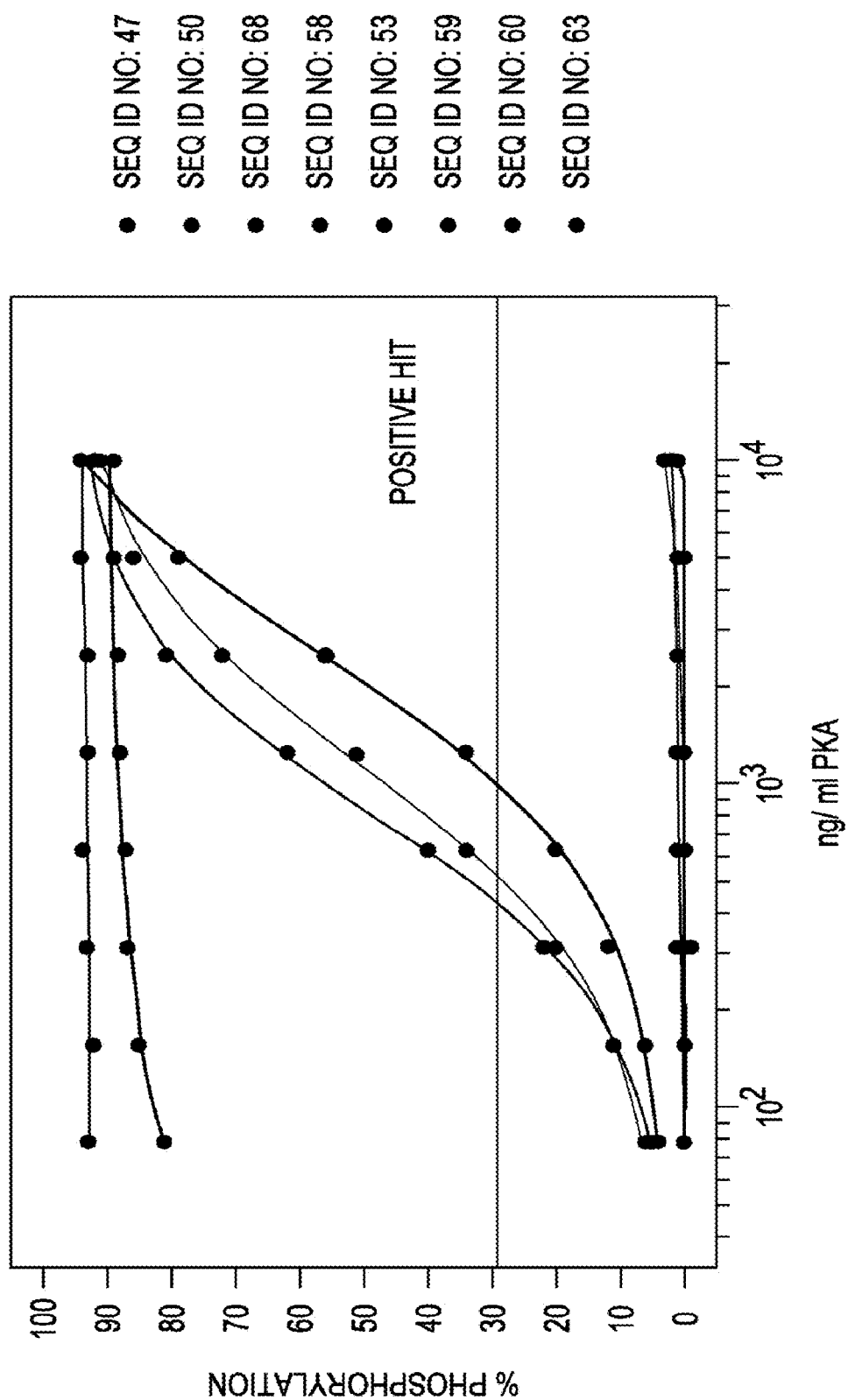

FIG. 8 demonstrates % phosphorylation data with varying concentrations of PKA kinase.

Figure 9:
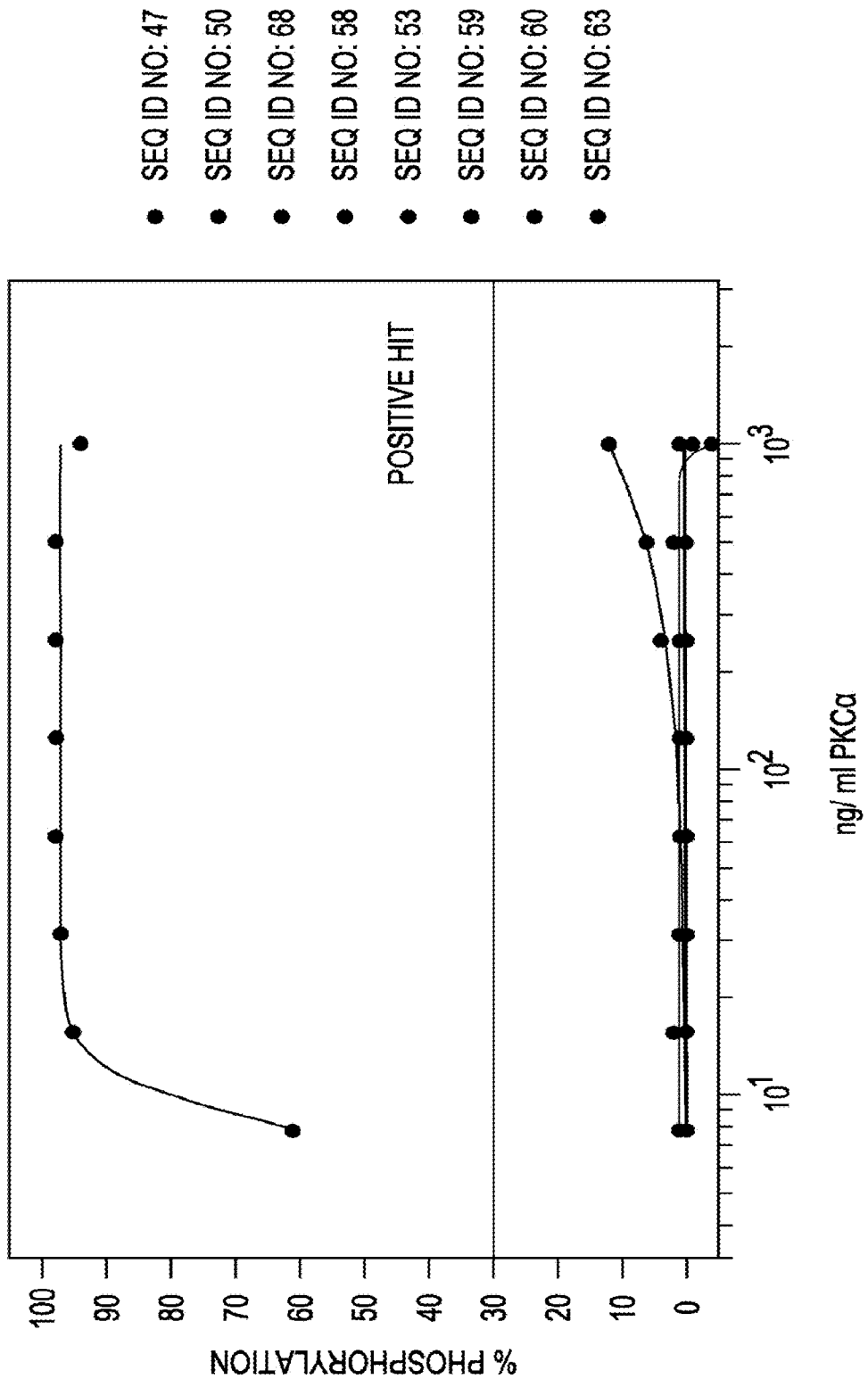

FIG. 9 demonstrates % phosphorylation data with varying concentrations of PKCα.

DETAILED DESCRIPTION OF THE INVENTION

Figure 1:
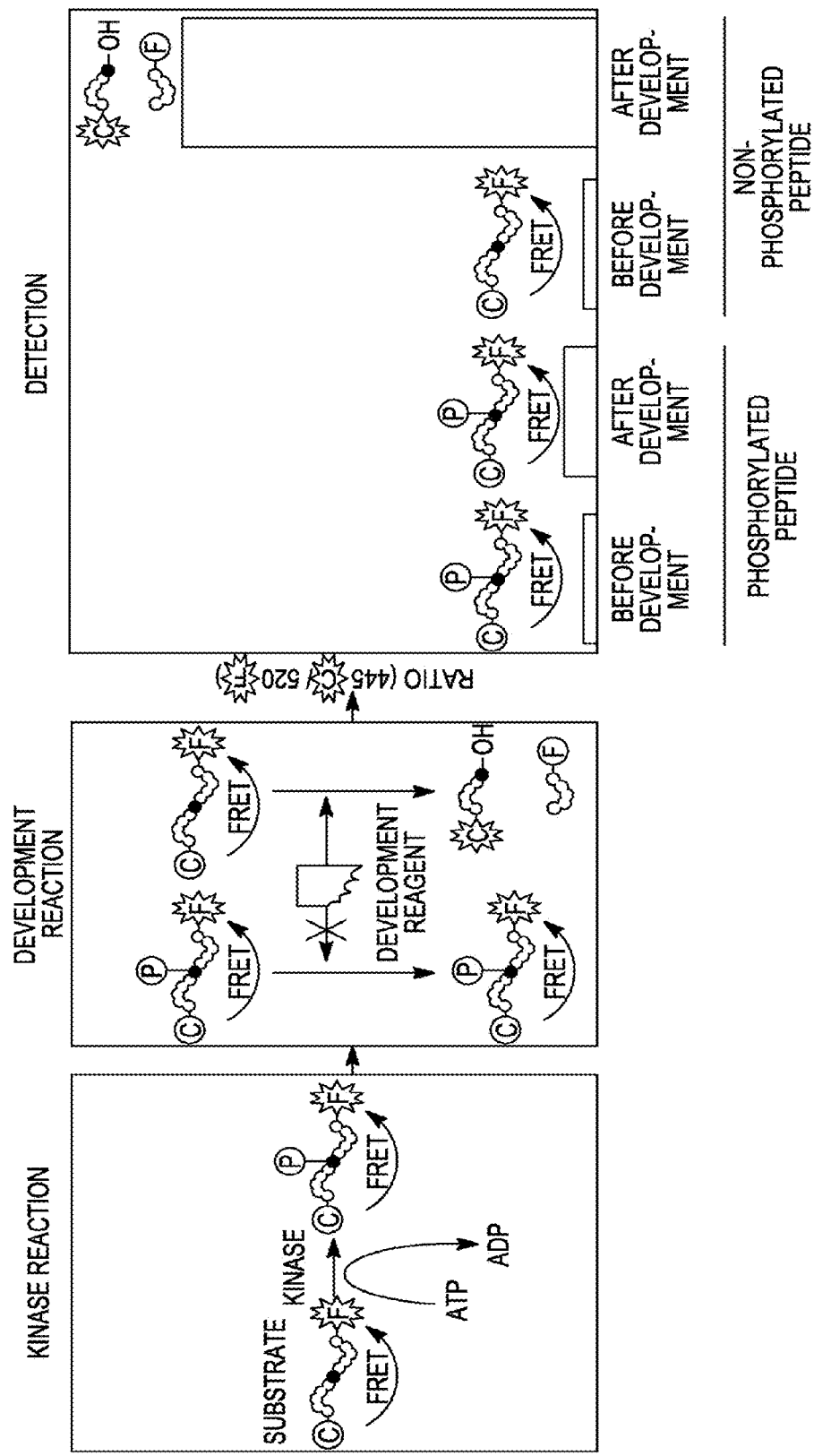

The present invention is based in part on the finding that compositions of matter that include peptides and detectable moieties can be designed to act as sensors of post-translational modification activities, including kinase or phosphatase activity. Post-translational modification of a composition containing a peptide results in a modulation of the rate and efficiency of cleavage of the modified peptide by a protease as compared to the non-modified peptide. The attachment of at least one detectable moiety to the peptide in the composition couples the cleavage of the peptide in the composition to a change in a detectable property of the composition that can be used to monitor post-translational activity in a sample and to assay for modulators of a post-translational activity, e.g., see FIG. 1.

Compositions of the present invention can be used in assay methods, particularly methods for high-throughput and miniaturized screening systems for drug discovery and profiling. In addition, methods and kits described herein typically exhibit a large dynamic range, high Z'-factor values, and increased sensitivity by employing a ratiometric analysis to eliminate well-to-well variations. Finally, methods of the present invention can be performed under near initial velocity conditions and produce accurate $IC_{50}$ data for kinase and phosphatase inhibitors.

Definitions

Generally, the nomenclature used herein and many of the fluorescence, computer, detection, chemistry, and laboratory procedures described herein are commonly employed in the art.

Abbreviations: t-Boc, tert-butyloxycarbonyl; Bzl, benzyl; CaMK, calmodulin dependent kinase; CKI, casein kinase 1; PDGF, platelet derived growth factor; Fmoc, fluorenylmethyloxycarbonyl; EGF, epidermal growth factor; ELISA, enzyme-linked immuno absorbant assay; FGF, fibroblast growth factor; HF, hydrogen fluoride; HOBT, N-Hydroxybenzotriazole; PyBop, Benzotriazole-I-yl-oxy-tris-pyyrolidino-phosphonium hexafluorophosphate; TFA, trifluoroacteic acid; FITC, fluorescein isothiocyanate; RET, resonance energy transfer; FRET, fluorescence resonance energy transfer; FAM, carboxyfluorescein.

As employed throughout the disclosure, the following terms, unless otherwise indicated, shall be understood to have the following meanings:

The term "RET" means resonance energy transfer, and refers to the radiationless transmission of an energy quantum from its site of absorption to the site of its utilization in a molecule, or system of molecules, by resonance interaction between chromophores, over distances considerably greater than interatomic, without substantial conversion to thermal energy, and without the donor and acceptor coming into kinetic collision. A donor is a moiety that initially absorbs energy (e.g., optical energy), and an acceptor is the moiety to which the energy is subsequently transferred. Fluorescence resonance energy transfer (FRET) and time-resolved fluorescence resonance energy transfer (TR-FRET) are types of RET.

The term "acceptor" refers to a chemical or biological moiety that operates via resonance energy transfer, e.g., a quencher. In RET applications, acceptors may re-emit energy transferred from a donor fluorescent moiety as fluorescence (e.g., FRET) and are "acceptor fluorescent moieties." As used herein, such a donor fluorescent moiety and an acceptor fluorescent moiety are referred to as a "FRET pair." Examples of acceptors include coumarins and related fluorophores; xanthenes such as fluoresceins; fluorescent proteins; rhodols, and rhodamines; resorufins; cyanines; difluoroboradiazaindacenes; and phthalocyanines. In other RET applications, acceptors generally do not re-emit the transferred energy and are sometimes referred to as "dark quenchers." A fluorescent donor moiety and a dark quenching acceptor moiety may be referred to herein as a "dark quenching RET pair." Examples of dark quenchers include indigos; benzoquinones; anthraquinones; azo compounds; nitro compounds; indoanilines; and di- and triphenylmethanes.

The term "quencher" refers to a molecule or part of a compound that is capable of reducing light emission (e.g. fluorescence emission) from a detectable moiety. Such reduction includes reducing the emission of light after the time when a photon is normally emitted from a fluorescent moiety. Quenching may occur by any of several mechanisms, including resonance energy transfer (RET), fluorescence resonance energy transfer (FRET), photo-induced electron transfer, paramagnetic enhancement of intersystem crossing, Dexter exchange coupling, dark quenching, and excitation coupling (e.g., the formation of dark complexes). Preferred quenchers include those that operate by RET, particularly FRET.

The term "bead" refers to a substantially spherical particle such as a sphere or microsphere. Beads may be used within a wide size range. Preferred beads are typically within the range of 0.01 to 100 µm in diameter. Beads may be composed of any material and may comprise fluorescent, luminescent, electro-luminescent, chemo-luminescent, magnetic, or paramagnetic probes. Such beads are commercially available from a variety of sources including Molecular Probes, Sigma, and Polysciences.

The terms "cleavage site," "protease cleavage site," and "protease site" are used interchangeably and refer to an amide bond that can be cleaved by a protease and one or more amino acids on either side of the bond. The designations "$P_1$", "$P_2$", "$P_3$" etc. refer to the amino acid positions 1 amino acid, 2 amino acids and 3 amino acids N-terminal to the bond. The designations "$P'_1$", "$P'_2$", "$P'_3$" etc. refer to the amino acids positions 1 amino acid, 2 amino acids and 3 amino acids C-terminal to the bond, as shown below:

Protease cleavage site
↓
$P_3\ P_2\ P_1\text{—}P'_1\ P'_2\ P'_3$

The term "detectable moiety" refers to a chemical moiety useful as a marker, indicator, or contrast agent. A detectable moiety may be capable of being detected by absorption spectroscopy, luminescence spectroscopy, fluorescence spectroscopy, magnetic resonance spectroscopy (e.g., MRI), or radioisotope detection. The term "fluorescent moiety" refers to a detectable moiety that can absorb electromagnetic energy and is capable of at least partially re-emitting some fraction of that energy as electromagnetic radiation. Suitable fluorescent moieties include, but are not limited to, coumarins and related dyes, xanthene dyes such as fluoresceins, rhodols, and rhodamines, resorufins, cyanine dyes, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, semiconductor fluorescent nanocrystals, fluorescent proteins, and fluorescent europium and terbium complexes and related compounds. In some embodiments, a detectable moiety can be a member of a specific binding pair, or can be associated (e.g., covalently) with a member of a specific binding pair. Specific binding pairs are pairs of molecules that are capable of specific interaction with one another, e.g., have an affinity for one another. For example, a specific binding pair can be ligand-protein binding pairs, e.g., enzyme-substrate, biotin-streptavidin, or epitope-antibody binding pairs. A binding pair that includes a detectable moiety has a larger apparent size than a corresponding binding pair that does not include a detectable moiety, and a larger apparent size than either member of the binding pair alone. Complexes of binding pairs can be detected by a method described herein or by other methods known to those of skill in the art, e.g., in an immunoassay format, a gel shift assay, or a chromatographic assay.

The term "motif" refers to an amino acid sequence at least five amino acids in length. In some embodiments, a motif can be a "recognition motif" for a phosphatase or a kinase, i.e., an amino acid sequence that is effective as a substrate for a protein phosphatase or protein kinase. In some embodiments, a recognition motif may be modified from a naturally existing sequence by at least one amino acid substitution. In some embodiments, the affinity (apparent $K_d$) of a kinase or phosphatase for a recognition motif is about 1 mM or less, or about 10 µM or less, or about 1 µM or less, or about 0.1 µM or less.

A recognition motif need not be an optimal or preferred recognition motif, but encompasses sequences whose phosphorylation by a kinase can be detected or whose de-phosphorylation by a phosphatase can be detected. In some embodiments, a recognition motif overlaps with or encompasses a protease cleavage site. In other embodiments, a protease cleavage site does not overlap or encompass a recognition motif.

The term "modulates" refers to partial or complete enhancement or inhibition of an activity or process (e.g., by attenuation of rate or efficiency).

The term "modulator" refers to a chemical compound (naturally occurring or non-naturally occurring), such as a biological macromolecule (e.g., nucleic acid, protein, peptide, hormone, polysaccharide, lipid), an organic molecule, or an extract made from biological materials such as bacteria, plants, fungi, or animal (particularly mammalian, including human) cells or tissues. Modulators may be evaluated for potential activity as inhibitors or enhancers (directly or indirectly) of a biological process or processes (e.g., agonist, partial antagonist, partial agonist, inverse agonist, antagonist, antineoplastic agents, cytotoxic agents, inhibitors of neoplastic transformation or cell proliferation, cell proliferation-promoting agents, and the like) by inclusion in screening assays described herein. The activity of a modulator may be known, unknown, or partially known.

The term "non-naturally occurring" refers to the fact that an object, compound, or chemical cannot be found in nature. For example, a peptide or polynucleotide that is present in an organism (including viruses) that can be isolated from a source in nature and which has not been intentionally modified by man in the laboratory is naturally-occurring, while such a peptide or polynucleotide that has been intentionally modified by man is non-naturally occurring.

The term "optical property" refers to a property of a composition, compound, or moiety and can be any one of the following: a molar extinction coefficient at an appropriate excitation wavelength, a fluorescent or luminescent quantum efficiency, a shape of an excitation spectrum or emission spectrum, an excitation wavelength maximum or emission wavelength maximum, a ratio of excitation amplitudes at two different wavelengths, a ratio of emission amplitudes at two different wavelengths, an excited state lifetime, a fluorescent anisotropy, or any other measurable optical property derived from the composition, compound, or moiety, either spontaneously or in response to electromagnetic, electrical, or chemical stimulation or reaction. One type of optical property is a fluorescent property, which refers to an optical property that can be detected using fluorescence-based techniques. The fluorescent property can be any one of the following: a molar extinction coefficient at an appropriate excitation wavelength, a fluorescent quantum efficiency, a shape of an excitation or emission spectrum, an excitation wavelength maximum, an emission magnitude at any wavelength during or at one or more times after excitation of a fluorescent moiety, a ratio of excitation amplitudes at two different wavelengths, a ratio of emission amplitudes at two different wavelengths, an excited state lifetime, a fluorescent anisotropy, or any other measurable property of a fluorescent moiety. In some embodiments, a fluorescent property refers to fluorescence emission or the fluorescence emission ratio at two or more wavelengths.

The term "peptide" refers to a polymer of two or more amino acids joined together through amide bonds. Amino acids may be natural or unnatural amino acids, including, for example, beta-alanine, phenylglycine, and homoarginine. For a review, see Spatola, A. F., in *Chemistry and Biochemistry of Amino Acids, Peptides and Proteins*, B. Weinstein, eds., Marcel Dekker, New York, p. 267 (1983). All of the amino acids used in the present invention may be either the D- or L-isomer. Chemically modified or substituted amino acids including phosphorylated (e.g., phospho-serine (phosphorylated at the hydroxyl of the side chain), phospho-tyrosine (phosphorylated at the OH of the side-chain phenyl ring), and phospho-threonine (phosphorylated at the hydroxyl of the size chain)), sulfated, methylated, or prenylated amino acids can also be used to create peptides for specific applications.

The terms "post-translational modification" and "post-translational type modification" are used interchangeably and refer to enzymatic or non-enzymatic modification of one or more amino acid residues in a peptide. Typical modifications include phosphorylation, dephosphorylation, glycosylation, methylation, sulfation, ubiquitination, prenylation, and ADP-ribosoylation. Preferred post-translational type modifications include phosphorylation and dephosphorylation. The term post-translational modification includes non-covalent type modifications that may affect protein activity, structure, or function, such as protein-protein interactions or the binding of allosteric modulators, other modulators, or second messengers such as calcium, cAMP, or inositol phosphates to the motif, recognition motif, or peptide.

The term "test compound" refers to a compound to be tested by one or more screening method(s) of the invention, e.g., to determine if it is a putative modulator of a kinase or phosphatase. A test compound can be any chemical, such as an inorganic chemical, an organic chemical, a protein, a peptide, a carbohydrate, a lipid, or a combination thereof. Typically, various predetermined concentrations (e.g., various dilutions) of test compounds are used for screening, such as 0.01 micromolar, 1 micromolar, and 10 micromolar. Test compound controls can include the measurement of a signal in the absence of the test compound or a comparison to a compound known to modulate the target activity.

Compositions

Compositions of the present invention include a peptide. Peptides of the invention can have a length from five to fifty amino acids and can include one or more motifs. Typically, a motif is five amino acids or longer in length. A motif can be a recognition motif, e.g., for a tyrosine kinase, a serine/threonine kinase, or a phosphatase. Compositions of the present invention can include a first detectable moiety, and in some embodiments, a second detectable moiety. Compositions of the present invention can include a protease cleavage site.

Kinases and Phosphatases

In general, protein kinases act on peptides by adding a phosphate group to a free hydroxyl group on an amino acid (a process known as phosphorylation), primarily on the amino acids tyrosine, serine, or threonine. The protein kinases that enzymatically catalyze these reactions may be classified into a number of distinct families based on structural and functional properties. Kinases within a family may have a similar overall topology, similar modes of regulation, and/or similar substrate specificities (e.g., see Table 1 of U.S. Pat. No. 6,410, 255). For example, members of the AGC (protein kinase A, G or C) families of kinases may prefer phosphorylation recognition motifs with basic amino acids (e.g., R or K), while those in the CMGC group may prefer proline containing motifs.

Another family of kinases are the Serine/Threonine kinases, which phosphorylate serine or threonine amino acids, and Tyrosine kinases, which phosphorylate tyrosine amino acids.

Serine/Threonine (S/T) kinases suitable for use in the present invention include, without limitation, the following:

Akt1, Akt2, Akt3, Aurora A, BARK/GRK2, CaMKII, CaMKIIa, CDK1/Cyc B, CDK2/CycA, CDK4/CAK, CDK3/CycE, CDK6/CAK, CDK7/CycH, CK1δ, CKIIα, MAP-KAP-K1α, MAPKAP-K1β, MAPKAP-K1γ, MSK1, PAK2, PKA, PKG, ROCK, ROCK2, ERK1, ERK2, ERK5, GSK-3α, MLCK, mTOR, NEK2, IKKα, IKKβ, p38β, p38γ, p38δ, REDK, AMPK, MAPKAP-K2, MAPKAP-K3, MAPKAP-K5, SGK1, PIM1, CHK1, CHK2, PKCα, PKCβI, PKCβII, PKCγ, PKCδ, PKCε, PKCζ, PKCη, PKCθ, PKCι, Raf-1, and p70 S6 Kinase.

Tyrosine kinases suitable for use in the present invention include, without limitation, the following: Abl1, Abl2, BMX, Brk, CSF1R, Csk, Erb-B2, EGFR, EphB4, Fes/Fps, FGFR1, FGFR3, FGFR4, Fgr, FLT3, Fyn, FynT, HCK, Hyl, IGF1R, IRKβ, ITK, Jak3, KDR, c-KIT, Lck, Lyn A, Lyn B, c-MET, Src, Src N1, Src N2, SYK, Tec, TIE2, TRKA, VEGFR-1/Flt, YES, and IRTK. Tyrosine kinases characterized as receptor tyrosine kinases, and that are also suitable, include EGFR, EphB4, Erb-B2, FGFR1, FGFR3, FGFR4, FLT3/FLT2, FMS/CSFR1, IGF1R, KDR, c-KIT, c-MET, TIE2, TRKA, and VEGFR-1/Flt. Tyrosine protein kinases characterized as soluble tyrosine protein kinases are also suitable, and include Abl1, Abl2, Brk, BMX, Csk, Fes/Fps, Fgr, Fyn, FynT, Hck, Hyl, ITK, Jak3, Lck, LynA, LynB, Src, Src, N1, SYK, Tec, and YES. CLK1 is a dual protein kinase and may also be used in the present invention.

Eukaryotic protein phosphatases are structurally and functionally diverse enzymes that have been classified into three distinct gene families. Two of these families dephosphorylate phosphoserine and phosphothreonine amino acids, whereas the protein tyrosine phosphatase family (PTPs) dephosphorylates phosphotyrosine amino acids. A subfamily of the PTPs, the dual specificity phosphatases, dephosphorylates all three phosphoamino acids. Within each family, catalytic domains are reported to be highly conserved, with functional diversity endowed by regulatory domains and subunits.

The protein serine or threonine phosphatases type 1 and 2A reportedly account for as much as 95% of the phosphatase activity in cell extracts (Brautigan and Shriner, Methods. Enzymol. 159: 339-346 (1988)). These enzymes have broad substrate specificities and may be regulated in vivo through targeting of the enzymes to discrete sub-cellular localizations. The total number of protein tyrosine phosphatases encoded in the mammalian genome has been estimated at between 500 and approximately 2000.

Phosphatases for use in the present invention include, without limitation, the following: PTEN, PTP-meg 1, T-cell-PTP N2, PTP1B, LAR, LCA, PP1α, PP2A, PP2B, and PP2C.

Motifs and Peptides for Measuring Protein Phosphorylation and Dephosphorylation

Motifs suitable for detecting or measuring kinase or phosphatase activity generally include an amino acid residue which, when modified, modulates the rate of cleavage of a composition by a protease as compared to the unmodified composition. Typically, peptides of the invention include a motif having a single protease cleavage site (although more may be useful in some applications) and are soluble (e.g. 0.1 mg/ml or greater) in aqueous solution. As one of skill in the art will recognize, the design and size of peptides for specific compositions and the choice of a particular protease is dependent upon the application for which the composition is to be used. For example, for resonance energy transfer type applications, a peptide will typically be in the range of 5 to 50 amino acids in length, or 8 to 50 amino acids in length, or 8 to 25 amino acids in length, or 8 to 15 amino acids in length. For polarization-based applications, these and larger large peptides (e.g., for example 50 to 100 amino acids in length, and up to and including entire protein domains) may be desirable.

Peptides suitable for the invention may include basic amino acids, particularly at the termini, to enhance solubility. In addition, in some embodiments, a peptide can include a C-terminal lysine (K) in order to provide a locus for conjugation to a detectable moiety or binding member (e.g., a fluorescein derivative, biotin, or biotin derivative). In other cases, a peptide can include a terminal cysteine (C) for similar conjugation purposes. A protease cleavage site can be located at any position in a peptide, including within a motif or recognition motif. A motif, recognition motif, or protease cleavage site may be located at any position within a peptide with respect to a first or second detectable moiety. In some embodiments, a protease cleavage site is located in a position relative to a motif/recognition motif such that enzymatic modification of the motif/recognition motif alters the proteolytic cleavage of the peptide (e.g., proteolytic rate or efficiency).

Tyrosine Phosphorylation or Dephosphorylation

Compositions for detecting and monitoring tyrosine kinase activity incorporate a motif (e.g., a recognition motif for a tyrosine kinase) into a peptide, and typically have a single Tyr (Y) as the only aromatic amino acid in the composition. It may also be preferable in certain cases to eliminate or reduce the number of negatively charged amino acids in the P'$_1$, P'$_2$ or P'$_3$ positions. Phosphorylation of a tyrosine amino acid by a tyrosine-directed protein kinase activity modulates the rate of hydrolysis of the composition by a protease (e.g., chymotrypsin) as compared to the non-phosphorylated composition. Illustrative examples of recognition motifs and peptide substrates for tyrosine kinases are shown in Table 2 of U.S. Pat. No. 6,410,255 for use with the protease chymotrypsin. Other illustrative motifs, recognition motifs, and peptides for tyrosine kinases are shown in Table 1, below.

TABLE 1

| Motif | Illustrative Recognition Motif | Illustrative Peptide Sequence |
|---|---|---|
| AIYAA (SEQ ID NO: 1) | EAIYAAP (SEQ ID NO: 2) | EAEAIYAAPGDK (SEQ ID NO: 3) |
| QDYLS (SEQ ID NO: 4) | DQDYLSL (SEQ ID NO: 5) | GDQDYLSLDK (SEQ ID NO: 6) |
| EIYGV (SEQ ID NO: 7) | EEIYGVI (SEQ ID NO: 8) | EEEIYGVIEK (SEQ ID NO: 9) |
| TX$_1$YVA, where X$_1$ can be G, A, or E (SEQ ID NO: 10) | LTGYVAR (SEQ ID NO: 11); ITAYVAT (SEQ ID NO: 12); ITEYVAT (SEQ ID NO: 13) | GVLTGYVARRK (SEQ ID NO: 14); DDEITAYVATRK (SEQ ID NO: 15); TGIITEYVATRK (SEQ ID NO: 16) |
| EEYIQ (SEQ ID NO: 17) | EEEYIQI (SEQ ID NO: 18) | EEEEYIQIVK (SEQ ID NO: 19) |
| DYSQV (SEQ ID NO: 20) | GDYSQVL (SEQ ID NO: 21) | EGDYSQVLEK (SEQ ID NO: 22) |
| EIYAA (SEQ ID NO: 168) | EEIYAAR (SEQ ID NO: 169) | AAEEIYAARRGK (SEQ ID NO: 170) |

Compositions for detecting protein tyrosine phosphatase activity incorporate a motif (e.g., a recognition motif for a tyrosine kinase) into a peptide, where one or more tyrosine amino acids in the motif are phosphorylated. Dephosphorylation of a tyrosine amino acid in such compositions by a tyrosine-directed protein phosphatase activity modulates the rate of hydrolysis by a protease (e.g., chymotrypsin) as compared to the phosphorylated composition. Illustrative phosphatase motifs, recognition motifs, and peptides are shown in Table 2, below, where Y* indicates a phosphorylated tyrosine.

TABLE 2

| Motif | Illustrative Recognition Motif | Illustrative Peptide Sequence |
|---|---|---|
| AIY*AA (SEQ ID NO: 23) | EAIY*AAP (SEQ ID NO: 24) | EAEAIY*AAPGDK (SEQ ID NO: 25) |
| QDY*LS (SEQ ID NO: 26) | DQDY*LSL (SEQ ID NO: 27) | GDQDY*LSLDK (SEQ ID NO: 28) |
| EIY*GV (SEQ ID NO: 29) | EEIY*GVI (SEQ ID NO: 30) | EEEIY*GVIEK (SEQ ID NO: 31) |
| $TX_1Y$*VA, where $X_1$ can be G, A, or E (SEQ ID NO: 32) | LTGY*VAR (SEQ ID NO: 33); ITAY*VAT (SEQ ID NO: 34); ITEY*VAT (SEQ ID NO: 35) | GVLTGY*VARRK (SEQ ID NO: 36); DDEITAY*VATRK (SEQ ID NO: 37); TGIITEY*VATRK (SEQ ID NO: 38) |
| EEY*IQ (SEQ ID NO: 39) | EEEY*IQI (SEQ ID NO: 40) | EEEEY*IQIVK (SEQ ID NO: 41) |

TABLE 2-continued

| Motif | Illustrative Recognition Motif | Illustrative Peptide Sequence |
|---|---|---|
| DY*SQV (SEQ ID NO: 42) | GDY*SQVL (SEQ ID NO: 43) | EGDY*SQVLEK (SEQ ID NO: 44) |
| EIY*AA (SEQ ID NO: 171) | EEIY*AAR (SEQ ID NO: 172) | AAEEIY*AARRGK (SEQ ID NO: 173) |

Serine/Threonine (S/T) Phosphorylation or Dephosphorylation

Compositions for measuring serine or threonine kinase activities incorporate a motif (e.g., a recognition motif for a S/T kinase) typically containing a single aromatic amino acid (Tyr, Trp or Phe) generally within about three amino acids of a serine or threonine amino acid. A serine or threonine amino acid is phosphorylated by an appropriate serine or threonine specific kinase. It may be preferable in certain cases (depending on the protease selected) to eliminate or reduce the number of negatively charged amino acids (e.g. Asp or Glu amino acids) in the $P_1$, $P'_2$ or $P'_3$ positions to ensure that serine or threonine phosphorylation provides a large modulation in proteolytic sensitivity of the composition upon phosphorylation. Examples of illustrative recognition motifs and peptides are provided in Table 3 of U.S. Pat. No. 6,410,255 for use with chymotrypsin. Illustrative motifs, recognition motifs, and peptides for S/T kinases are also shown in Table 3, below.

TABLE 3

| Motif | Illustrative Recognition Motif | | Illustrative Peptide Sequence | |
|---|---|---|---|---|
| $RRX_1(S/T)L$, where $X_1$ can be F, W, or Y (SEQ ID NO: 45) | LRRFSLG | (SEQ ID NO: 46) | ALRRFSLGEK | (SEQ ID NO: 47) |
| $LX_1(S/T)TT$, where $X_1$ can be F, W, or Y (SEQ ID NO: 48) | GLFSTTP | (SEQ ID NO: 49) | RGGLFSTTPGGTK, | (SEQ ID NO: 50) |
| $X_1L(S/T)LD$, where $X_1$ can be F, W, or Y (SEQ ID NO: 51) | DYLSLDK | (SEQ ID NO: 52) | GDQDYLSLDK, | (SEQ ID NO: 53) |
| $RX_1X_2(S/T)X_3$, where $X_1$ can be V, A, or Q, $X_2$ can be F, W, or Y, and $X_3$ can be V or L (SEQ ID NO: 54) | NRVFSVA, PRAFSVG, RRQFSLR | (SEQ ID NO: 55) (SEQ ID NO: 56) (SEQ ID NO: 57) | KLNRVFSVAC, ARPRAFSVGK, RRRQFSLRRKAK | (SEQ ID NO: 58) (SEQ ID NO: 59) (SEQ ID NO: 60) |
| $TX_1S(S/T)L$, where $X_1$ can be F, W, or Y (SEQ ID NO: 61) | RTFSSLA | (SEQ ID NO: 62) | RPRTFSSLAEGK | (SEQ ID NO: 63) |
| $X_1X_2(S/T)PX_3$ where $X_1$ can be P or I, $X_3$ can be F, W, or Y, and $X_2$ can be G, K, or D (SEQ ID NO: 64) | APFSPGG, HPFSPKK, KIFSPDV | (SEQ ID NO: 65) (SEQ ID NO: 66) (SEQ ID NO: 67) | VAPFSPGGRAK, AKHPFSPKKAK, IIKIFSPDVEK, | (SEQ ID NO: 68) (SEQ ID NO: 69) (SEQ ID NO: 70) |
| $X_1(S/T)X_2X_3VA$, where $X_1$ can be F, W, or Y, $X_2$ can be A, E, or Q, and $X_3$ can be Y or H (SEQ ID NO: 71) | EFTAYVA, IFTEYVA, VFTQHVA | (SEQ ID NO: 72) (SEQ ID NO: 73) (SEQ ID NO: 74) | DDEFTAYVATRK, TGIFTEYVATRK, TGVFTQHVATRK | (SEQ ID NO: 75) (SEQ ID NO: 76) (SEQ ID NO: 77) |
| $IX_1(S/T)IAN$, where $X_1$ can be F, W, or Y (SEQ ID NO: 78) | RIFSIANS | (SEQ ID NO: 79) | QRIFSIANSIVK | (SEQ ID NO: 80) |
| $SIAX_1(S/T)I$, where $X_1$ can be F, W, or Y (SEQ ID NO: 81) | DSIAFSIV | (SEQ ID NO: 82) | RIDSIAFSIVGK | (SEQ ID NO: 83) |
| (S/T)VPPS*P, where S* is a phosphorylated serine (SEQ ID NO: 84) | FSVPPS*PD, where S* is a phosphorylated serine, (SEQ ID NO: 85) | | PRPFSVPPS*PDK, where S* is a phosphorylated Serine (SEQ ID NO: 86) | |
| $DX_1X_2(S/T)X_3$, where $X_1$ can be A or E, $X_2$ can be F, W, or Y, and $X_3$ can be I or Q (SEQ ID NO: 87) | EDAFSII, EDEFSQN | (SEQ ID NO: 88), (SEQ ID NO: 89) | EEDAFSIIGK, REDEFSQNEEK | (SEQ ID NO: 90), (SEQ ID NO: 91) |

TABLE 3-continued

| Motif | Illustrative Recognition Motif | Illustrative Peptide Sequence |
|---|---|---|
| DX$_1$(S/T)QV, where X$_1$ can be F, W, or Y (SEQ ID NO: 92) | EGDYSQV (SEQ ID NO: 93) | EGDYSQVLEK (SEQ ID NO: 22) |
| RQF(S/T)V (SEQ ID NO: 174) | SRQFSVA (SEQ ID NO: 175) | KKKALSRQFSVAAK (SEQ ID NO: 176) |
| SF(S/T)SS (SEQ ID NO: 177) | ESFSSSE (SEQ ID NO: 178) | ESFSSSEEK (SEQ ID NO: 179) |
| FG(S/T)PN (SEQ ID NO: 180) | SFGSPNR (SEQ ID NO: 181) | VLAKSFGSPNRARKKK (SEQ ID NO: 182) |
| RRY(S/T)N (SEQ ID NO: 183) | QRRYSNV (SEQ ID NO: 184) | KKRPQRRYSNVLK (SEQ ID NO: 185) |
| RL(S/T)FA (SEQ ID NO: 186) | RRLSFAE (SEQ ID NO: 187) | RRRLSFAEPGK (SEQ ID NO: 188) |
| PF(S/T)PS (SEQ ID NO: 189) | EPFTPSG (SEQ ID NO: 190) | LVEPFTPSGEAPNQKK (SEQ ID NO: 191) |
| EA(S/T)FA (SEQ ID NO: 192) | IEASFAE (SEQ ID NO: 193) | EVIEASFAEQEAK (SEQ ID NO: 194) |

Compositions for detecting protein serine or threonine phosphatase activity incorporate a motif (e.g., a recognition motif for a S/T kinase) into a peptide, where one or more serine or threonine amino acids in the motif are phosphorylated. Dephosphorylation of a serine or threonine amino acid in the composition by a serine- or threonine-directed protein phosphatase activity modulates the rate of hydrolysis by a protease (e.g., chymotrypsin) as compared to the phosphorylated composition. Illustrative phosphatase motifs, recognition motifs, and peptides are set forth in Table 4, below, where (S/T)* indicates a phosphorylated serine or threonine, S* indicates a phosphorylated serine, and T* indicates a phosphorylated threonine.

TABLE 4

| Motif | Illustrative Recognition Motif | Illustrative Peptide Sequence |
|---|---|---|
| RRX$_1$(S/T)*L, where X$_1$ can be F, W, or Y (SEQ ID NO: 95) | LRRFS*LG (SEQ ID NO: 96) | ALRRFS*LGEK (SEQ ID NO: 97) |
| LX$_1$(S/T)*TT, where X$_1$ can be F, W, or Y (SEQ ID NO: 98) | GLFS*TTP (SEQ ID NO: 99) | RGGLFS*TTPGGTK (SEQ ID NO: 100) |
| X$_1$L(S/T)*LD, where X$_1$ can be F, W, or Y (SEQ ID NO: 101) | DYLS*LDK (SEQ ID NO: 102) | GDQDYLS*LDK (SEQ ID NO: 103) |
| RX$_1$X$_2$(S/T)*X$_3$, where X$_1$ can be V, A, or Q, X$_2$ can be F, W, or Y, and X$_3$ can be V or L (SEQ ID NO: 104) | NRVFS*VA, (SEQ ID NO: 105) PRAFS*VG, (SEQ ID NO: 106) RRQFS*LR (SEQ ID NO: 107) | KLNRVFS*VAC, (SEQ ID NO: 108) ARPRAFS*VGK, (SEQ ID NO: 109) RRRQFS*LRRKAK, (SEQ ID NO: 110) |
| TX$_1$S(S/T)*L, where X$_1$ can be F, W, or Y (SEQ ID NO: 111) | RTFSS*LA (SEQ ID NO: 112) | RPRTFSS*LAEGK (SEQ ID NO: 113) |
| X$_1$X$_2$(S/T)*PX$_3$ where X$_1$ can be P or I, X$_3$ can be F, W, or Y, and X$_2$ can be G, K, or D (SEQ ID NO: 114) | APFS*PGG, (SEQ ID NO: 115) HPFS*PKK, (SEQ ID NO: 116) KIFS*PDV (SEQ ID NO: 117) | VAPFS*PGGRAK, (SEQ ID NO:118) AKHPFS*PKKAK, (SEQ ID NO: 119) IIKIFS*PDVEK, (SEQ ID NO: 120) |
| X$_1$(S/T)*X$_2$X$_3$VA, where X$_1$ can be F, W, or Y, X$_2$ can be A, E, or Q, and X$_3$ can be Y or H (SEQ ID NO: 121) | EFT*AYVA, (SEQ ID NO: 122) IFT*EYVA, (SEQ ID NO: 123) VFT*QHVA (SEQ ID NO: 124) | DDEFT*AYVATRK, (SEQ ID NO: 125) TGIFT*EYVATRK, (SEQ ID NO: 126) TGVFT*QHVATRK (SEQ ID NO: 127) |
| IX$_1$(S/T)*IAN, where X$_1$ can be F, W, or Y (SEQ ID NO: 128) | RIFS*IANS (SEQ ID NO: 129) | QRIFS*IANSIVK (SEQ ID NO: 130) |
| SIAX$_1$(S/T)*I, where X$_1$ can be F, W, or Y (SEQ ID NO: 131) | DSIAFS*IV (SEQ ID NO: 132) | RIDSIAFS*IVGK (SEQ ID NO: 133) |
| (S/T)*VPPS*P (SEQ ID NO: 134) | FS*VPPS*PD (SEQ ID NO: 135) | PRPFS*VPPS*PDK (SEQ ID NO: 136) |
| DX$_1$X$_2$(S/T)*X$_3$, where X$_1$ can be A or E, X$_2$ can be F, W, or Y, and X$_3$ can be I or Q (SEQ ID NO: 137) | EDAFS*II, (SEQ ID NO: 138) EDEFS*QN (SEQ ID NO: 139) | EEDAFS*IIGK, (SEQ ID NO: 140) REDEFS*QNEEK (SEQ ID NO: 141) |
| DX$_1$(S/T)*QV, where X$_1$ can be F, W, or Y (SEQ ID NO: 142) | EGDYS*QV (SEQ ID NO: 143) | EGDYS*QVLEK (SEQ ID NO: 144) |
| RQF(S/T)*V (SEQ ID NO: 195) | SRQFS*VA (SEQ ID NO: 196) | KKKALSRQFS*VAAK (SEQ ID NO: 197) |

TABLE 4-continued

| Motif | Illustrative Recognition Motif | Illustrative Peptide Sequence |
|---|---|---|
| SF(S/T)*SS (SEQ ID NO: 198) | ESFS*SSE (SEQ ID NO: 199) | ESFS*SSEEK (SEQ ID NO: 200) |
| FG(S/T)*PN (SEQ ID NO: 201) | SFGS*PNR (SEQ ID NO: 202) | VLAKSFGS*PNRARKKK (SEQ ID NO: 203) |
| RRY(S/T)*N (SEQ ID NO: 204) | QRRYS*NV (SEQ ID NO: 205) | KKRPQRRYS*NVLK (SEQ ID NO: 206) |
| RL(S/T)*FA (SEQ ID NO: 207) | RRLS*FAE (SEQ ID NO: 208) | RRRLS*FAEPGK (SEQ ID NO: 209) |
| PF(S/T)*PS (SEQ ID NO: 210) | EPFT*PSG (SEQ ID NO: 211) | LVEPFT*PSGEAPNQKK (SEQ ID NO: 212) |
| EA(S/T)*FA (SEQ ID NO: 213) | IEAS*FAE (SEQ ID NO: 214) | EVIEAS*FAEQEAK (SEQ ID NO: 215) |

Protease

Many proteases for use in the present invention are commonly available at high purity. Typically, the proteolytic activity of a protease for a composition is modulated by the presence or absence of a post-translationally modified (e.g., phosphorylated) amino acid in a motif. Preferred compositions exhibit a significant modulation, e.g. at least 1.5, 2, 3, 4, 5, 7, 10, 15, 20, 25, 30, 35, 40, 50 or 100 fold modulation, of proteolytic reactivity when modified as compared to when non-modified. See Table 5 below for illustrative proteases.

Detectable Moieties

The choice of a detectable moiety is governed by a number of factors including the mode of detection, the availability of specific instrumentation, and the ease of coupling of the detectable moiety to a peptide. Other factors that may be relevant to a particular use include the effect of a detectable moiety on the solubility of a composition, the kinetics of the post-translational activity or protease activity with respect to a composition, and the desired detection sensitivity of an assay.

TABLE 5

| Name | EC number | Type | Peptide bond cleaved | Primary Specificity |
|---|---|---|---|---|
| Caspase 3 | | Cysteine | DXXD-P'$_1$ | P$_1$ = Asp, P'$_1$ = neutral preferred |
| Cathepsin G | EC 3.4.21.20 | Serine | P$_1$-P'$_1$ | P$_1$ = aromatic preferred, W, Y, F |
| Chymotrypsin | EC 3.4.21.1 | Serine | P$_1$-P'$_1$ | P$_1$ = aromatic preferred, W, Y, F |
| Elastase | EC 3.4.21.36 | Serine | P$_1$-P'$_1$ | P$_1$ = uncharged, non aromatic, e.g. A, V, L, 1, G, S, T |
| Endoproteinase Asp-N | | Unknown | P$_1$-Asp | P'$_1$ = Asp or P'$_1$ = Cysteic acid P$_1$ = non-specific |
| Endoproteinase Glu-N | EC 3.4.21.9 | Serine | Glu-P'$_1$ | P$_1$ = Glu or Asp P'$_1$ = non-specific |
| *Streptomyces griseus* GluSGP | EC 3.4.21.82 | Serine | Glu-P'$_1$ | P$_1$ = Glu or Asp P'$_1$ = non-specific |
| *Staphylococcus aureus* V8 | EC 3.4.21.19 | Serine | Glu-P'$_1$ | P$_1$ = Glu or Asp P'$_1$ = non-specific |

Proteases that may be used to measure peptide phosphorylation or dephosphorylation include those that recognize a composition that includes at least one motif position in which the presence or absence of a phosphorylated amino acid modulates the activity of the protease towards that composition. The flexibility in choice of motifs containing or lacking phosphorylated amino acids (e.g., tyrosine, serine or threonine) combined with the flexibility in choice of the protease enables many protein kinase or phosphatase activities to be measured using the present invention.

In a cell-based application of the present method, the expression of a protease within a cell is regulated (e.g., using inducible nucleic acid constructs that encode the protease). Suitable nucleic acid constructs can be designed and used as a matter of routine by those skilled in the art. In such cell-based assays, an appropriate measurable (e.g., optical) property of a composition that includes at least one motif position in which the presence or absence of a phosphorylated residue modulates the activity of the protease towards that composition can be monitored at one or more time intervals after the onset of increased expression of the protease.

Numerous detectable moieties are commercially available or can be readily made. In general, a detectable moiety can exhibit an optical property, a magnetic property, or a radioactive property. Thus, once associated with a peptide, a detectable moiety allows a resulting composition to exhibit an optical property, a magnetic property, or a radioactive property that is similar to or the same as that of the detectable moiety alone. In some embodiments, the association of a detectable moiety with a peptide may alter a detectable property of the detectable moiety to a greater or lesser extent. For example, conjugation of a fluorophore to a peptide may result in a composition having an emission maximum that is different from that of the fluorophore alone in solution. In other embodiments, a detectable moiety can be a member of a specific binding pair. For example, a detectable moiety can be the ligand member of a ligand-protein binding pair, e.g., the biotin member of the biotin-streptavidin binding pair.

For fluorescent detectable moieties, preferred fluorophores typically exhibit good quantum yields, long excited state lifetimes, and large extinction coefficients; are resistant to collisional quenching and bleaching; and should be easily conjugated to a peptide. Fluorophores that show absorbance and emission in the red and near-infrared range are useful in whole animal studies because of reduced scattering background fluorescence and greater transmission through tissues. Examples of illustrative fluorophores include cyanines, oxazines, thiazines, porphyrins, phthalocyanines, fluorescent infrared-emitting polynuclear aromatic hydrocarbons such as violanthrones, fluorescent proteins, near IR squaraine dyes. (for example, as shown in Dyes and Pigments 17:19-27 (1991), U.S. Pat. No. 5,631,169 to Lakowicz et al., issued May 20, 1997, and organo-metallic complexes such as ruthenium and lanthanide complexes of U.S. Pat. Nos. 4,745,076 and 4,670,572, the disclosures of which are incorporated herein by reference).

Suitable fluorophores and dark quenchers for use in the present invention are commercially available, e.g., from Molecular Probes (Eugene, Oreg.), Attotec (Germany), Amersham, and Biosearch Technologies (Novato, Calif.). Specific fluorophores include, without limitation, fluorescein isothiocyanate (especially fluorescein-5-isothiocyanate), 5-FAM (5-carboxyfluorescein), 6-FAM (6-carboxyfluorescein), 5,6-FAM, 7-hydroxycoumarin-3-carboxamide, 6-chloro-7-hydroxycoumarin-3-carboxamide, dichlorotriazinylaminofluorescein, tetramethylrhodamine-5 (and -6)-isothiocyanate, 1,3-bis-(2-dialkylamino-5-thienyl)-substituted squarines, the succinimidyl esters of 5 (and 6) carboxyfluoroscein, 5 (and 6)-carboxytetramethylrhodamine, fluorescein maleimide and 7-amino-4-methylcoumarin-3-acetic acid. Semiconductor fluorescent nanocrystals are available with a range of emission spectra, are highly fluorescent and are also useful (see Bruchez et al., Science 281: 2013-2016).

Lanthanide complexes (e.g., metal chelates of Eu or Tb) are also useful and have the advantage of not being quenched by oxygen. Their long lifetimes (on the order of ms as compared to ns for other fluorophores) may allow easy suppression of the auto-fluorescence of biological samples, as fluorescent signals may be measured after background signals have decayed. Accordingly, lanthanide complexes, such as Eu or Tb metal chelates, may be particularly useful, e.g., in time-resolved FRET (TR-FRET) applications. See, for example, U.S. Pat. Nos. 5,639,615, 5,622,821, and 5,656,433.

Some embodiments involve FRET and/or TR-RET applications. In some of these cases, a donor fluorescent moiety and an acceptor fluorescent moiety are employed as first and second detectable moieties. In some TR-RET applications, a luminescent metal complex is used as the donor detectable moiety.

Illustrative luminescent moieties include chemiluminescent, electroluminescent, and bioluminescent compounds. Preferred bioluminescent compounds include bioluminescent proteins such as firefly, bacterial, or click beetle luciferases, aequorins, and other photoproteins (for example as described in U.S. Pat. No. 5,221,623, issued Jun. 22, 1989 to Thompson et al., U.S. Pat. No. 5,683,888 issued Nov. 4, 1997 to Campbell; U.S. Pat. No. 5,674,713 issued Sep. 7, 1997 to DeLuca et al.; U.S. Pat. No. 5,650,289 issued Jul. 22, 1997 to Wood; and U.S. Pat. No. 5,843,746 issued Dec. 1, 1998 to Tatsumi et al.). Preferred electroluminescent moieties include ruthenium complexes, as for example described in U.S. Pat. No. 5,597,910 issued to Jan. 28, 1997 to Gudibande. Preferred chemiluminescent moieties include those based on 1,2-dioxetanes, as for example described in U.S. Pat. No. 4,372,745 issued Feb. 8, 1983 to Mandle et al., U.S. Pat. No. 5,656,207 issued Aug. 12, 1997 to Woodhead et al., and U.S. Pat. No. 5,800,999 issued Sep. 1, 1998 issued to Bronstein et al.

Magnetic detectable moieties include MR contrast agents, e.g., chelates of paramagnetic, ferromagnetic, or diamagnetic metal ions, or magnetic particles (e.g., USPIOs, MIONs; see U.S. Pat. No. 5,262,176). In some embodiments, a chelate may comprise a lipophilic group as described in U.S. Pat. No. 5,628,982, issued May 13, 1997 to Lauffer et al., and U.S. Pat. No. 5,242,681, issued Sep. 7, 1993 to Elgavish et al. For reviews of metal chelates useful in MR imaging, see Lauffer, "Paramagnetic Metal Complexes as Water Proton Relaxation Agents for NMR Imaging: Theory and Design," Chem. Rev. 87(5):901-927 (1987); and Caravan et al., "Gadolinium (III) Chelates as MRI Contrast Agents: Structure, Dynamics, and Applications," Chem. Rev. 99(9):2293-2352 (1999).

In some applications it may be desirable to derivatize a detectable moiety to render it more hydrophobic and permeable to cell membranes. The derivatizing groups may undergo hydrolysis inside cells to regenerate the compositions, thus trapping them within cells. For this purpose, it is preferred that phenolic hydroxyls or free amines in the structures are acylated with $C_1$-$C_4$ acyl groups (e.g. formyl, acetyl, n-butyl) or converted to, e.g., esters and carbonates, as described in Bundgaard, H., Design of Prodrugs, Elsevier Science Publishers (1985), Chapter 1, page 3 et seq. Further modification of fluorescent moieties may also be accomplished e.g., as described in U.S. Pat. No. 5,741,657 issued Apr. 21, 1998 to Tsien et al.

A detectable moiety may be attached to a peptide by a linker (L) that provides a spacer between the detectable moiety and the peptide, thereby preventing steric or charge interference of the detectable moiety on the interaction between, e.g., the recognition motif of the peptide and a kinase or phosphatase. Preferred linkers are substantially stable under cellular conditions and easily coupled to a peptide and detectable moiety. Examples include flexible aliphatic linkers such as γ-amino-n-butyric acid (GABA), diaminopentane, and aminohexanoyl, as well as rigid aromatic linkers. Such linkers are known in the art and described for example in the Handbook of Fluorescent Probes and Research Chemicals, by Richard Haugland, published by Molecular Probes. Other linkers include amino acid moieties or small dipeptides (e.g., gly-gly linkers) and linkers described herein.

Non-covalent methods of attachment may also be used to associate a peptide with a detectable moiety. For example, a peptide may be designed to encompass a specific binding site for a fluorescent moiety, as described in pending U.S. Pat. Nos. 6,054,271; 6,008,378, and 5,932,474. Labeling may then be achieved by incubation of a peptide with a membrane-permeable fluorescent binding partner, which has the advantages of enabling the expression of peptides within intact living cells, and the subsequent labeling of these peptides in situ to create compositions of the present invention within intact living cells.

Luminescent Metal Complex

A luminescent metal complex can act as a donor fluorophore in a RET or TR-RET assay. A luminescent metal complex is useful because its excited state lifetime is typically on the order of milliseconds or hundreds of microseconds rather than nanoseconds; a long excited state lifetime allows detection of a molecular interaction between binding members to be monitored after the decay of background fluorescence and/or interference from light-scattering.

Methods for covalently linking a luminescent metal complex to a variety of compounds, including binding members, are known to those of skill in the art, see, e.g., WO 96/23526, WO 01/09188, WO 01/08712, and WO 03/011115; and U.S. Pat. Nos. 5,639,615; 5,656,433; 5,622,821; 5,571,897; 5,534,622; 5,220,012; 5,162,508; and 4,927,923.

A luminescent metal complex can include a metal liganding moiety, one or more lanthanide metal ions, and optionally linkers, spacers, and organic antenna moieties.

Metal Liganding Moiety

A metal liganding moiety coordinates one or more lanthanide metal ions to form a metal complex. Typically, a metal liganding moiety includes one or more metal coordinating moieties X, where X is a heteroatom electron-donating group capable of coordinating a metal cation, such as $O^-$, OH, $NH_2$, $OPO_3^{2-}$, NHR, or OR where R is an aliphatic group.

A metal liganding moiety can be a chelating moiety or a cryptand moiety. If a lanthanide metal ion is coordinated to a chelating moiety, the complex is referred to as a "metal chelate." If a lanthanide metal ion is coordinated to a cryptand moiety, the complex is referred to as a "metal cryptand."

A metal chelate should be stable to exchange of the lanthanide ion. Metal chelates preferably have a formation constant ($K_f$) of greater than $10^{10}$ $M^{-1}$. A variety of useful chelating moieties are known to those of skill in the art. Typical examples of chelating moieties include: EDTA, DTPA, TTHA, DOTA, NTA, HDTA, DTPP, EDTP, HDTP, NTP, DOTP, DO3A, DOTAGA, and NOTA.

In some embodiments, a luminescent metal chelate can have the following structures:

-$L_n$-A-$S_n$-$C_M$, or

-$L_n$-$C_M$-$S_n$-A, wherein A represents an organic antenna moiety;

L represents a linker (e.g., for conjugation to a probe or peptide composition);

S represents a spacer;

n can be 0 or 1;

C represents a metal chelating moiety; and

M represents a lanthanide metal ion coordinated to C.

Figure 3:
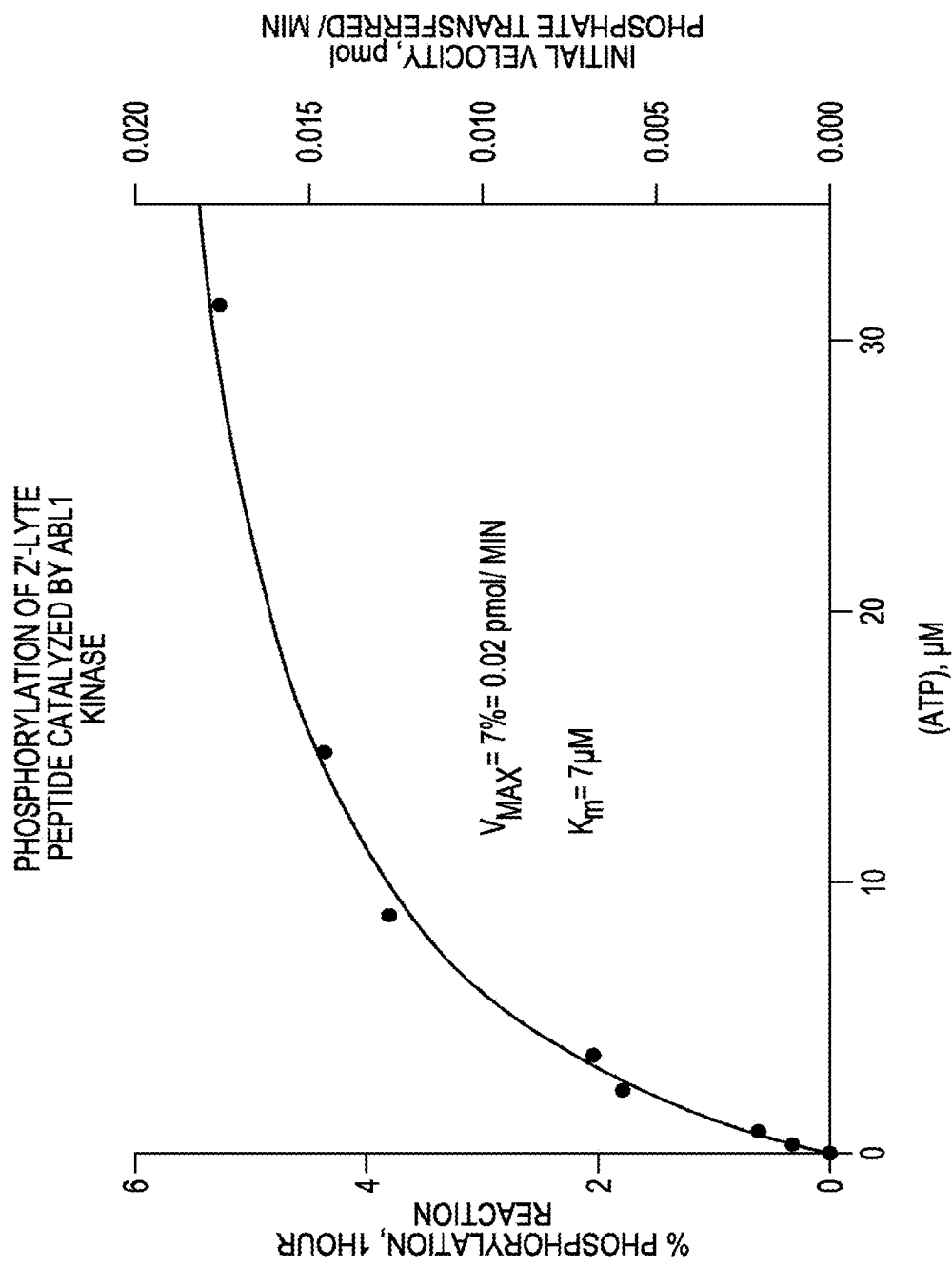
FIG. 3 illustrates the derivation of kinetic parameters for Abl 1 kinase.

For illustrative examples of luminescent metal chelates, see FIGS. 2 and 3 of U.S. Patent Publication no. 2005/0170442. FIG. 3 of U.S. Patent Publication no. 2005/0170442 also shows luminescent metal chelates useful for conjugating to amine moieties (FIG. 3A) or thiol moieties (FIG. 3B).

Cryptates are formed by the inclusion of a lanthanide cation into a tridimensional organic cavity, leading to highly stable complexes. A variety of useful cryptand moieties are known to those of skill in the art. Examples of cryptand moieties useful in the present methods include: trisbypyridine (TBP, e.g, TBP pentacarboxylate), and pyridine bipyridine (e.g., pyridine bipyridine tetracarboxylate).

Chelating and cryptand moieties can be synthesized by a variety of methods known to those of skill in the art or may be purchased commercially. See U.S. Pat. Nos. 5,639,615; 5,656,433; 5,622,821; 5,571,897; 5,534,622; 5,220,012; 5,162,508; and 4,927,923; and WO 96/23526 and WO 03/011115.

Lanthanide Metal Ions

Metal liganding moieties coordinate one or more lanthanide metal ions to form a metal complex. Lanthanide metal ions are useful because their special electronic configuration shields the optically active electrons, resulting in characteristic line type emissions. As the electronic transitions of the metal ions are forbidden by quantum mechanics rules, the emission lifetimes of these ions are typically long (from μs to msec).

Useful lanthanide metal ions include Sm(III), Ru(III), Eu(III), Gd(III), Tb(III), and Dy(III). Methods for complexing a metal ion to a' chelating or cryptand moiety are known to those of skill in the art, see, e.g., WO 96/23526 and WO 03/011115.

Organic Antenna Moiety

A luminescent metal complex can optionally include an organic antenna moiety. An organic antenna moiety typically has a conjugated electronic structure so that it can absorb light. The absorbed light is transferred by intramolecular non-radiative processes from the singlet to the triplet excited state of the antenna moiety, then from the triplet state to the emissive level of the lanthanide ion, which then emits characteristically long-lived luminescence. For example, see FIG. 2 of U.S. Patent Publication no. 2005/0170442. It should be noted that some metal liganding moieties can absorb light without the inclusion of an organic antenna moiety. For example, certain cryptand moieties that contain conjugated organic moieties, such as tribipyridine pentacarboxylate, do not require the inclusion of a discrete organic antenna moiety.

In some embodiments, an organic antenna moiety can be a polynuclear heterocyclic aromatic compound. The polynuclear heterocylic aromatic compound can have two or more fused ring structures. Examples of useful organic antenna moieties include rhodamine 560, fluorescein 575, fluorescein 590, 2-quinolone, 4-quinolone, 4-trifluoromethylcoumarin (TFC), 7-diethyl-amino-coumarin-3-carbohydrazide, 7-amino-4-methyl-2-coum-arin (carbostyril 124, CS124), 7-amino-4-methyl-2-coumarin (coumarin 120), 7-amino-4-trifluoromethyl-2-coumarin (coumarin 124), and aminomethyltrimethylpsoralen.

Compounds useful as organic antenna moieties can be synthesized by methods known to those of skill in the art or purchased commercially. See, e.g., U.S. Pat. Nos. 5,639,615; 5,656,433; 5,622,821; 5,571,897; 5,534,622; 5,220,012; 5,162,508; and 4,927,923.

Linkers, Spacers

Linkers and Spacers can optionally be included in a luminescent metal complex. A Linker (L) functions to link a luminescent metal complex to a composition or probe composition. In some embodiments, a L can link an acetate, amine, amide, carboxylate, or methylene functionality on a metal liganding moiety to a composition or probe composition.

One of skill in the art can design Ls to react with a number of functionalities, including, without limitation, amines, acetates, thiols, alcohols, ethers, esters, ketones, and carboxylates. In embodiments where the composition is a polypeptide, a L can cap the N-terminus, the C-terminus, or both N- and C-termini, as an amide moiety. Other exemplary L capping moieties include sulfonamides, ureas, thioureas and carbamates. Ls can also include linear, branched, or cyclic alkanes, alkenes, or alkynes, and phosphodiester moieties. The L may be substituted with one or more functional groups, including ketone, ester, amide, ether, carbonate, sulfonamide, or carbamate functionalities. Specific Ls contemplated also include NH—CO—NH—; —CO—$(CH_2)_n$-NH—, where n=1 to 10; —NH-Ph-; —NH—$(CH_2)_n$-, where n=1 to 10; —CO—NH—; —$(CH_2)_n$-NH—, where n=1 to 10; —CO—$(CH_2)_n$-NH—, where n=1 to 10; and —CS—NH—. Additional examples of Ls and synthetic methodologies for incorporating them into metal complexes, particularly metal complexes linked to polypeptides, are set forth in WO 01/09188, WO 01/08712, and WO 03/011115.

A Spacer (S) can connect an organic antenna moiety to a metal liganding moiety. In some embodiments, a S can link an acetate, amine, or methylene functionality on a metal liganding moiety to an organic antenna moiety. One of skill in the art can design Ss to react with a number of functionalities on organic antenna moieties and on metal liganding moieties, including, without limitation, amines, acetates, thiols, alcohols, ethers, esters, ketones, and carboxylates. Ss can include linear, branched, or cyclic alkanes, alkenes, or alkynes, and phosphodiester moieties. The S may be substituted with one or more functional groups, including ketone, ester, amide, ether, carbonate, sulfonamide, or carbamate functionalities. Specific Ss contemplated also include NH—CO—NH—; —CO—(CH$_2$)$_n$-NH—, where n=1 to 10; —NH-Ph-; —NH—(CH$_2$)$_n$-, where n=1 to 10; —CO—NH—; —(CH$_2$)$_n$-NH—, where n=1 to 10; —CO—(CH$_2$)$_n$-NH—, where n=1 to 10; and —CS—NH—.

Fluorescent Acceptor Moiety

A fluorescent acceptor moiety can act as an acceptor in RET or TR-RET-based assays and/or can be a fluorophore for which the polarization of fluorescence emission is measured in an FP-based assay. Thus, the inclusion of a fluorescent acceptor moiety can allow multiplex assays to be performed, e.g., where FRET and/or FP are measured.

In general, a fluorescent acceptor moiety should exhibit a good quantum yield and a large extinction coefficient; should be resistant to collisional quenching and bleaching; and should be easily conjugated to a variety of compositions and probe compositions by methods known to those having ordinary skill in the art. Suitable fluorophores include, without limitation, fluorescein, rhodamine, FITCs (e.g., fluorescein-5-isothiocyanate), 5-FAM, 6-FAM, 5,6-FAM, 7-hydroxycoumarin-3-carboxamide, 6-chloro-7-hydroxycoumarin-3-carboxamide, dichlorotriazinylaminofluorescein, tetramethylrhodamine-5-isothiocyanate, tetramethylrhodamine-6-isothiocyanate, succinimidyl ester of 5-carboxyfluorescein, succinimidyl ester of 6-carboxyfluorescein, 5-carboxytetramethylrhodamine, 6-carboxymethylrhodamine, and 7-amino-4-methylcoumarin-3-acetic acid. Other suitable fluorophores include the Cy family of fluorophores (Cy 3, Cy3B, Cy3.5, Cy5; available from Amersham Biosciences, Piscataway, N.J.); the Alexa Fluor family (available from Molecular Probes, Eugene, Oreg.); the BODIPY family (available from Molecular Probes, Eugene, Oreg.); carbopyronins; squarines; cyanine/indocyanines; benzopyrylium heterocycles; and amide-bridged benzopyryliums.

Fluorescent proteins and mutants can also be used as fluorescent acceptor moieties. Examples include firefly, bacterial, or click beetle luciferases, aequorins, and other photoproteins (for example as described in U.S. Pat. No. 5,221,623, issued Jun. 22, 1989 to Thompson et al., U.S. Pat. No. 5,683,888 issued Nov. 4, 1997 to Campbell; U.S. Pat. No. 5,674,713 issued Sep. 7, 1997 to DeLuca et al.; U.S. Pat. No. 5,650,289 issued Jul. 22, 1997 to Wood; and U.S. Pat. No. 5,843,746 issued Dec. 1, 1998 to Tatsumi et al.). GFP and GFP mutants are particularly useful in applications using Tb(III)-containing metal complexes. A variety of mutants of GFP from *Aequorea victoria* have been created that have distinct spectral properties, improved brightness, and enhanced expression and folding in mammalian cells compared to the native GFP (e.g., see Table 7 of U.S. Pat. No. 6,410,255 and also Green Fluorescent Proteins, Chapter 2, pages 19 to 47, edited by Sullivan and Kay, Academic Press; U.S. Pat. No. 5,625,048 to Tsien et al., issued Apr. 29, 1997; U.S. Pat. No. 5,777,079 to Tsien et al., issued Jul. 7, 1998; and U.S. Pat. No. 5,804,387 to Cormack et al., issued Sep. 8, 1998).

A fluorescent acceptor moiety for use in multiplex assays should exhibit characteristics useful for RET/TR-RET applications and/or FP applications. For example, for FP assays, a fluorophore preferably exhibits a fluorescent excited state lifetime of at least 1 nanosecond, or at least 2 nanoseconds. For TR-RET applications, a region of the fluorophore's absorbance spectra should overlap with a region of a luminescent metal chelate's emission spectra, while a region of the fluorophore's emission spectra should not overlap substantially with a region of the luminescent metal chelate's emission spectra.

Examples of suitable acceptor fluorophores in TR-RET assays wherein a Tb(III)-containing luminescent metal complex is used as one detectable moiety include: fluorescein (and its derivatives); rhodamine (and its derivatives); Alexa Fluors 488, 500, 514, 532, 546, 555, 568 (available from Molecular Probes); BODIPYs FL, R6G, and TMR (available from Molecular Probes); Cy3 and Cy3B (available from Amersham Biosciences), and IC3 (available from Dojindo Molecular Technologies, Gaithersburg, Md.). Examples of suitable acceptor fluorophores in TR-RET assays wherein a Eu(III)-containing luminescent metal complex is used as one detectable moiety include: Alexa Fluors 594, 610, 633, 647, and 660 (available from Molecular Probes); BODIPYs TR, 630/650, and 650/665 (available from Molecular Probes); Cy5 (available from Amersham Biosciences) and IC5 (available from Dojindo Molecular Technologies).

Methods for incorporating fluorophores into a variety of compositions are known to those of skill in the art; see, e.g., U.S. Pat. No. 6,410,255.

Fluorescent Proteins

For some cell-based applications, fluorescent detectable moieties include endogenously fluorescent proteins, functional engineered fluorescent proteins, and variants thereof. Use of such proteins allows the fluorophore and peptide to be expressed within living cells without the addition of other co-factors or fluorophores. Such compositions provide the ability to monitor post-translational activities within defined cell populations, tissues, or a transgenic organism, for example, by the use of inducible controlling nucleotide sequences to produce a sudden increase in the expression of a composition and protease.

Endogenously fluorescent proteins have been isolated and cloned from a number of marine species including the sea pansies *Renilla reniformis, R. kollikeri* and *R. mullerei* and from the sea pens *Ptilosarcus, Stylatula* and *Acanthoptilum*, as well as from the Pacific Northwest jellyfish, *Aequorea victoria* (Szent-Gyorgyi et al. (SPIE conference 1999), D. C. Prasher et al., Gene, 111:229-233 (1992)). These proteins are capable of forming a highly fluorescent, intrinsic chromophore through the cyclization and oxidation of internal amino acids within the protein that can be spectrally resolved from weakly fluorescent amino acids such as tryptophan and tyrosine.

Fluorescent proteins have also been observed in other organisms. For example, the cloning and expression of yellow fluorescent protein from *Vibrio fischeri* strain Y-1 has been described by T. O. Baldwin et al., Biochemistry (1990) 29:5509-15. This protein requires flavins as fluorescent co-factors. The cloning of Peridinin-chlorophyll a binding protein from the dinoflagellate *Symbiodinium* sp. was described by B. J. Moms et al., Plant Molecular Biology, (1994) 24:673: 77. One useful aspect of this protein is that it fluoresces in red. The cloning of phycobiliproteins from marine cyanobacteria such as *Synechococcus*, e.g., phycoerythrin and phycocyanin, is described in S. M. Wilbanks et al., J. Biol. Chem. (1993) 268:1226-35. These proteins require phycobilins as fluorescent co-factors, whose insertion into the proteins involves auxiliary enzymes. The proteins fluoresce at yellow to red wavelengths. See also PCT US01/04625.

A variety of mutants of the GFP from *Aequorea victoria* have been created that have distinct spectral properties, improved brightness, and enhanced expression and folding in mammalian cells compared to the native GFP (e.g., see Table 7 of U.S. Pat. No. 6,410,255 and also Green Fluorescent Proteins, Chapter 2, pages 19 to 47, edited by Sullivan and Kay, Academic Press; U.S. Pat. No. 5,625,048 to Tsien et al., issued Apr. 29, 1997; 5,777,079 to Tsien et al., issued Jul. 7, 1998; and U.S. Pat. No. 5,804,387 to Cormack et al., issued Sep. 8, 1998). In many cases these functional engineered fluorescent proteins have superior spectral properties to wild-type *Aequorea* GFP and are preferred for use in the compositions of the invention.

Cell-Based Assays

The methods of the present invention can also be employed in cell-based assays. Recombinant production of the compositions within living cells involves, in one embodiment, expressing nucleic acids having sequences that encode a fluorescent protein (e.g., as a detectable moiety) and a peptide of interest as a fusion protein. In one embodiment, a composition comprises a first fluorescent protein (e.g., as the first detectable moiety), a peptide containing a motif, such as a recognition motif for a Y or S/T kinase, a protease site, and a second fluorescent protein (as a second detectable moiety) fused together as a single polypeptide chain. Nucleic acids encoding fluorescent proteins can be obtained by methods known in the art. For example, a nucleic acid encoding the protein can be isolated by polymerase chain reaction of cDNA from a suitable organism using primers based on the DNA sequence of the fluorescent protein. PCR methods are described in, for example, U.S. Pat. No. 4,683,195; Mullis et al. (1987); Cold Spring Harbor Symp. Quant. Biol. 51:263; and Erlich, ed., PCR Technology, (Stockton Press, NY, 1989). Suitable clones may then be identified, isolated and characterized by fluorescence activated cell sorting (FACS), typically enabling the analysis of a few thousand cells per second. The construction of expression vectors and the expression of genes in transfected cells involve the use of molecular cloning techniques also well known in the art; see, e.g., Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds. Nucleic acids used to transfect cells with sequences coding for expression of the polypeptide of interest generally will be in the form of an expression vector including expression control sequences operatively linked to a nucleotide sequence coding for expression of the composition comprising the peptide and fluorescent proteins.

In an alternative embodiment, a composition can include a reporter protein (e.g., as a first detectable moiety), a peptide containing a motif described herein, such as a recognition motif for a Y or S/T kinase, a protease site, and a multimerized ubiquitin fusion protein together as a single polypeptide chain. In these embodiments, the motif-containing peptide functions as a linker between the reporter protein and the multimerized ubiquitin fusion protein. Such a polypeptide can be used to carry out an assay for a kinase (or a phosphatase) in a cell. For example, if a suitable kinase is present and active in a cell, the peptide will be phosphorylated and not subject to degradation by a protease, thereby allowing the ubiquitin fusion protein to destabilize (e.g., promote degradation of) the reporter protein. If kinase activity is not present or is inhibited, the motif-containing peptide will be subject to degradation by the protease, thereby preventing the multimerized ubiquitin fusion protein from destabilizing the reporter protein and preserving reporter protein activity. Suitable reporter proteins, multimerized ubiquitin fusion proteins, and constructs for use in such an embodiment are described in WO 01/57242.

Methods of Measurement and Detection

Methods of measurement and detection include, without limitation, fluorescence spectroscopy, luminescence spectroscopy, absorption spectroscopy, and magnetic resonance spectroscopy (e.g., NMR, MRI). Fluorescent methods include continuous or time resolved fluorescence spectroscopy, fluorescence correlation spectroscopy, fluorescence polarization spectroscopy, and resonance energy based fluorescence spectroscopy. Methods of performing such assays on fluorescent materials are well known in the art and are described in, e.g., Lakowicz, J. R., Topics in Fluorescence Spectroscopy, volumes 1 to 3, New York: Plenum Press (1991); Herman, B., Resonance energy transfer microscopy, in Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N. J., Modern Molecular Photochemistry, Menlo Park Benjamin/Cummings Publishing Col, Inc. (1978), pp. 296-361; and Bernard Valeur, "Molecular Fluorescence: Principles and Applications" Wiley V C H, 2002.

The selection and use of specific detectable moieties (e.g., specific fluorophores or quenchers) for particular applications is generally known in the art; for example, see Berlman, I. B., Energy transfer parameters of aromatic compounds, Academic Press, New York and London (1973), which contains tables of spectral overlap integrals for the selection of resonance energy transfer partners. Additional information sources include the Molecular Probes Catalog (2003) and website; and Tsien et al., 1990 Handbook of Biological Confocal Microscopy, pp. 169-178.

Methods and Assays

Compositions of the present invention can be used in a variety of methods. Standard techniques are usually used for chemical synthesis, fluorescence monitoring and detection, optics, molecular biology, and computer software and integration. Chemical reactions, cell assays, and enzymatic reactions are typically performed according to the manufacturer's specifications where appropriate. See, generally, Lakowicz, J. R. Topics in Fluorescence Spectroscopy, (3 volumes) New York: Plenum Press (1991), and Lakowicz, J. R. Emerging applications of florescence spectroscopy to cellular imaging: lifetime imaging, metal-ligand probes, multi photon excitation and light quenching, Scanning Microsc. Suppl. Vol. 10 (1996) pages 213-24, for fluorescence techniques; Sambrook et al., Molecular Cloning: A Laboratory Manual, 2ed. (1989) Cold Spring Harbor Laboratory Press, Cold Spring Harbor, N.Y., for molecular biology methods; Cells: A Laboratory Manual, $1^{st}$ edition (1998) Cold Spring Harbor Laboratory Press, Cold Spring Harbor, N.Y., for cell biology methods; and Optics Guide 5 Melles Griot® Irvine Calif., and Optical Waveguide Theory, Snyder & Love (published by Chapman & Hall) for general optical methods, all of which are incorporated herein by reference.

Compositions of the present invention can be used to prepare phosphorylated compositions. Methods of the present invention can also be used to characterize a kinase or a phosphatase, e.g., to measure kinetic or thermodynamic parameters. In one method, a composition of matter is used in a reaction with a kinase or phosphatase. The composition is contacted with a kinase or phosphatase under conditions effection for the kinase or phosphatase to phosphorylate or dephosphorylate the composition, respectively, and the ability of the kinase to phosphorylate (or the phosphatase to dephosphorylate) the composition is measured. Ability to phosphorylate a composition may be measured in a number of ways, e.g., in terms of % phosphorylation of the composition in a given time period, at a particular concentration of kinase, or at a particular temperature; or in terms of kinetic parameters (e.g., $V_{max}$, $K_m$). See Examples 1 and 2 and FIGS. 3-5 and 8-9. Methods for using a composition are described in, for example, U.S. Pat. Nos. 6,410,255, 5,917,012, and in Rodems et al., "A FRET-based Assay Platform for Ultra-High Density Drug Screening of Protein Kinases and Phosphatases," ASSAY and Drug Development Technologies, Vol. 1 (1-1), November 2002.

Methods of the present invention can be used to determine whether or not a composition of matter is a substrate for a kinase or phosphatase. In one method, a composition of matter is contacted with an enzyme, e.g., a protein kinase or protein phosphatase; the composition and enzyme are then contacted with a protease; and a measurable property in the protease mixture is monitored. A measurable property can be a detectable property of a composition, a detectable property of a cleavage product of a composition (e.g., a detectable property of a donor fluorescent moiety or a detectable property of an acceptor fluorescent moiety), a detectable property of an enzyme, buffer, or reagent, or any combination thereof. For example, a measurable property may be the net fluorescence emission at a wavelength (or a ratio of the net fluorescence emission at two wavelengths) after a composition has been partially cleaved (e.g., 70% cleavage). In this situation, the measurable property reflects the contribution of the intact composition and the mixture of cleavage products to the fluorescence emission of the mixture at the particular wavelength under consideration.

For kinase reactions, ATP is generally included when a composition is contacted with kinase (e.g., during an incubation with the kinase enzyme). As one of skill in the art will recognize, in those methods employing phosphatase enzymes, a phosphorylated composition of matter as described above is contacted with a phosphatase enzyme. Incubation conditions for a contacting step can vary, e.g., in enzyme concentration, substrate concentration, temperature, and length of time. Incubation temperature conditions typically can be from about 15 to about 40° C.; in some embodiments, the temperature may be about room temperature, e.g., about 20-25° C.

A measurable property in a protease mixture may be compared to a measurable property in a control mixture. A control mixture can include the composition of matter and the protease and is typically prepared without the addition of enzyme and/or without the addition of ATP (e.g., for kinase reactions). Other control samples can comprise a phosphorylated version of the composition incubated with the protease in order to correct for any cleavage of the phosphorylated composition by the protease. One of skill in the art can typically design appropriate control mixtures for reference.

A measurable property can be monitored during an incubation with a kinase or phosphatase or when a kinase or phosphatase incubation is complete. Similarly, a measurable property can be monitored during a protease incubation or when a protease incubation is complete. Typically, a measurable property is measured after a predetermined time period of a kinase, phosphatase, or protease incubation. For example, a measurable property may be measured within 12 hours of the initiation of a kinase (phosphatase) or protease incubation. In some embodiments, a measurable property is measured within 30 minutes, 1 hour, 2 hours, or 4 hours of initiation. A protease incubation can be stopped by a number of known methods, including the addition of a reagent to inhibit proteolytic activity (e.g., aprotinin, PMSF, TPCK, AEBSF, chymotrypsin inhibitor 1, chymotrypsin inhibitor 2), by heating and/or denaturing the protease sample, and by altering pH or metal concentration (e.g., by chelating an active site metal).

A composition is identified as a substrate of a kinase (or phosphatase) if a measurable property in the protease mixture is different from the measurable property in the appropriate control mixture. Generally, the measurable property should be statistically significantly different from the measurable property in the control mixture. As one of skill in the art will recognize, whether or not a difference is statistically significant will depend on the type of measurable property, the type of measurement, and the experimental conditions. It is understood that when comparing measurable properties, a statistically significant difference indicates that that substrate may warrant further study. Typically, a difference in measurable properties is considered statistically significant at $p<0.05$ with an appropriate parametric or non-parametric statistic, e.g., Chi-square test, Student's t-test, Mann-Whitney test, or F-test. In some embodiments, a difference is statistically significant at $p<0.01$, $p<0.005$, or $p<0.001$.

Typically, a detectable property will be an optical property, such as a fluorescence property. In one aspect, the method may be based on a difference in a fluorescence anisotropy measurement of a composition before and after cleavage with a protease. In this case, a composition typically comprises a peptide moiety which contains a motif, e.g., a recognition motif for a kinase or phosphatase, a protease site, and a fluorescent detectable moiety. Modification of the peptide by the kinase (or phosphatase) activity results in a modulation of the rate at which a protease cleaves the peptide, which is sensed by a measurable (e.g., statistically different) change in fluorescence polarization of the composition upon cleavage.

Polarization measurements are based on the relative rotational movement of a fluorophore compared to the excited state life-time of that fluorophore. For globular molecules in dilute solution, the relationship between polarization (p) and the degree of rotational movement can be readily derived (see Weber, Polarization of the fluorescence of solutions, in Fluorescence and Phosphorescence Analysis, Don Hercules (ed.), Interscience Publishers, New York, Chapter 8, pages 217-240 (1966)). Rotational movement can be related to the rotational diffusion constant of the molecule, and hence to the molecular volume. In practice there is a close correlation between molecular size and relative polarization of emitted light from a fluorophore. As a consequence, a significant change in fluorescence polarization can occur when compositions of the present invention are acted upon by a protease. Polarization-based assays are relatively easy to set up and can be obtained over a wide concentration, temperature, and ionic strength range.

In another embodiment of the method, fluorescence anisotropy measurements can be enhanced by attaching one end of a peptide of a composition to a solid matrix or a bead. In either case, cleavage of the composition results in a large drop in fluorescence polarization because of the increased rotational flexibility of the cleavage product of the composition once separated from the solid matrix or bead.

In another aspect, the present invention takes advantage of resonance energy transfer either between two fluorescent moieties (FRET), or a bioluminescent moiety and fluorescent moiety (bioluminescent resonance energy transfer, BRET), or a fluorescent moiety and a quencher (e.g., RET dark quenching) to provide a fluorescent readout.

In FRET applications, a composition typically comprises a first fluorescent detectable moiety and a second fluorescent detectable moiety coupled to a peptide such that a motif (e.g., a recognition motif) and a protease cleavage site are located between the two detectable moieties. In this case, cleavage of the peptide by a protease results in an alteration in energy transfer between the first fluorescent moiety and the second fluorescent moiety that may be used to monitor and measure kinase or phosphatase activity.

In FRET cases, fluorescent moieties are typically chosen such that the excitation spectrum of one of the moieties (the acceptor fluorescent moiety) overlaps with the emission spectrum of the donor fluorescent moiety. The donor fluorescent moiety is excited by light of appropriate wavelength and intensity within the donor fluorescent moiety's excitation spectrum and under conditions in which direct excitation of the acceptor fluorophore is minimized. The donor fluorescent moiety then transfers the absorbed energy by non-radiative means to the acceptor, which subsequently re-emits some of the absorbed energy as fluorescence emission at a characteristic wavelength. FRET applications can include TR-FRET applications. In these embodiments, a Ln complex, such as a Eu or Tb metal chelate, is used as a fluorescent donor moiety, as described above. Typically, the Ln complex is chosen so that one of its emission bands overlaps with an excitation band of the acceptor fluorescent moiety.

FRET can be manifested as a reduction in the intensity of the fluorescent signal from the donor, reduction in the lifetime of its excited state, and/or an increase in emission of fluorescence from the acceptor fluorescent moiety. When a peptide having a donor fluorescent moiety and acceptor fluorescent moiety is cleaved, the donor fluorescent moiety and the acceptor fluorescent moiety physically separate, and FRET is diminished or eliminated. Under these circumstances, fluorescence emission from the donor increases and fluorescence emission from the acceptor decreases. Accordingly, a ratio of emission amplitudes at wavelengths characteristic (e.g., the emission maximum) of the donor relative to the acceptor should increase as compared to the same ratio under FRET conditions (e.g., when emission of the donor is quenched (e.g., reduced) by the acceptor).

The efficiency of FRET is dependent on the separation distance and the orientation of the donor fluorescent moiety and acceptor fluorescent moiety, the fluorescent quantum yield of the donor moiety, and the spectral overlap with the acceptor moiety. Forster derived the relationship:

$$E = (F^\circ - F)/F^\circ = Ro^6/(R^6 + Ro^6)$$

where E is the efficiency of FRET, F and $F^\circ$ are the fluorescence intensities of the donor in the presence and absence of the acceptor, respectively, and R is the distance between the donor and the acceptor. Ro, the distance at which the energy transfer efficiency is 50% of maximum is given (in Å) by:

$$Ro = 9.79 \times 10^3 (K^2 Q J n^{-4})^{1/6}$$

where $K^2$ is an orientation factor having an average value close to 0.67 for freely mobile donors and acceptors, Q is the quantum yield of the unquenched fluorescent donor, n is the refractive index of the intervening medium, and J is the overlap integral, which expresses in quantitative terms the degree of spectral overlap. The characteristic distance Ro at which FRET is 50% efficient depends on the quantum yield of the donor, the extinction coefficient of the acceptor, the overlap between the donor's emission spectrum and the acceptor's excitation spectrum, and the orientation factor between the two fluorophores.

Changes in the degree of FRET can be determined as a function of a change in a ratio of the amount of fluorescence from the donor and acceptor moieties, a process referred to as "ratioing." By calculating a ratio, the assay is less sensitive to, for example, well-to-well fluctuations in substrate concentration, photobleaching and excitation intensity, thus making the assay more robust. This is of particular importance in automated screening applications where the quality of the data produced is important for its subsequent analysis and interpretation.

For example, in some embodiments of the method, a ratiometric analysis is performed, wherein a ratio of fluorescence emission at two different wavelengths is compared between a protease mixture and a control mixture. In a typical FRET-based assay, the two wavelengths can correspond to the emissions maxima for two detectable (e.g., fluorescent) moieties of the composition. Thus, if a composition is a substrate for a kinase, the phosphorylated composition will be less susceptible to cleavage by a protease. Accordingly, the phosphorylated composition will maintain FRET between the donor and acceptor moieties (e.g., the FRET pair), resulting in a low emissions ratio of the donor to the acceptor moiety. A control sample in such a case, however, will be subject to cleavage by the protease. Cleavage disrupts FRET between the donor and acceptor moieties, leading to a larger emissions ratio of the donor to the acceptor moiety. In some embodiments, the emissions ratio of the control mixture will be more than 1.5, 2, 3, 4, 5, 7, 10, 15, 20, 25, 30, 40, 50, or 100 times larger than the emissions ratio of a protease mixture.

The present invention can also be used to determine whether a sample (e.g., a cell, an extract, a purified protein, a tissue, an organism) has general kinase or phosphatase activity or a specific kinase or specific phosphatase activity, e.g., abl-1 kinase activity. The method typically involves contacting a sample with a composition of matter (e.g., under appropriate conditions to enable phosphorylation (or dephosphorylation) of the composition), and then contacting the sample and composition mixture with a protease, e.g., a protease known to cleave the composition in the absence of the post-translational modification. The degree of post-translational modification activity in the sample is assessed, e.g., as described above, such as by monitoring a measurable property of the sample-composition mixture and comparing it to the measurable property of a control mixture.

In some cases, a composition and a protease may be added to a sample at the same time. Alternatively, in the case where a sample contains cells, the method would typically involve stimulation of the cells and then either lysing the cells in the presence of the composition or, in the case where the composition is expressed within the cells, lysing the cells in the presence of a protease to measure composition modification.

In some dark quenching RET applications, a composition comprises one member of a dark quenching pair (e.g., a fluorescent moiety (e.g., a donor) or a dark quencher moiety (e.g., acceptor)) and a first binding member coupled to the peptide such that a motif and protease site are located between them. A probe composition can contain the complementary member of the dark quenching pair. In some dark quenching RET applications, a composition comprises one member of a dark quenching pair (e.g., a fluorescent moiety (e.g., a donor) or a dark quencher moiety (e.g., acceptor) coupled to the peptide such that a motif and protease site are located between them. In this case, cleavage of the peptide by a protease results in an alteration in energy transfer between the first fluorescent moiety and the dark quencher moiety that may be used to monitor post-translational activity. A fluorescent moiety and dark quencher moiety are typically chosen such that the absorption spectrum of the dark quencher (the acceptor moiety) overlaps with the emission spectrum of the donor fluorescent moiety. The donor fluorescent moiety is excited by light of appropriate intensity within the donor fluorescent moiety's excitation spectrum. The donor fluorescent moiety then transfers the absorbed energy by non-radiative means to the dark quencher, which in this case does not re-emit a substantial amount of the absorbed energy as light (e.g., forming a dark quenching RET pair). Dark quenching RET can be manifested as a reduction in the intensity of a fluorescent signal from a donor or a reduction in the lifetime of its excited state. When a peptide that connects a member of a dark quenching RET pair and a first binding member is cleaved, the fluorescent moiety and the binding member physically separate, and dark quenching RET is diminished or eliminated. Under these circumstances, fluorescence emission from the donor fluorescent moiety increases.

Methods of the present invention also take advantage of resonance energy transfer (RET) between a donor moiety (e.g., a luminescent metal chelate) and an acceptor moiety (e.g., a fluorescent acceptor moiety). In these cases, a composition typically includes one or two members of a RET (e.g., TR-RET) pair (e.g., a donor luminescent metal complex or an acceptor fluorescent moiety) coupled to the peptide such that a motif and a protease site are located between them. In some embodiments, one member of the RET pair is coupled via a binding member and the probe composition includes the complementary member of the RET (e.g., TR-RET) pair.

The donor moiety (e.g., a luminescent metal chelate) is excited by light of appropriate wavelength and intensity (e.g., within the donor antenna moiety's excitation spectrum) and under conditions in which direct excitation of the acceptor fluorophore is minimized. The donor moiety (e.g., a luminescent chelate) then transfers the absorbed energy, e.g., by non-radiative means to the acceptor moiety (e.g., fluorescent), which subsequently re-emits some of the absorbed energy, e.g., as fluorescence emission at one or more characteristic wavelengths. In TR-RET applications, the re-emitted radiation is not measured until after a suitable delay time, e.g., 25, 50, 75, 100, 150, 200, or 300 microseconds to allow decay of background fluorescence, light scattering, or other luminescence, such as that caused by the plastics used in microtiter plates.

In some embodiments, cleavage of the peptide by a protease results in a physical separation of the first binding member from the RET (e.g., TR-RET) detectable moiety, leading to an alteration (e.g., reduction or diminishing) in energy transfer between the donor moiety (e.g., luminescent metal complex) and the acceptor moiety (e.g., fluorescent acceptor moiety).

TR-RET can be manifested as a reduction in the intensity of a luminescent signal from a donor moiety (e.g., a luminescent metal complex) and/or an increase in emission of fluorescence from the acceptor fluorescent moiety. Under conditions where a peptide is cleaved, luminescence emission from the donor moiety (e.g., a luminescent metal complex) increases and fluorescence emission from the acceptor fluorescent moiety decreases. Accordingly, a ratio of emission amplitudes at wavelengths characteristic (e.g., the emission maximum) of the donor moiety (e.g., a luminescent metal complex) relative to the acceptor fluorescent moiety can be compared to the same ratio under RET conditions (e.g., when emission of the donor luminescent metal complex is quenched by the acceptor).

One application of the assay is to either introduce or express the composition in living eukaryotic or prokaryotic cells to enable the measurement of intracellular post-translational activities. In one aspect, the method would involve a composition comprising a first fluorescent protein, a peptide containing a motif (e.g., a recognition motif) and a protease site, and a second fluorescent protein fused together as a single polypeptide chain. In this case the first fluorescent protein and the second fluorescent protein would be selected to enable FRET to occur as described above. A pair of functional engineered fluorescent proteins for example would be, Topaz (S65G, S72A, K79R, T203Y) and W1B (F64L, S65T, Y66W, N1461, M153T, V163A), as shown in Table 7 of U.S. Pat. No. 6,410,255.

In another aspect, a method can involve a composition comprising a peptide containing one or more binding sites for a fluorescent moiety, a motif (e.g., a recognition motif), and a protease cleavage site. For example, a binding site could comprise a sequence that recognizes a fluorescent moiety, as described in pending U.S. patent application Ser. No. 08/955,050, filed Oct. 21, 1997, entitled Methods of Using Synthetic Molecules and Target Sequences; Ser. No. 08/955,859, filed Oct. 21, 1997, entitled Synthetic Molecules that Specifically React with Target Sequences; and Ser. No. 08/955,206, filed Oct. 21, 1997, entitled Target Sequences for Synthetic Molecules. In this case, expression of a peptide comprising a recognition motif, protease cleavage site, and binding site could be accomplished using genetic means as described above. The addition of a membrane-permeable fluorescent moiety capable of binding to the binding site would enable the creation in situ of composition according to the present invention.

Another application of the method is to use inducible controlling nucleotide sequences to produce a sudden increase in the expression of either a composition, a kinase or phosphatase, or a protease, e.g., by inducing expression of a construct. A suitable protease could be expressed within a cell, or induced, or introduced using a membrane-translocating sequence (see U.S. Pat. No. 5,807,746, issued Sep. 15 1998 to Lin et al.) The efficiency of FRET may be typically monitored at one or more time intervals after the onset of increased expression of a protease.

In BRET applications, a composition typically comprises a luminescent moiety and a fluorescent moiety coupled to a peptide such that a motif and protease site are located between them. In this case, cleavage of the peptide by a protease results in an alteration in energy transfer between the luminescent moiety and the fluorescent moiety that may be used to determine kinase or phosphatase activity, as described above. In this case, the luminescent and fluorescent moieties are typically chosen such that the emission spectrum of the luminescent moiety overlaps with the excitation spectrum of the fluorescent moiety. Because a luminescent moiety provides light through a chemiluminescent, electroluminescent, or bioluminescent reaction, there is no requirement for direct light excitation to create the excited state in the luminescent moiety. Instead, appropriate substrates or a voltage must be provided to (or applied to) the luminescent moiety to create an excited state luminescent moiety. In the case of bioluminescent proteins, such substrates are generically referred to as luciferins (for example, see U.S. Pat. No. 5,650,289 issued Jul. 22, 1997 to Wood). If BRET occurs, the energy from the excited state of a luminescent moiety is transferred to a fluorescent moiety by non-radiative means, rather than being emitted as light from the luminescent moiety. Because luminescent and fluorescent moieties typically are chosen to emit light at characteristic wavelengths, an emission ratio of the two can also provide a ratiometric readout as described for the FRET based applications above. BRET can be manifested as a reduction in the intensity of a fluorescent signal from the luminescent moiety, a reduction in the lifetime of its excited state, and/or an increase in emission of fluorescence from the fluorescent moiety. When a peptide substrate that connects a luminescent moiety and a fluorescent moiety is cleaved, the luminescent moiety and the fluorescent moiety physically separate, and BRET is diminished or eliminated. Under these circumstances, light emission from the luminescent moiety increases and fluorescence emission from the fluorescent moiety decreases. The efficiency of BRET is typically dependent on the same separation and orientation factors as described above for FRET.

In dark quenching RET applications, a composition typically comprises, a first fluorescent moiety (e.g., a donor) and a dark quencher moiety (e.g., acceptor) coupled to the peptide such that a motif and protease site are located between them. In this case, cleavage of the peptide by a protease results in an alteration in energy transfer between the first fluorescent moiety and the dark quencher moiety that may be used to monitor post-translational activity. A fluorescent moiety and dark quencher moiety are typically chosen such that the absorption spectrum of the dark quencher (the acceptor moiety) overlaps with the emission spectrum of the donor fluorescent moiety. The donor fluorescent moiety is excited by light of appropriate intensity within the donor fluorescent moiety's excitation spectrum. The donor fluorescent moiety then transfers the absorbed energy by non-radiative means to the dark quencher, which in this case does not re-emit a substantial amount of the absorbed energy as light (e.g., forming a dark quenching RET pair). Dark quenching RET can be manifested as a reduction in the intensity of a fluorescent signal from a donor or a reduction in the lifetime of its excited state. When a peptide that connects a donor fluorescent moiety and a dark quencher moiety is cleaved, the donor fluorescent moiety and the dark quencher moiety physically separate, and dark quenching RET is diminished or eliminated. Under these circumstances, fluorescence emission from the donor fluorescent moiety increases.

Another mechanism of quenching contemplated in the present invention involves the formation and detection of an excitonic dimer (e.g., static quenching) between a fluorophore and a quencher. Typically, static quenching results when the interaction of a fluorophore with a quencher forms a stable non-fluorescent or weakly fluorescent ground state complex. Since this complex typically has a different absorption spectrum from the fluorophore, the presence of an absorption change is diagnostic of this type of quenching (in contrast, collisional quenching is a transient excited state interaction and therefore does not affect the absorption spectrum). Pure static quenching can reduce the intensity of fluorescence but does not necessarily decrease the measured lifetime of emission.

In magnetic detection-based assays, a composition typically comprises a metal chelate or metal particle, as described above, coupled to a peptide having a motif (e.g., a recognition motif) and a protease site. In these cases, the metal chelate or particle should be chosen to have a characteristic magnetic signal, e.g., $T_1$, $T_2$, or $R_1$, that will change when it is bound or associated with the intact peptide as compared to the cleaved peptide. Cleavage of the peptide by a protease results in an alteration in the magnetic signal that may be used to monitor post-translational activity.

In radio-isotope detection-based assays, a composition typically comprises a radioisotope (e.g., a radiolabel such as $^{32}P$, $^{35}S$, $^{3}H$, $^{14}C$ or others known to those of skill in the art) coupled to a peptide having a motif (e.g., a recognition motif) and a protease site. In these cases, monitoring of a location of a radiolabel (e.g., in a gel) or monitoring of a size of a cleavage product (e.g., in a gel) before and after proteolytic cleavage provides a method for monitoring post-translational activity.

The assays of the present invention can be used in drug screening assays to identify compounds that alter or modulate a kinase or phosphatase activity. In one embodiment, an assay is performed on a sample in vitro (e.g. in a sample isolated from a cell, or a cell lysate, or a purified or partially-purified enzyme) containing an activity for which a drug screen is desired. A sample containing a known amount of activity is contacted with a composition of the invention and with a test compound. The activity of the sample is monitored after addition of a protease, as described above, for example, by monitoring a measurable property of the composition. A measurable property of the sample in the presence of the test compound can be compared with the measurable property of a sample similarly treated in the absence of the test compound (e.g., the control reaction). A difference indicates that the test compound alters the activity. In preferred embodiments, the method is used to evaluate putative inhibitors of a kinase or phosphatase activity.

In another embodiment, an ability of a test compound to alter or to modulate a kinase or phosphatase activity in a cell-based assay may be determined. In these assays, cells transfected with an expression vector encoding a composition of the invention, as described above, are exposed to different amounts of the test compound, and the effect on a measurable property (e.g., an optical property such as FRET or fluorescence polarization) in each cell can be determined after induction or introduction of a suitable protease. Typically, as with any method of the present invention, the change in the measurable property is compared to that of untreated controls.

Any of the methods of the present invention can be modified to be performed in a high-throughput or ultra-high-throughput manner. For example, a method to identify a substrate of a particular kinase or phosphatase may be modified to contact a plurality of compositions (e.g., two or more different compositions), independently, with a particular kinase or phosphatase enzyme, to form a plurality of enzyme mixtures. Each enzyme mixture is treated with a protease, and a measurable property of each protease mixture is monitored and compared to an appropriate control sample. Similarly, a particular composition can be evaluated for its suitability as a substrate of a plurality of kinases or phosphatases (e.g., two or more different kinases or phosphatases). Thus, a particular composition of matter may be contacted, independently, with a plurality of enzymes to form a plurality of enzyme mixtures. Each mixture is treated with a protease and a measurable property of each protease mixture is monitored and compared to an appropriate control sample. As one of skill in the art will appreciate, such high-throughput methods are particularly amenable to multi-well plate or 2-D array panel formats, wherein a plurality of compositions are screened for suitability as substrates for a plurality of different enzymes. See Example 4, below. Devices for incubating and monitoring multi-well plates are known in the art. Similar panel assays may be envisioned for methods to identify modulators of a kinase or phosphatase activity. See Example 3, below.

In another embodiment, a plurality of different compositions of matter may be contacted simultaneously with a single kinase or phosphatase; the reaction mixture may then be contacted with a protease; and a plurality of measurable properties may be monitored and compared to the measurable properties of an appropriate control sample. Typically, each of the compositions of matter comprises a FRET pair having a characteristic excitation wavelength of the donor and emissions ratio of the donor to the acceptor, so that each FRET pair can be tracked independently of the others. An appropriate control sample would include the plurality of compositions of matter treated with the protease in the absence of the kinase, phosphatase, and/or ATP. As one of skill in the art will recognize, other measurable properties can be similarly monitored to facilitate the use of such a method with detectable moieties for dark quenching RET and magnetic detection applications.

Alternatively, arrays of compositions having known recognition motifs may be created in order to create an activity profile of kinase or phosphatase activities in a sample. In this case, screening of the array is used to characterize the activities within a sample by incubating the array with a sample containing the activities, adding an appropriate protease, and then monitoring a measurable property from each member of the array. Those array members that are more efficiently modified after exposure to the sample may be identified by the degree to which the measurable property of that array member is altered as compared to the appropriate control samples.

The dynamic range, quality, and robustness of the methods of the present invention can be evaluated statistically. For example, the Z'-Factor is a statistic designed to reflect both assay signal dynamic range and the variation associated with signal measurements. Signal-to-noise (S/N) or signal-to-background (S/B) ratios alone are unsatisfactory in this regard because they do not take into account the variability in sample and background measurements and signal dynamic range. The Z'-Factor takes into account these factors, and because it is dimensionless, it can be used to compare similar assays. The relationship of Z'-factor values to assay quality are summarized in Table 6, below. Typically, assays of the present invention yield Z'-factors of greater than or equal to 0.5.

A Z'-factor may be determined by evaluating the dynamic range of a method. In some embodiments, the dynamic range may be defined by 0% inhibition and 100% inhibition controls. A 0% inhibition control is performed by contacting a composition of the present invention with a kinase and ATP to form a kinase mixture, contacting the kinase mixture with a protease to form a protease mixture, and monitoring a measurable property of the protease mixture. A measurable property can be an emissions ratio, such as the ratio of coumarin emission at 445 nm to fluorescein emission at 520 nm. Typically, the reaction conditions of the kinase reaction are chosen to phosphorylate about 10-40% of the composition in a predetermined time period (e.g., 30 mins., 1 hr., 2 hr., or 4 hr.). The % phosphorylation of a sample can be calculated by using the following equation:

% Phosphorylation=1−[((Emission Ratio×$Fc$)−$Fa$)/
(($Fb$−$Fa$)+(Emission Ratio×($Fc$−$Fd$)))]

where Emission Ratio is the ratio of donor emission signal to acceptor emission signal, as indicated above; Fa is the average donor emission signal of the 100% phosphorylation control; Fb is the average donor emission signal of the 0% phosphorylation control; Fc is the average acceptor emission signal of the 100% phosphorylation control; and Fd is the average acceptor emission signal of the 0% phosphorylation control.

The 100% inhibition control is performed similarly, but in the absence of ATP (100% inhibition of the kinase), to yield 0% phosphorylated composition. A 100% phosphorylated composition can also be included as a control. Both 0% and 100% inhibition controls can be performed in duplicate. The Z'-factor is then calculated as follows:

Z'-factor=(1−(3×σ0% inhibition)+(3×σ100% inhibition))/(μ of 100% inhibition−μ of 0% inhibition)

TABLE 6

| Z'-factor value | Relation to Assay Quality |
|---|---|
| 1 | Excellent Assay |
| 1 > Z' ≧ 0.5 | An excellent assay |
| 0.5 > Z' > 0 | A double assay |
| 0 | A "yes/no" type assay |
| <0 | Assay unreliable |

The methods of the present invention can be used with various systems for spectroscopic measurement. In one embodiment, the system comprises 1) a reagent for an assay and 2) a device comprising at least one plate (e.g., a multi-well plate) or container and a platform, such as a multi-well plate platform, e.g., for incubating and/or detecting a signal from the plate or container. The system can further comprise a detector, such as a detector appropriate for detecting a signal from a sample or a plate. The system can comprise multiple plates or containers or multi-well platforms. In this context, a reagent for an assay includes any reagent useful to perform biochemical or biological in vitro or in vivo testing procedures, such as, for example, buffers, co-factors, proteins such as enzymes or proteases, carbohydrates, lipids, nucleic acids, active fragments thereof, organic solvents such as DMSO, chemicals (e.g., ATP), analytes, therapeutics, compositions, cells, antibodies, ligands, and the like. In this context, an active fragment is a portion of a reagent that has substantially the activity of the parent reagent.

The compositions of the present invention are suited for use with systems and methods that utilize automated and integratable workstations for identifying substrates and modulators of kinase or phosphatase activity. Such systems are described generally in the art (see U.S. Pat. No. 4,000,976 to Kramer et al. (issued Jan. 4, 1977), U.S. Pat. No. 5,104,621 to Host et al. (issued Apr. 14, 1992), U.S. Pat. No. 5,125,748 to Bjornson et al. (issued Jun. 30, 1992), U.S. Pat. No. 5,139,744 to Kowalski (issued Aug. 18, 1992), 5,206,568 to Bjornson et al. (issued Apr. 27, 1993), U.S. Pat. No. 5,350,564 to Mazza et al. (Sep. 27, 1994), U.S. Pat. No. 5,589,351 to Harootunian (issued Dec. 31, 1996), and PCT Application Nos. WO 93/20612 to Baxter Deutschland GMBH (published Oct. 14, 1993), WO 96/05488 to McNeil et al. (published Feb. 22, 1996), WO 93/13423 to Agong et al. (published Jul. 8, 1993) and PCT/US98/09526 to Stylli et al., filed May 14, 1998).

For some embodiments of the invention, particularly for plates with 96, 192, 384, 864 and 3456 wells per plate, detectors are available for integration into the system. Such detectors are described in U.S. Pat. No. 5,589,351 (Harootunian), U.S. Pat. No. 5,355,215 (Schroeder), and PCT patent application WO 93/13423 (Akong). Alternatively, an entire plate may be "read" using an imager, such as a Molecular Dynamics FluorImager 595 (Sunnyvale, Calif.). Multi-well platforms having greater than 864 wells, including 3,456 wells, can also be used in the present invention (see, for example, PCT Application PCT/US98/11061, filed Jun. 2, 1998).

In another embodiment, the system may comprise a two dimensional array of compositions dispersed on a substratum (e.g., a multi-well plate), for example as described in U.S. Pat. No. 4,216,245 issued Aug. 5, 1980 to Johnson, U.S. Pat. No. 5,721,435 issued Feb. 24, 1998 to Troll, and U.S. Pat. No. 5,601,980 issued Feb. 11, 1997 issued to Gordon et al. Such a system provides the ability to rapidly profile large numbers of compositions and or large numbers of samples in a simple, miniaturized high throughput format.

The present invention also provides articles of manufacture, such as kits. Typically, a kit includes a container and a composition of matter of the present invention. In some embodiments, a kit can include one or more of the following: a multi-well plate, a protease, one or more enzymes (kinase or phosphatase enzymes), buffers, a source of ATP, and directions for use of the kit. A kit can be useful for determining substrates of kinase or phosphatase activity or for identifying a modulator of a kinase or phosphatase activity.

EXAMPLES

Example 1

Determination of Kinase Kinetic Parameters with Kinase Substrates a. Determination of Kinetic Parameters for Akt 1 Kinase, a Serine/Threonine Kinase ATP was serially diluted in a Corning 384-well round bottom non-binding surface plate. A substrate for Akt 1, SEQ ID NO: 59 modified by having a 7-hydroxycoumarin moiety conjugated to the ε-NH2 of the C-terminal lysine and a 5-FAM moiety conjugated to an N-terminal GABA linker, prepared as described in U.S. Pat. No. 6,410,255, was mixed with Akt 1 kinase and added to the ATP dilutions. The final concentration of SEQ ID NO: 59 was 2 µM in each well; the final concentration of Akt1 was 16 nM. The plates were allowed to incubate at room temperature for 1 hour. Chymotrypsin was then added to each well (final concentration 100 ng/ml) and the plates allowed to incubate for 1 hour at room temperature. The plate was read using a TECAN SAFIRE™ monochromator-based fluorescence plate reader (Excitation at 400 nm (12 nm bandwidth); Emission at 445 nm (12 nm bandwidth); and Emission at 520 nm (12 nm bandwidth). Curve fitting and data presentation were performed using Prism™ software from GraphPad Software, Inc. The apparent Km was 15 µM.

b. Determination of Kinetic Parameters for Abl 1 Kinase, a Tyrosine Kinase

ATP was serially diluted (0.8 µM to 100 µM) in a Corning 384-well round bottom non-binding surface plate. A substrate for Abl 1, SEQ ID NO: 3 modified by having a 7-hydroxycoumarin moiety conjugated to the ε-NH2 of the C-terminal lysine and a 5-FAM moiety conjugated to an N-terminal GABA linker, prepared as described in U.S. Pat. No. 6,410,255, was mixed with Abl 1 kinase and added to the ATP dilutions. The final concentration of SEQ ID NO: 3 was 2 µM in each well; the final concentration of Abl-1 was 16 nM. The plates were allowed to incubate at room temperature for 1 hour. Chymotrypsin was then added to each well (final concentration 1.25 ng/ml) and the plates allowed to incubate for 1 hour at room temperature. The plate was read using a TECAN SAFIRE™ monochromator-based fluorescence plate reader (Excitation at 400 nm (12 nm bandwidth); Emission at 445 nm (12 nm bandwidth); and Emission at 520 nm (12 nm bandwidth). Curve fitting and data presentation were performed using Prism™ software from GraphPad Software, Inc. As can be seen from FIG. 3, the Vmax of Abl 1 kinase with SEQ ID NO: 3 is 7%, corresponding to 0.02 pmol/min, and the apparent Km is 7 µM. See FIG. 3.

Example 2

Dependence of Percent Phosphorylation on Kinase Concentration and Evaluation of Z'-Factor Values a. Akt 1

Akt 1 kinase was serially diluted in a 384 well plate (final concentration ranging from 156 ng/ml to 20,000 ng/ml). Kinase reactions were initiated by the addition of a solution of Akt 1 substrate, SEQ ID NO: 59 (modified as described in Example 1a above; 2 µM final concentration), and ATP (15 µM final concentration). The plates were allowed to incubate at room temperature for 1 hour. Chymotrypsin was then added to each well (final concentration 100 ng/ml) and the plates allowed to incubate for 1 hour at room temperature. The plate was read using a TECAN SAFIRE™ monochromator-based fluorescence plate reader (Excitation at 400 nm (12 nm bandwidth); Emission at 445 nm (12 nm bandwidth); and Emission at 520 nm (12 nm bandwidth). Curve fitting and data presentation were performed using Prism™ software from GraphPad Software, Inc.

% phosphorylation data are set forth in FIG. 4. Z'-factor values for varying kinase concentrations and % phosphorylation of the substrate are demonstrated in Table 7 below. High Z'-factor values are seen when even as little as 10% of the substrate is phosphorylated.

TABLE 7

Z'-Factor Values for Akt 1

| ng Akt 1 kinase per well | % Phosphorylation | Z'-factor value |
| --- | --- | --- |
| 5.0 | 8 | 0.78 |
| 10.0 | 12 | 0.88 |
| 25.0 | 20 | 0.91 |
| 37.5 | 28 | 0.92 |
| 42.0 | 30 | 0.92 |
| 50.0 | 33 | 0.93 |
| 75.0 | 38 | 0.93 |
| 100.0 | 43 | 0.92 |
| 150.0 | 50 | 0.90 | b. Abl 1

Abl 1 kinase was serially diluted in a 384 well plate (final concentration ranging from 4.9 ng/ml to 10,000 ng/ml). Kinase reactions were initiated by the addition of a solution of Abl 1 substrate, SEQ ID NO: 3 (modified as described in Example 1b above; 2 µM final concentration), and ATP (7 µM final concentration). The plates were allowed to incubate at room temperature for 1 hour. Chymotrypsin was then added to each well and the plates allowed to incubate for 1 hour at room temperature. The plate was read using a TECAN SAFIRE™ monochromator-based fluorescence plate reader (Excitation at 400 nm (12 nm bandwidth); Emission at 445 nm (12 nm bandwidth); and Emission at 520 nm (12 nm bandwidth). Curve fitting and data presentation were performed using Prism™ software from GraphPad Software, Inc.

% phosphorylation data are set forth in FIG. 5. Z'-factor values for varying kinase concentrations and % phosphorylation of the substrate are demonstrated in Table 8 below. High Z'-factor values are seen when even as little as 10% of the substrate is phosphorylated.

TABLE 8

Z'-Factor Values for Abl 1 Assay

| ng Abl 1 kinase per well | % Phosphorylation | Z'-factor value |
| --- | --- | --- |
| 0.50 | 10 | 0.72 |
| 0.75 | 15 | 0.79 |
| 1.00 | 23 | 0.84 |
| 1.30 | 30 | 0.85 |
| 1.50 | 35 | 0.86 |
| 2.00 | 46 | 0.93 |
| 2.50 | 53 | 0.94 |

TABLE 8-continued

Z'-Factor Values for Abl 1 Assay

| ng Abl 1 kinase per well | % Phosphorylation | Z'-factor value |
|---|---|---|
| 3.00 | 61 | 0.94 |
| 3.50 | 79 | 0.95 | c. PKA and PKCα Kinases

Experiments similar to those outlined above were performed for 8 compositions of matter (SEQ ID NOs: 47, 50, 43, 58, 59, 60, 63, and 68) against PKA and PKCα. FIG. 8 demonstrates the % phosphorylation by the serine/threonine kinase PKA of the 8 compositions against which it was screened. As shown, SEQ ID NO: 47 modified as described, is the best substrate for the kinase because it yielded maximal phosphorylation even at low kinase concentrations.

FIG. 9 demonstrates the % phosphorylation by PKCα of the 8 compositions against which it was screened. As shown, only SEQ ID NO: 60 modified as described, is phosphorylated by this S/T kinase.

Example 3

Identifying Modulators of Kinase Activity a. Abl 1 (Tyrosine Kinase) Inhibitors

Two test compounds (Staurosporine and Genistein, available from Calbiochem) were evaluated for their ability to inhibit phosphorylation of an Abl 1 substrate (SEQ ID NO: 3, modified as described in Example 1b above) by Abl 1. Serial dilutions of the respective test compound (final concentration ranging from 0.3 to 500,000 nM) were dispensed in 384 well plates. 5 μL of an Abl 1 kinase/Abl 1 substrate solution (final concentration of 1.5 ng Abl 1/well and 2 μM of Abl 1 substrate/well) were added to each well, along with 2.5 μl, of ATP (final concentration of 10 μM). The plate was mixed and incubated for 1 hour at room temperature. 5 μL of chymotrypsin were added to each well (final concentration of 1 μg/mL), and the plate mixed and allowed to incubate at room temperature for 1 hour. The plate was read using a TECAN SAFIRE™ monochromator-based fluorescence plate reader (Excitation at 400 nm (12 nm bandwidth); Emission at 445 nm (12 nm bandwidth); and Emission at 520 nm (12 nm bandwidth). Curve fitting and data presentation were performed using Prism™ software from GraphPad Software, Inc.

The dynamic range of the Abl 1 assay was defined by performing 0% and 100% inhibition controls. The 0% inhibition control phosphorylated 30% of the Abl 1 substrate, while the 100% inhibition control was a kinase reaction done in the absence of ATP, resulting in nonphosphorylated Abl 1 substrate. As a nonphosphorylated Abl1 substrate is cleaved completely by chymotrypsin, it will exhibit a loss of FRET and a concomitant increase in the Emissions ratio at 445 nm (coumarin)/520 nm (fluorescein).

FIG. 6 demonstrates the inhibition curves by Staurosporine and Genistein for phosphorylation of the Abl 1 substrate by Abl 1. An $IC_{50}$ value is defined as the inhibitor concentration that produces a half-maximal shift in the same Emissions ratio. Error bars on FIG. 6 represent one standard deviation from the mean of three replicates. As can be seen from FIG. 6, the $IC_{50}$ is 33 nM for Staurosporine and 4.1 μM for Genistein.

b. Akt 1 (Serine/Threonine Kinase) Inhibitors

Two test compounds (Staurosporine and Ro-31-8220 (available from Calbiochem) were evaluated for their ability to inhibit phosphorylation of an Akt 1 substrate (SEQ ID NO: 59, modified as described in Example 1a above) by Akt 1. Serial dilutions of the respective test compound (final concentration ranging from 0.019 to 50,000 nM) were dispensed in 384 well plates. 5 μL of an Akt 1 kinase/Akt 1 substrate solution (final concentration of 42 ng Akt 1/well and 2 μM of Akt 1 substrate/well were added to each well, along with 2.5 μL of ATP (final concentration of 10.5 μM). The plate was mixed and incubated for 1 hour at room temperature. 5 μL of chymotrypsin were added to each well (final concentration of 100 ng/mL), and the plate mixed and allowed to incubate at room temperature for 1 hour. The plate was read using a TECAN SAFIRE™ monochromator-based fluorescence plate reader (Excitation at 400 nm (12 nm bandwidth); Emission at 445 nm (12 nm bandwidth); and Emission at 520 nm (12 nm bandwidth). Curve fitting and data presentation were performed using Prism™ software from GraphPad Software, Inc.

The dynamic range of the Akt 1 assay was defined by performing 0% and 100% inhibition controls. The 0% inhibition control phosphorylated 30% of the Akt 1 substrate, while the 100% inhibition control was a kinase reaction done in the absence of ATP, resulting in nonphosphorylated Akt 1 substrate. As a nonphosphorylated Akt 1 substrate is cleaved completely by chymotrypsin, it will exhibit a loss of FRET and a concomitant increase in the Emissions ratio at 445 nm (coumarin)/520 nm (fluorescein).

FIG. 7 demonstrates the inhibition curves by Staurosporine and Ro-31-8220 for phosphorylation of the Akt 1 substrate by Akt 1. An $IC_{50}$ value is defined as the inhibitor concentration that produces a half-maximal shift in the same Emissions ratio. Error bars on FIG. 7 represent one standard deviation from the mean of three replicates. As can be seen from FIG. 7, the $IC_{50}$ is 17.2 nM for Staurosporine and 408 nM for Ro-31-8220.

The experiment was repeated using 15 μM ATP and 3 ng/well Akt 1 and was also successful.

Example 4

Panel Assays for Evaluating Substrates for Kinases

Compositions are screened against S/T and Y kinases in a series of multi-well (96 or 384 well) plate formats to evaluate their suitability as substrates for serine/threonine kinases and/or tyrosine kinases. Each composition has a 7-hydroxycoumarin moiety conjugated to the ε-NH2 of the C-terminal lysine and a 5-FAM moiety conjugated to an N-terminal GABA linker.

The following kinases are screened: Akt1, Akt2, Akt3, Aurora A, CaMKII, CDK2/CycA, CDK3/CycE, CDK7/CycH, MAPKAP-K1α, MAPKAP-K1β, MAPKAP-K1γ, MSK1, PAK2, PKA, PKG, ROCK, ROCK2, CDK2/CycA, CDK3/CycE, ERK1, ERK2, IKKα, IKKβ, p38β, p38γ, p38δ, REDK, AMPK, CDK6, MAPKAP-K2, MAPKAP-K3, MAPKAP-K5, SGK1, PIM1, CHK1, CHK2, PKCα, PKCβI, PKCβII, PKCγ, PKCδ, PKCε, PKCζ, PKCη, PKCθ, PKCι, and p70 S6 Kinase, Abl1, Abl2, BMX, CSF1R, Csk, EphB4, Fes/Fps, FGFR1, FGFR4, Fgr, FLT3, Fyn, Hck, IGF1R, IRKβ, ITK, Jak3, KDR, c-KIT, Lck, Lyn A, Lyn B, c-MET, Src, Src N1, Src N2, SYK, TIE2, TRKa, YES, CK1δ, IKKα, IKKβ, IRTK, CDK1, CDK5/p35, MEK1, MEK5, MEK2, MKK3, MKK4, MKK7, RAF1, GSK3α, GSK3β, MEKK1, CK1δ, CK-1α, CKIIα, JNK1, JNK2, JNK3, and EGFR.

A 384 multiwell plate defines a matrix as follows: each of columns 1-20 of the plate correspond to a particular kinase, while rows 1-16 in each kinase column correspond to duplicate samples of 8 different compositions of matter that are potential kinase substrates. Columns 21-24 correspond to control columns, representing 0% phosphorylated controls (100% inhibition of kinase, no ATP), and 100% phosphorylated control (e.g., synthetic phosphorylated composition). For a set of 20 kinases, 5 µl of 2× final concentration of each kinase are dispensed to each row of the respective kinase column of the plate. 5 µL of kinase buffer are added to control columns 21-24. Each of the compositions of matter and ATP are then added to the appropriate rows of each kinase column to result in a final concentration of 2 µM composition/0.8 µM ATP per well; these samples are prepared in duplicate. The compositions of matter are also added to the appropriate rows of control columns 23 and 24 to result in a final concentration of 2 µM unphosphorylated composition. Phosphorylated compositions of matter are added to the appropriate rows of columns 21 and 22 to result in a final concentration of 2 µM phosphorylated composition. The plate is then mixed on a shaker and incubated for 1 hour at room temperature to allow kinase reactions to proceed. 5 µL of chymotrypsin are then added to each well. The plate is mixed on a plate shaker and incubated for 1 hour at room temperature. The plate is read using a TECAN SAFIRE™ monochromator-based fluorescence plate reader (Excitation at 400 nm (12 nm bandwidth); Emission at 445 nm (12 nm bandwidth); and Emission at 520 nm (12 nm bandwidth). Similar assays with varying kinase concentrations are also performed.

Example 5

Phosphatase Assays 8 compositions of matter were screened against 6 phosphatases to evaluate their suitability as substrates for phosphatases. The compositions corresponded to SEQ ID NOs: 31, 97, 100, 103, 109, 110, 113, and 118, with each peptide having a 7-hydroxycoumarin moiety conjugated to the ε-NH2 of the C-terminal lysine and a 5-FAM moiety conjugated to an N-terminal GABA linker. The following phosphatases were used PP1α, PP2A, PP2B, PP2C, PTP1B, and LAR.

Each composition was diluted to 4 µM using the appropriate phosphatase buffer for each of the phosphatases. Each of the phosphatases was diluted by serially titrating (each dilution a 2-fold reduction in phosphatase concentration) using the appropriate phosphatase buffer (as recommended by the vendor). The volume of each phosphatase dilution was 5 µl. 5 µl of each 4 µM composition was added to each serial dilution of each phosphatase. The samples were mixed on a plate shaker for 60 seconds and incubated at room temperature for one hour. Reactions were performed in duplicate. After the one hour phosphatase reaction, 5 µl of chymotrypsin was added to each reaction. The plate was mixed on a plate shaker and incubated for 1 hour at room temperature. The plate was then read using a TECAN SAFIRE™ monochromator-based fluorescence plate reader (Excitation at 400 nm (12 nm bandwidth); Emission at 445 nm (12 nm bandwidth); and Emission at 520 nm (12 nm bandwidth) to evaluate whether any of the compositions were substrates of any of the phosphatases. Appropriate controls for each composition and phosphatase were prepared, corresponding to: the nonphosphorylated version of the composition (untreated); the nonphosphorylated version of the composition treated with phosphatase only; the nonphosphorylated version of the composition treated with chymotrypsin only; the nonphosphorylated composition treated with both phosphatase and chymotrypsin; the phosphorylated composition (untreated); the phosphorylated composition treated with phosphatase alone; and the phosphorylated composition treated with chymotrypsin only.

The results indicated that SEQ ID NOs: 100, 109, and 110 were substrates of PP1α. Similarly, SEQ ID NOs: 103, 109, 110, and 113 were substrates of PP2A; SEQ ID NOs: 100 and 110 were substrates of PP2B; SEQ ID NOs: 100, 109, and 110 were substrates of PP2C; and SEQ ID NO: 31 was a substrate for both PTP1B and LAR.

A number of embodiments of the invention have been described. Nevertheless, it will be understood that various modifications may be made without departing from the spirit and scope of the invention. Accordingly, other embodiments are within the scope of the following claims.

---

What is claimed is:

1. A composition of matter capable of being a serine/threonine kinase substrate, comprising:
   (a) a peptide having a length from eight to fifty amino acids, the peptide comprising FSVPPS*PD, where S* is a phosphorylated serine (SEQ ID NO:85); and
   (b) a first detectable moiety associated with the peptide.

2. The composition of claim 1, wherein the first detectable moiety is covalently linked to the peptide.

3. The composition of claim 1, wherein the peptide comprises a protease cleavage site.

4. The composition of claim 3, wherein the protease cleavage site is selected from the group consisting of a chymotrypsin protease cleavage site, a caspase 3 protease cleavage site, a cathepsin G protease cleavage site, a trypsin protease cleavage site, an elastase protease cleavage site, an endoproteinase Asp-N protease cleavage site, and an endoproteinase Glu-N protease cleavage site.

5. The composition of claim 1, wherein the peptide has a length selected from the group consisting of from 8 to 25 amino acids and from 8 to 15 amino acids.

6. The composition of claim 1, further comprising a second detectable moiety associated with the peptide.

7. The composition of claim 1, wherein the composition exhibits an optical property, a magnetic property, or a radioactive property.

8. The composition of claim 7, wherein the composition exhibits an optical property selected from the group consisting of a molar extinction coefficient at an excitation wavelength, a quantum efficiency, an excitation spectrum, an emission spectrum, an excitation wavelength maximum, an emission wavelength maximum, a ratio of excitation amplitudes at two wavelengths, a ratio of emission amplitudes at two wavelengths, an excited state lifetime, an anisotropy, a polarization of emitted light, a resonance energy transfer, and a quenching of emission at a wavelength.

9. The composition of claim 7, wherein the optical property is selected from the group consisting of a fluorescence excitation spectrum, a fluorescence emission spectrum, a fluorescence excitation wavelength maximum, a fluorescence emission wavelength maximum, a ratio of fluorescence excitation amplitudes at two wavelengths, a ratio of fluorescence emission amplitudes at two wavelengths, a fluorescence excited state lifetime, a fluorescence anisotropy, and a quenching of fluorescence emission at a wavelength.

10. The composition of claim 6, wherein the first or second detectable moieties are selected from the group consisting of 5-FAM, 6-FAM, 7-hydroxycoumarin-3-carboxamide, 6-chloro-7-hydroxycoumarin-3-carboxamide, fluorescein-5-isothiocyanate, dichlorotriazinylaminofluorescein, tetramethylrhodamine-5-isothiocyanate, tetramethylrhodamine-6-isothiocyanate, succinimidyl ester of 5-carboxyfluorescein, succinimidyl ester of 6-carboxyfluorescein, 5-carboxytetramethylrhodamine, 6-carboxymethylrhodamine, fluorescein maleimide, and 7-amino-4-methylcoumarin-3-acetic acid.

11. The composition of claim 6, wherein the first detectable moiety, the second detectable moiety or the first and second detectable moiety is a member of a specific binding pair.

12. The composition of claim 6, wherein the first detectable moiety and the second detectable probe moiety form a dark quenching RET pair or a FRET pair.

13. The composition of claim 6, wherein the first detectable moiety is 7-hydroxycoumarin-3-carboxamide and the second detectable moiety is 5-FAM.

14. The composition of claim 6, wherein the first or second detectable probe moiety is covalently linked to the peptide via a linker (L).

15. The composition of claim 14, wherein the L is selected from the group consisting of GABA, diaminopentanyl, and aminohexanoyl.

16. A method for identifying a modulator of activity of a serine/threonine kinase, comprising:
   (a) forming a mixture of a serine/threonine protein kinase, a composition of claim 1, and a test compound;
   (b) contacting the mixture with a protease to form a protease mixture; and
   (c) comparing a measurable property in the protease mixture to the measurable property in a control mixture, wherein the test compound is identified as a modulator of activity of the kinase if the measurable property in the protease mixture is different from the measurable property in the control mixture.

17. A method for identifying a modulator of activity of a serine/threonine phosphatase, comprising:
   (a) contacting a mixture of a serine/threonine protein phosphatase, a composition of claim 1, and a test compound to form a phosphatase mixture, wherein the composition of claim 1 comprises a phosphorylated threonine or serine amino acid;
   (b) contacting the phosphatase mixture with a protease to form a protease mixture; and
   (c) comparing a measurable property in the protease mixture to the measurable property in a control protease mixture, wherein the test compound is identified as a modulator of activity of the phosphatase if the measurable property in the protease mixture is different from the measurable property in the control mixture.

18. An article of manufacture comprising:
   (a) packaging matter; and
   (b) a composition of matter according to claim 1 associated with the packaging material.

19. The article of claim 18, further comprising at least one member selected form the group consisting of a serine/threonine protein kinase, a serine/threonine protein phosphatase, a protease and ATP.

20. The composition of claim 1, wherein the peptide comprises PRPFSVPPS*PDK (SEQ ID NO: 86).

* * * * *

SEQUENCE LISTING

```
<160> NUMBER OF SEQ ID NOS: 216

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Ile Tyr Ala Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Glu Ala Ile Tyr Ala Ala Pro
```

```
1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ala Glu Ala Ile Tyr Ala Ala Pro Gly Asp Lys
1               5                   10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Asp Tyr Leu Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Gln Asp Tyr Leu Ser Leu
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Asp Gln Asp Tyr Leu Ser Leu Asp Lys
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Ile Tyr Gly Val
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 8

Glu Glu Ile Tyr Gly Val Ile
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Glu Glu Ile Tyr Gly Val Ile Glu Lys
1               5                   10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly, Ala or Glu

<400> SEQUENCE: 10

Thr Xaa Tyr Val Ala
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Thr Gly Tyr Val Ala Arg
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Thr Ala Tyr Val Ala Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Thr Glu Tyr Val Ala Thr
1               5
```

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Val Leu Thr Gly Tyr Val Ala Arg Arg Lys
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Asp Glu Ile Thr Ala Tyr Val Ala Thr Arg Lys
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Gly Ile Ile Thr Glu Tyr Val Ala Thr Arg Lys
1               5                   10

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Glu Tyr Ile Gln
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu Glu Glu Tyr Ile Gln Ile
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Glu Glu Glu Glu Tyr Ile Gln Ile Val Lys
1               5                   10

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Tyr Ser Gln Val
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Asp Tyr Ser Gln Val Leu
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Glu Gly Asp Tyr Ser Gln Val Leu Glu Lys
1               5                   10

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Tyr

<400> SEQUENCE: 23

Ala Ile Tyr Ala Ala
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Tyr

<400> SEQUENCE: 24

Glu Ala Ile Tyr Ala Ala Pro
```

-continued

```
<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Tyr

<400> SEQUENCE: 25

Glu Ala Glu Ala Ile Tyr Ala Ala Pro Gly Asp Lys
1               5                   10

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Tyr

<400> SEQUENCE: 26

Gln Asp Tyr Leu Ser
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Tyr

<400> SEQUENCE: 27

Asp Gln Asp Tyr Leu Ser Leu
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Tyr

<400> SEQUENCE: 28

Gly Asp Gln Asp Tyr Leu Ser Leu Asp Lys
1               5                   10

<210> SEQ ID NO 29
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Tyr

<400> SEQUENCE: 29

Glu Ile Tyr Gly Val
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Tyr

<400> SEQUENCE: 30

Glu Glu Ile Tyr Gly Val Ile
1               5

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Tyr

<400> SEQUENCE: 31

Glu Glu Glu Ile Tyr Gly Val Ile Glu Lys
1               5                   10

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly, Ala or Glu
<220> FEATURE:
<221> NAME/KEY: MOD_RES
<222> LOCATION: (3)..(3)
<223> OTHER INFORMATION: Phosphorylated Tyr

<400> SEQUENCE: 32

Thr Xaa Tyr Val Ala
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(4)
<223> OTHER INFORMATION: Phosphorylated Tyr

<400> SEQUENCE: 33

Leu Thr Gly Tyr Val Ala Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Tyr

<400> SEQUENCE: 34

Ile Thr Ala Tyr Val Ala Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Tyr

<400> SEQUENCE: 35

Ile Thr Glu Tyr Val Ala Thr
1               5

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Tyr

<400> SEQUENCE: 36

Gly Val Leu Thr Gly Tyr Val Ala Arg Arg Lys
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphorylated Tyr

<400> SEQUENCE: 37

Asp Asp Glu Ile Thr Ala Tyr Val Ala Thr Arg Lys
1               5                   10
```

-continued

```
<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphorylated Tyr

<400> SEQUENCE: 38

Thr Gly Ile Ile Thr Glu Tyr Val Ala Thr Arg Lys
1               5                   10

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Tyr

<400> SEQUENCE: 39

Glu Glu Tyr Ile Gln
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Tyr

<400> SEQUENCE: 40

Glu Glu Glu Tyr Ile Gln Ile
1               5

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Tyr

<400> SEQUENCE: 41

Glu Glu Glu Glu Tyr Ile Gln Ile Val Lys
1               5                   10

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
-continued

<220> FEATURE:
<221> NAME/KEY: MOD_RES
<222> LOCATION: (2)..(2)
<223> OTHER INFORMATION: Phosphorylated Tyr

<400> SEQUENCE: 42

Asp Tyr Ser Gln Val
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Tyr

<400> SEQUENCE: 43

Gly Asp Tyr Ser Gln Val Leu
1               5

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Tyr

<400> SEQUENCE: 44

Glu Gly Asp Tyr Ser Gln Val Leu Glu Lys
1               5                   10

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe, Trp or Tyr
<220> FEATURE:
<221> NAME/KEY: MOD_RES
<222> LOCATION: (4)..(4)
<223> OTHER INFORMATION: Ser or Thr

<400> SEQUENCE: 45

Arg Arg Xaa Xaa Leu
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Leu Arg Arg Phe Ser Leu Gly
```

```
<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ala Leu Arg Arg Phe Ser Leu Gly Glu Lys
1               5                   10

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Trp or Tyr
<220> FEATURE:
<221> NAME/KEY: MOD_RES
<222> LOCATION: (3)..(3)
<223> OTHER INFORMATION: Ser or Thr

<400> SEQUENCE: 48

Leu Xaa Xaa Thr Thr
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Leu Phe Ser Thr Thr Pro
1               5

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Gly Gly Leu Phe Ser Thr Thr Pro Gly Gly Thr Lys
1               5                   10

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Trp or Tyr
<220> FEATURE:
<221> NAME/KEY: MOD_RES
```

```
<222> LOCATION: (3)..(3)
<223> OTHER INFORMATION: Ser or Thr

<400> SEQUENCE: 51

Xaa Leu Xaa Leu Asp
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Asp Tyr Leu Ser Leu Asp Lys
1               5

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Asp Gln Asp Tyr Leu Ser Leu Asp Lys
1               5                   10

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val, Ala or Gln
<220> FEATURE:
<221> NAME/KEY: MOD_RES
<222> LOCATION: (3)..(3)
<223> OTHER INFORMATION: Phe, Trp or Tyr
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Val or Leu

<400> SEQUENCE: 54

Arg Xaa Xaa Xaa Xaa
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Asn Arg Val Phe Ser Val Ala
1               5
```

```
<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Pro Arg Ala Phe Ser Val Gly
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Arg Gln Phe Ser Leu Arg
1               5

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Leu Asn Arg Val Phe Ser Val Ala Cys
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ala Arg Pro Arg Ala Phe Ser Val Gly Lys
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Arg Arg Arg Gln Phe Ser Leu Arg Arg Lys Ala Lys
1               5                   10

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: Phe, Trp or Tyr
<220> FEATURE:
<221> NAME/KEY: MOD_RES
<222> LOCATION: (4)..(4)
<223> OTHER INFORMATION: Ser or Thr

<400> SEQUENCE: 61

Thr Xaa Ser Xaa Leu
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Thr Phe Ser Ser Leu Ala
1               5

<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Pro Arg Thr Phe Ser Ser Leu Ala Glu Gly Lys
1               5                   10

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro or Ile
<220> FEATURE:
<221> NAME/KEY: MOD_RES
<222> LOCATION: (2)..(2)
<223> OTHER INFORMATION: Phe, Trp or Tyr
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Gly, Lys or Asp

<400> SEQUENCE: 64

Xaa Xaa Xaa Pro Xaa
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65
```

```
Ala Pro Phe Ser Pro Gly Gly
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

His Pro Phe Ser Pro Lys Lys
1               5

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Ile Phe Ser Pro Asp Val
1               5

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Val Ala Pro Phe Ser Pro Gly Gly Arg Ala Lys
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Lys His Pro Phe Ser Pro Lys Lys Ala Lys
1               5                   10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Ile Lys Ile Phe Ser Pro Asp Val Glu Lys
1               5                   10

<210> SEQ ID NO 71
<211> LENGTH: 6
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Trp or Tyr
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Ala, Glu or Gln
<220> FEATURE:
<221> NAME/KEY: MOD_RES
<222> LOCATION: (4)..(4)
<223> OTHER INFORMATION: Tyr or His

<400> SEQUENCE: 71

Xaa Xaa Xaa Xaa Val Ala
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Glu Phe Thr Ala Tyr Val Ala
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Ile Phe Thr Glu Tyr Val Ala
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Val Phe Thr Gln His Val Ala
1               5

<210> SEQ ID NO 75
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Asp Asp Glu Phe Thr Ala Tyr Val Ala Thr Arg Lys
1               5                   10
```

```
<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Gly Ile Phe Thr Glu Tyr Val Ala Thr Arg Lys
1               5                   10

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Thr Gly Val Phe Thr Gln His Val Ala Thr Arg Lys
1               5                   10

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Trp or Tyr
<220> FEATURE:
<221> NAME/KEY: MOD_RES
<222> LOCATION: (3)..(3)
<223> OTHER INFORMATION: Ser or Thr

<400> SEQUENCE: 78

Ile Xaa Xaa Ile Ala Asn
1               5

<210> SEQ ID NO 79
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ile Phe Ser Ile Ala Asn Ser
1               5

<210> SEQ ID NO 80
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Arg Ile Phe Ser Ile Ala Asn Ser Ile Val Lys
1               5                   10

<210> SEQ ID NO 81
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe, Trp or Tyr
<220> FEATURE:
<221> NAME/KEY: MOD_RES
<222> LOCATION: (5)..(5)
<223> OTHER INFORMATION: Ser or Thr

<400> SEQUENCE: 81

Ser Ile Ala Xaa Xaa Ile
1               5

<210> SEQ ID NO 82
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asp Ser Ile Ala Phe Ser Ile Val
1               5

<210> SEQ ID NO 83
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Ile Asp Ser Ile Ala Phe Ser Ile Val Gly Lys
1               5                   10

<210> SEQ ID NO 84
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (5)..(5)
<223> OTHER INFORMATION: Phosphorylated Ser

<400> SEQUENCE: 84

Xaa Val Pro Pro Ser Pro
1               5

<210> SEQ ID NO 85
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (6)..(6)
<223> OTHER INFORMATION: Phosphorylated Ser

<400> SEQUENCE: 85

Phe Ser Val Pro Pro Ser Asp
1               5

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phosphorylated Ser

<400> SEQUENCE: 86

Pro Arg Pro Phe Ser Val Pro Pro Ser Pro Asp Lys
1               5                   10

<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Glu
<220> FEATURE:
<221> NAME/KEY: MOD_RES
<222> LOCATION: (3)..(3)
<223> OTHER INFORMATION: Phe, Trp or Tyr
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Ile or Gln

<400> SEQUENCE: 87

Asp Xaa Xaa Xaa Xaa
1               5

<210> SEQ ID NO 88
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Asp Ala Phe Ser Ile Ile
1               5

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89
```

Glu Asp Glu Phe Ser Gln Asn
1               5

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Glu Glu Asp Ala Phe Ser Ile Ile Gly Lys
1               5                   10

<210> SEQ ID NO 91
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Glu Asp Glu Phe Ser Gln Asn Glu Glu Lys
1               5                   10

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Trp or Tyr
<220> FEATURE:
<221> NAME/KEY: MOD_RES
<222> LOCATION: (3)..(3)
<223> OTHER INFORMATION: Ser or Thr

<400> SEQUENCE: 92

Asp Xaa Xaa Gln Val
1               5

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Glu Gly Asp Tyr Ser Gln Val
1               5

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Glu Gly Asp Tyr Ser Gln Val Leu Glu Lys

```
1               5                   10
```

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe, Trp or Tyr
<220> FEATURE:
<221> NAME/KEY: MOD_RES
<222> LOCATION: (4)..(4)
<223> OTHER INFORMATION: Phosphorylated Ser or Phosphorylated Thr

<400> SEQUENCE: 95

Arg Arg Xaa Xaa Leu
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 96

Leu Arg Arg Phe Ser Leu Gly
1               5

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Ser

<400> SEQUENCE: 97

Ala Leu Arg Arg Phe Ser Leu Gly Glu Lys
1               5                   10

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Trp or Tyr
<220> FEATURE:
<221> NAME/KEY: MOD_RES
<222> LOCATION: (3)..(3)
<223> OTHER INFORMATION: Phosphorylated Ser or Phosphorylated Thr

<400> SEQUENCE: 98

Leu Xaa Xaa Thr Thr

```
<210> SEQ ID NO 99
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 99

Gly Leu Phe Ser Thr Thr Pro
1               5

<210> SEQ ID NO 100
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Ser

<400> SEQUENCE: 100

Arg Gly Gly Leu Phe Ser Thr Thr Pro Gly Gly Thr Lys
1               5                   10

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Trp or Tyr
<220> FEATURE:
<221> NAME/KEY: MOD_RES
<222> LOCATION: (3)..(3)
<223> OTHER INFORMATION: Phosphorylated Ser or Phosphorylated Thr

<400> SEQUENCE: 101

Xaa Leu Xaa Leu Asp
1               5

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 102

Asp Tyr Leu Ser Leu Asp Lys
1               5

<210> SEQ ID NO 103
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphorylated Ser

<400> SEQUENCE: 103

Gly Asp Gln Asp Tyr Leu Ser Leu Asp Lys
1               5                   10

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val, Ala or Gln
<220> FEATURE:
<221> NAME/KEY: MOD_RES
<222> LOCATION: (3)..(3)
<223> OTHER INFORMATION: Phe, Trp or Tyr
<220> FEATURE:
<221> NAME/KEY: MOD_RES
<222> LOCATION: (4)..(4)
<223> OTHER INFORMATION: Phosphorylated Ser or Phosphorylated Thr
<220> FEATURE:
<221> NAME/KEY: MOD_RES
<222> LOCATION: (5)..(5)
<223> OTHER INFORMATION: Val or Leu

<400> SEQUENCE: 104

Arg Xaa Xaa Xaa Xaa
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 105

Asn Arg Val Phe Ser Val Ala
1               5

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 106

Pro Arg Ala Phe Ser Val Gly
```

-continued

```
<210> SEQ ID NO 107
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 107

Arg Arg Gln Phe Ser Leu Arg
1               5

<210> SEQ ID NO 108
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphorylated Ser

<400> SEQUENCE: 108

Lys Leu Asn Arg Val Phe Ser Val Ala Cys
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphorylated Ser

<400> SEQUENCE: 109

Ala Arg Pro Arg Ala Phe Ser Val Gly Lys
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Ser

<400> SEQUENCE: 110

Arg Arg Arg Gln Phe Ser Leu Arg Arg Lys Ala Lys
1               5                   10

<210> SEQ ID NO 111
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Trp or Tyr
<220> FEATURE:
<221> NAME/KEY: MOD_RES
<222> LOCATION: (4)..(4)
<223> OTHER INFORMATION: Phosphorylated Ser or Phosphorylated Thr

<400> SEQUENCE: 111

Thr Xaa Ser Xaa Leu
1               5

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 112

Arg Thr Phe Ser Ser Leu Ala
1               5

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phosphorylated Ser

<400> SEQUENCE: 113

Arg Pro Arg Thr Phe Ser Ser Leu Ala Glu Gly Lys
1               5                   10

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro or Ile
<220> FEATURE:
<221> NAME/KEY: MOD_RES
<222> LOCATION: (2)..(2)
<223> OTHER INFORMATION: Gly, Lys or Asp
<220> FEATURE:
<221> NAME/KEY: MOD_RES
<222> LOCATION: (3)..(3)
<223> OTHER INFORMATION: Phosphorylated Ser or Phosphorylated Thr
<220> FEATURE:
<221> NAME/KEY: MOD_RES
<222> LOCATION: (5)..(5)
<223> OTHER INFORMATION: Phe, Trp or Tyr

<400> SEQUENCE: 114

Xaa Xaa Xaa Pro Xaa
```

-continued

```
<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 115

Ala Pro Phe Ser Pro Gly Gly
1               5

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 116

His Pro Phe Ser Pro Lys Lys
1               5

<210> SEQ ID NO 117
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 117

Lys Ile Phe Ser Pro Asp Val
1               5

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 118

Val Ala Pro Phe Ser Pro Gly Gly Arg Ala Lys
1               5                   10

<210> SEQ ID NO 119
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Ser

<400> SEQUENCE: 119

Ala Lys His Pro Phe Ser Pro Lys Lys Ala Lys
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Ser

<400> SEQUENCE: 120

Ile Ile Lys Ile Phe Ser Pro Asp Val Glu Lys
1               5                   10

<210> SEQ ID NO 121
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phe, Trp or Tyr
<220> FEATURE:
<221> NAME/KEY: MOD_RES
<222> LOCATION: (2)..(2)
<223> OTHER INFORMATION: Phosphorylated Ser or Phosphorylated Thr
<220> FEATURE:
<221> NAME/KEY: MOD_RES
<222> LOCATION: (3)..(3)
<223> OTHER INFORMATION: Ala, Glu or Gln
<220> FEATURE:
<221> NAME/KEY: MOD_RES
<222> LOCATION: (4)..(4)
<223> OTHER INFORMATION: Tyr or His

<400> SEQUENCE: 121

Xaa Xaa Xaa Xaa Val Ala
1               5

<210> SEQ ID NO 122
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Thr

<400> SEQUENCE: 122

Glu Phe Thr Ala Tyr Val Ala
1               5

<210> SEQ ID NO 123

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Thr

<400> SEQUENCE: 123

Ile Phe Thr Glu Tyr Val Ala
1               5

<210> SEQ ID NO 124
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Thr

<400> SEQUENCE: 124

Val Phe Thr Gln His Val Ala
1               5

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Thr

<400> SEQUENCE: 125

Asp Asp Glu Phe Thr Ala Tyr Val Ala Thr Arg Lys
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Thr

<400> SEQUENCE: 126

Thr Gly Ile Phe Thr Glu Tyr Val Ala Thr Arg Lys
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (5)..(5)
<223> OTHER INFORMATION: Phosphorylated Thr

<400> SEQUENCE: 127

Thr Gly Val Phe Thr Gln His Val Ala Thr Arg Lys
1               5                   10

<210> SEQ ID NO 128
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Trp or Tyr
<220> FEATURE:
<221> NAME/KEY: MOD_RES
<222> LOCATION: (3)..(3)
<223> OTHER INFORMATION: Phosphorylated Ser or Phosphorylated Thr

<400> SEQUENCE: 128

Ile Xaa Xaa Ile Ala Asn
1               5

<210> SEQ ID NO 129
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 129

Arg Ile Phe Ser Ile Ala Asn Ser
1               5

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 130

Gln Arg Ile Phe Ser Ile Ala Asn Ser Ile Val Lys
1               5                   10

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe, Trp or Tyr
<220> FEATURE:
<221> NAME/KEY: MOD_RES
```

```
<222> LOCATION: (5)..(5)
<223> OTHER INFORMATION: Phosphorylated Ser or Phosphorylated Thr

<400> SEQUENCE: 131

Ser Ile Ala Xaa Xaa Ile
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Ser

<400> SEQUENCE: 132

Asp Ser Ile Ala Phe Ser Ile Val
1               5

<210> SEQ ID NO 133
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phosphorylated Ser

<400> SEQUENCE: 133

Arg Ile Asp Ser Ile Ala Phe Ser Ile Val Gly Lys
1               5                   10

<210> SEQ ID NO 134
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Phosphorylated Ser or Phosphorylated Thr
<220> FEATURE:
<221> NAME/KEY: MOD_RES
<222> LOCATION: (5)..(5)
<223> OTHER INFORMATION: Phosphorylated Ser

<400> SEQUENCE: 134

Xaa Val Pro Pro Ser Pro
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phosphorylated Ser
<220> FEATURE:
<221> NAME/KEY: MOD_RES
```

```
<222> LOCATION: (6)..(6)
<223> OTHER INFORMATION: Phosphorylated Ser

<400> SEQUENCE: 135

Phe Ser Val Pro Pro Ser Asp
1               5

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser
<220> FEATURE:
<221> NAME/KEY: MOD_RES
<222> LOCATION: (9)..(9)
<223> OTHER INFORMATION: Phosphorylated Ser

<400> SEQUENCE: 136

Pro Arg Pro Phe Ser Val Pro Pro Ser Pro Asp Lys
1               5                   10

<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Glu
<220> FEATURE:
<221> NAME/KEY: MOD_RES
<222> LOCATION: (3)..(3)
<223> OTHER INFORMATION: Phe, Trp or Tyr
<220> FEATURE:
<221> NAME/KEY: MOD_RES
<222> LOCATION: (4)..(4)
<223> OTHER INFORMATION: Phosphorylated Ser or Phosphorylated Thr
<220> FEATURE:
<221> NAME/KEY: MOD_RES
<222> LOCATION: (5)..(5)
<223> OTHER INFORMATION: Ile or Gln

<400> SEQUENCE: 137

Asp Xaa Xaa Xaa Xaa
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 138

Glu Asp Ala Phe Ser Ile Ile
1               5

<210> SEQ ID NO 139
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 139

Glu Asp Glu Phe Ser Gln Asn
1               5

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Ser

<400> SEQUENCE: 140

Glu Glu Asp Ala Phe Ser Ile Ile Gly Lys
1               5                   10

<210> SEQ ID NO 141
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Ser

<400> SEQUENCE: 141

Arg Glu Asp Glu Phe Ser Gln Asn Glu Glu Lys
1               5                   10

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Phe, Trp or Tyr
<220> FEATURE:
<221> NAME/KEY: MOD_RES
<222> LOCATION: (3)..(3)
<223> OTHER INFORMATION: Phosphorylated Ser or Phosphorylated Thr

<400> SEQUENCE: 142

Asp Xaa Xaa Gln Val
1               5

<210> SEQ ID NO 143
<211> LENGTH: 7
<212> TYPE: PRT
<213> ORGANISM: Artificial Sequence
<220> FEATURE:
```

-continued

<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 143

Glu Gly Asp Tyr Ser Gln Val
1               5

<210> SEQ ID NO 144
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 144

Glu Gly Asp Tyr Ser Gln Val Leu Glu Lys
1               5                   10

<210> SEQ ID NO 145
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 145

Arg Arg Xaa Leu
1

<210> SEQ ID NO 146
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr

<400> SEQUENCE: 146

Leu Xaa Thr Thr
1

<210> SEQ ID NO 147
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr

<400> SEQUENCE: 147

Leu Xaa Leu Asp
1

<210> SEQ ID NO 148
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val, Ala or Gln
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Val or Leu

<400> SEQUENCE: 148

Arg Xaa Xaa Xaa
1

<210> SEQ ID NO 149
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 149

Thr Ser Xaa Leu
1

<210> SEQ ID NO 150
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro or Ile
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (4)..(4)
<223> OTHER INFORMATION: Gly, Lys or Asp

<400> SEQUENCE: 150

Xaa Xaa Pro Xaa
1

<210> SEQ ID NO 151
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: Ala, Glu or Gln
<220> FEATURE:
<221> NAME/KEY: MOD_RES
<222> LOCATION: (3)..(3)
<223> OTHER INFORMATION: Tyr or His

<400> SEQUENCE: 151

Xaa Xaa Xaa Val Ala
1               5

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr

<400> SEQUENCE: 152

Ile Xaa Ile Ala Asn
1               5

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Thr

<400> SEQUENCE: 153

Ser Ile Ala Xaa Ile
1               5

<210> SEQ ID NO 154
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (5)..(5)
<223> OTHER INFORMATION: Phosphorylated Ser

<400> SEQUENCE: 154

Xaa Val Pro Pro Ser Pro
1               5

<210> SEQ ID NO 155
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Glu
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (4)..(4)
<223> OTHER INFORMATION: Ile or Gln

<400> SEQUENCE: 155

Asp Xaa Xaa Xaa
1

<210> SEQ ID NO 156
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr

<400> SEQUENCE: 156

Asp Xaa Gln Val
1

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Thr

<400> SEQUENCE: 157

Arg Arg Phe Xaa Leu
1               5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 158

Leu Phe Xaa Thr Thr
1               5

<210> SEQ ID NO 159
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 159

Tyr Leu Xaa Leu Asp
1               5

<210> SEQ ID NO 160
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val, Ala or Gln
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Val or Ile

<400> SEQUENCE: 160

Arg Xaa Phe Xaa Xaa
1               5

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Thr

<400> SEQUENCE: 161

Thr Phe Ser Xaa Leu
1               5

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pro or Ile
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (5)..(5)
<223> OTHER INFORMATION: Gly, Lys or Asp
```

```
<400> SEQUENCE: 162

Xaa Phe Xaa Pro Xaa
1               5

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser or Thr
<220> FEATURE:
<221> NAME/KEY: MOD_RES
<222> LOCATION: (3)..(3)
<223> OTHER INFORMATION: Ala, Glu or Gln
<220> FEATURE:
<221> NAME/KEY: MOD_RES
<222> LOCATION: (4)..(4)
<223> OTHER INFORMATION: Tyr or His

<400> SEQUENCE: 163

Phe Xaa Xaa Xaa Val Ala
1               5

<210> SEQ ID NO 164
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 164

Ile Phe Xaa Ile Ala Asn
1               5

<210> SEQ ID NO 165
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser or Thr

<400> SEQUENCE: 165

Ser Ile Ala Phe Xaa Ile
1               5

<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Glu
```

```
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (5)..(5)
<223> OTHER INFORMATION: Ile or Gln

<400> SEQUENCE: 166

Asp Xaa Phe Xaa Xaa
1               5

<210> SEQ ID NO 167
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 167

Asp Tyr Xaa Gln Val
1               5

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Glu Ile Tyr Ala Ala
1               5

<210> SEQ ID NO 169
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Glu Glu Ile Tyr Ala Ala Arg
1               5

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ala Ala Glu Glu Ile Tyr Ala Ala Arg Arg Gly Lys
1               5                   10

<210> SEQ ID NO 171
<211> LENGTH: 5
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Tyr

<400> SEQUENCE: 171

Glu Ile Tyr Ala Ala
1               5

<210> SEQ ID NO 172
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Tyr

<400> SEQUENCE: 172

Glu Glu Ile Tyr Ala Ala Arg
1               5

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Tyr

<400> SEQUENCE: 173

Ala Ala Glu Glu Ile Tyr Ala Ala Arg Arg Gly Lys
1               5                   10

<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Thr

<400> SEQUENCE: 174

Arg Gln Phe Xaa Val
1               5

<210> SEQ ID NO 175
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Arg Gln Phe Ser Val Ala
1               5
```

```
<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Lys Lys Lys Ala Leu Ser Arg Gln Phe Ser Val Ala Ala Lys
1               5                   10

<210> SEQ ID NO 177
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 177

Ser Phe Xaa Ser Ser
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Glu Ser Phe Ser Ser Ser Glu
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Glu Ser Phe Ser Ser Ser Glu Glu Lys
1               5

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 180

Phe Gly Xaa Pro Asn
1               5

<210> SEQ ID NO 181
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Phe Gly Ser Pro Asn Arg
1               5

<210> SEQ ID NO 182
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Val Leu Ala Lys Ser Phe Gly Ser Pro Asn Arg Ala Arg Lys Lys Lys
1               5                   10                  15

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Thr

<400> SEQUENCE: 183

Arg Arg Tyr Xaa Asn
1               5

<210> SEQ ID NO 184
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gln Arg Arg Tyr Ser Asn Val
1               5

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Lys Lys Arg Pro Gln Arg Arg Tyr Ser Asn Val Leu Lys
1               5                   10

<210> SEQ ID NO 186
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Ser or Thr

<400> SEQUENCE: 186

Arg Leu Xaa Phe Ala
1               5

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Arg Arg Leu Ser Phe Ala Glu
1               5

<210> SEQ ID NO 188
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Arg Arg Arg Leu Ser Phe Ala Glu Pro Gly Lys
1               5                   10

<210> SEQ ID NO 189
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 189

Pro Phe Xaa Pro Ser
1               5

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Glu Pro Phe Thr Pro Ser Gly
1               5

<210> SEQ ID NO 191
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191
```

```
Leu Val Glu Pro Phe Thr Pro Ser Gly Glu Ala Pro Asn Gln Lys Lys
1               5                   10                  15

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser or Thr

<400> SEQUENCE: 192

Glu Ala Xaa Phe Ala
1               5

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ile Glu Ala Ser Phe Ala Glu
1               5

<210> SEQ ID NO 194
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Glu Val Ile Glu Ala Ser Phe Ala Glu Gln Glu Ala Lys
1               5                   10

<210> SEQ ID NO 195
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Thr
<220> FEATURE:
<221> NAME/KEY: MOD_RES
<222> LOCATION: (4)..(4)
<223> OTHER INFORMATION: Phosphorylated Ser or Phosphorylated Thr

<400> SEQUENCE: 195

Arg Gln Phe Xaa Val
1               5

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(5)
<223> OTHER INFORMATION: Phosphorylated Ser

<400> SEQUENCE: 196

Ser Arg Gln Phe Ser Val Ala
1               5

<210> SEQ ID NO 197
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Phosphorylated Ser

<400> SEQUENCE: 197

Lys Lys Lys Ala Leu Ser Arg Gln Phe Ser Val Ala Ala Lys
1               5                   10

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Ser or Phosphorylated Thr

<400> SEQUENCE: 198

Ser Phe Xaa Ser Ser
1               5

<210> SEQ ID NO 199
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 199

Glu Ser Phe Ser Ser Ser Glu
1               5

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 200

Glu Ser Phe Ser Ser Ser Glu Glu Lys
```

```
<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Ser or Phosphorylated Thr

<400> SEQUENCE: 201

Phe Gly Xaa Pro Asn
1               5

<210> SEQ ID NO 202
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 202

Ser Phe Gly Ser Pro Asn Arg
1               5

<210> SEQ ID NO 203
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Phosphorylated Ser

<400> SEQUENCE: 203

Val Leu Ala Lys Ser Phe Gly Ser Pro Asn Arg Ala Arg Lys Lys Lys
1               5                   10                  15

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser or Phosphorylated Thr

<400> SEQUENCE: 204

Arg Arg Tyr Xaa Asn
1               5

<210> SEQ ID NO 205
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 205

Gln Arg Arg Tyr Ser Asn Val
1               5

<210> SEQ ID NO 206
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Phosphorylated Ser

<400> SEQUENCE: 206

Lys Lys Arg Pro Gln Arg Arg Tyr Ser Asn Val Leu Lys
1               5                   10

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Ser or Phosphorylated Thr

<400> SEQUENCE: 207

Arg Leu Xaa Phe Ala
1               5

<210> SEQ ID NO 208
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 208

Arg Arg Leu Ser Phe Ala Glu
1               5

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Phosphorylated Ser

<400> SEQUENCE: 209
```

```
Arg Arg Arg Leu Ser Phe Ala Glu Pro Gly Lys
1               5                   10
```

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Ser or Phosphorylated Thr

<400> SEQUENCE: 210

```
Pro Phe Xaa Pro Ser
1               5
```

<210> SEQ ID NO 211
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Thr

<400> SEQUENCE: 211

```
Glu Pro Phe Thr Pro Ser Gly
1               5
```

<210> SEQ ID NO 212
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Thr

<400> SEQUENCE: 212

```
Leu Val Glu Pro Phe Thr Pro Ser Gly Glu Ala Pro Asn Gln Lys Lys
1               5                   10                  15
```

<210> SEQ ID NO 213
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phosphorylated Ser or Phosphorylated Thr

<400> SEQUENCE: 213

```
Glu Ala Xaa Phe Ala
1               5
```

<210> SEQ ID NO 214
<211> LENGTH: 7
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphorylated Ser

<400> SEQUENCE: 214

Ile Glu Ala Ser Phe Ala Glu
1               5

<210> SEQ ID NO 215
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Ser

<400> SEQUENCE: 215

Glu Val Ile Glu Ala Ser Phe Ala Glu Gln Glu Ala Lys
1               5                   10

<210> SEQ ID NO 216
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Phosphorylated Ser

<400> SEQUENCE: 216

Asp Gln Asp Tyr Leu Ser Leu
1               5
```